(12) United States Patent
Paul

(10) Patent No.: US 7,947,288 B2
(45) Date of Patent: May 24, 2011

(54) VIRAL PARTICLES ENCODING MULTIFUNCTIONAL CYTOKINES

(75) Inventor: Stephane Paul, Strasbourg Cedex (FR)

(73) Assignee: Transgene S.A., Strasbourg Cedex (FR)

( * ) Notice: Subject to any disclaimer, the term of this patent is extended or adjusted under 35 U.S.C. 154(b) by 225 days.

(21) Appl. No.: 12/430,723

(22) Filed: Apr. 27, 2009

(65) Prior Publication Data

US 2010/0196324 A1     Aug. 5, 2010

Related U.S. Application Data

(62) Division of application No. 10/565,371, filed as application No. PCT/EP2004/008114 on Jul. 20, 2004, now Pat. No. 7,534,585.

(60) Provisional application No. 60/539,320, filed on Jan. 28, 2004.

(30) Foreign Application Priority Data

Jul. 21, 2003   (EP) .................................... 03360086

(51) Int. Cl.
   C12N 15/63      (2006.01)
   C12N 15/86      (2006.01)
   A61K 39/325     (2006.01)

(52) U.S. Cl. ............... 424/233.1; 435/235.1; 435/320.1; 435/325

(58) Field of Classification Search .................. None
   See application file for complete search history.

(56) References Cited

U.S. PATENT DOCUMENTS

| 5,359,035 | A  | 10/1994 | Habermann |
| 6,552,005 | B1 | 4/2003  | Buchsbaum et al. |

FOREIGN PATENT DOCUMENTS

| DE | 198 23 351 A1 | 12/1998 |
| EP | 0 158 198 | 10/1985 |
| EP | 0 225 579 | 6/1987 |
| EP | 0 288 809 | 11/1988 |
| EP | 0 816 510 A1 | 1/1998 |
| WO | WO 93/20849 | 10/1993 |
| WO | WO 94/21792 | 9/1994 |
| WO | WO 98/08947 | 3/1998 |
| WO | WO 98/40498 | 9/1998 |
| WO | WO 99/36440 | 7/1999 |
| WO | WO 99/60128 | 11/1999 |
| WO | WO 00/53761 | 9/2000 |
| WO | WO 01/10912 | 2/2001 |
| WO | WO 01/68896 | 9/2001 |
| WO | WO 01/93898 | 12/2001 |
| WO | WO 02/22805 A | 3/2002 |
| WO | WO 02/101049 | 12/2002 |
| WO | WO 02/102404 | 12/2002 |
| WO | WO 03/035105 | 5/2003 |
| WO | WO 03/048334 | 6/2003 |

OTHER PUBLICATIONS

Bagriacik, Umit et al., "CD43 potentiates CD3-induced proliferation of murine intestinal intraepithelial lymphocytes," 79(3) Immunology and Cell Biology 303-307 (Jun. 2001).
Bulfone-Paus, S et al., "Differential Regulation of Human T Lymphoblast Functions by IL2 and IL-15," 9(7) Cytokine 507-513 (Jul. 1997).
Cao, Renhai et al., "Interleukin-18 acts as an angiogenesis and tumor suppressor," 13 The FASEB Journal 2195-2202 (Dec. 1999).
Danthinne, X. et al., "Production of first generation adenovirus vectors: a review," 7 Gene Therapy 1707-1714 (2000).
Dobmeyer, T. et al., "Mechanism of gamma sigma T-Cell-Mediated Inhibition of Stem Cell Differentiation in Vitro: Possible Relevance for Myelosuppression in HIV-Infected Individuals," 184(1) Cellular Immunology (Feb. 25, 1998).
European Search Report dated Aug. 21, 2007 issued in European counterpart patent application 04 76 3359.
Gillies, Stephen D. et al., "Bi-functional cytokine fusion proteins for gene therapy and anti-body-targeted treatment of cancer," 51 Cancer Immunol Immunothere. 449-460 (2002).
Hashimoto, Wataru et al., "Differential Antitumor Effects of Administration of Recombinant IL-18 or Recombinant IL-12 are Mediated Primarily by Fas-Fas Ligand- and Perforin-Induced Tumor Apoptosis, Respectively", 163 The Journal of Immunology 583-589 (1999).
He, Z. et al., "Viral Recombinant Vaccines to the E6 and E7 Antigens of HPV-16," 270 Virology 146-161 (2000).
International Search Report issued in corres. PCT/EP2004/008114, Mar. 31, 2005, EPO.
Ju, Dian Wen et al., "Adenovirus-mediated combined suicide gene and interleukin-2 gene therapy for the treatment of established tumor and induction of antitumor immunity," 124(12) Journal of Cancer Research and Clinical Oncology 683-689 (1998).
Kaufmann, A.M., et al., "Comparison of Cytokines and CD80 for Enhancement of Immunogenicity of Cervical Cancer Cells," 202(4) Immunobiology 339-352 (Oct. 2000). Kim, Soo-Hyun et al., "Site-specific mutations in the mature form of human IL-18 with enhanced biological activity and decreased neutralization by IL-18 binding protein," 98(6) Proc. Natl. Acad. Sci.3304-3309 (Mar. 13, 2001).
Kim, Soo-Hyun et al., "Identification of Amino Acid Residues Critical for Biological Activity in Human Interleukin-18," 277(13) The Journal of Biological Chemistry 10998-11003 (Mar. 29, 2002).
Kondo, M., et al., "Enhancement of Interleukin-2-Induced Lymphokine-Activated Killer Activity by Interleukin 7 against Autologous Human Renal Cell Carcinoma," 55(6) Oncology 588-593 (Nov. 1998).

(Continued)

Primary Examiner — Prema Mertz
(74) Attorney, Agent, or Firm — Buchanan Ingersoll & Rooney PC

(57) ABSTRACT

The present invention relates to a novel fusion protein with the formula X-Y, or Y-X, wherein X represents a first immunoregulating polypeptide and Y represents a second immunoregulating polypeptide different from X. The present invention also relates to a nucleic acid molecule encoding such a fusion protein and a vector comprising such a nucleic acid molecule. The present invention also provides infectious viral particles and host cells comprising such a nucleic acid molecule or such a vector as well as a process for producing such infectious viral particles. The present invention also relates to a method for recombinantly producing such a fusion protein. Finally, the present invention also provides a pharmaceutical composition comprising such a fusion protein, a nucleic acid molecule, a vector, infectious viral particles and a host cell as well as the therapeutic use thereof.

16 Claims, 10 Drawing Sheets

OTHER PUBLICATIONS

Koyama, Fumikazu et al., "*Combined suicide gene therapy for human colon cancer cells using adenovirus-mediated transfer of Escherichia coli cytosine deaminase gene and Escherichia coli uracil phosphoribosyltransferase gene with 5-fluorocytosine*," 7(7) Cancer Gene Therapy 1015-1022 (2000).

Ma, Averil et al., "*The Pleiotropic Functions of Interleukin 15: Not So Interleukin 2-like After All*," 191(5) Journal of Experimental Medicine 753-755 (Mar. 6, 2000).

Micallef, Mark et al., "In vivo *antitumor effects of murine interferon-γ-inducing factor/interleukin-18 in mice bearing syngeneic Meth A sarcoma malignant ascites*," 43 Cancer Immunol Immunother 361-367 (1997).

Miller, Patrice et al., "*Intratumoral Administration of Adenoviral Interleukin 7 Gene-Modified Dendritic Cells Augments Specific Antitumor Immunity and Achieves Tumor Eradication*," 11 Human Gene Therapy 53-65 (Jan. 2000).

Nakanishi, Kenji et al., "*Interleukin-18 Regulates Both TH1 and TH2 Responses*", 19 Annu. Rev. Immunol. 423-474 (2001).

Osaki, T. et al., "*Potent antitumor effects mediated by local expression of the mature form of the interferon-γ inducing factor, interleukin-18* (IL-18)," 6 Gene Therapy 808-815 (1999).

Osaki, Tadashi et al., "*IFN-γ-Inducing Factor/IL-18 Administration Mediates IFN-γ- and IL-12-Independent Antitumor Effects*," 160 The Journal of Immunology 1742-1749, (1998).

Ozdemir, Oner et al., "*Interleukin-2 and Interleukin-15 Combination Induces Lymphokine Activated Killer Cells with Higher Perforin and Granzyme B Expression Patterns and Superior Cytotoxic Response Against Human Leukemia Cells*," 100(11) Blood (Nov. 16, 2002) and Abstract No. 1827, 44th Annual Meeting of the American Society of Hematology; Philadelphia, PA, USA (Dec. 6-10, 2002).

Rock, F. et al., "*Overexpression and structure—function analysis of a bioengineered IL-2/IL-6 chimeric lymphokine*," 5(6) Protein Engineering 583-591 (Sep. 1992).

Shanafelt, Armen et al., "*A T-cell-selective interleukin 2 mutein exhibits potent antitumor activity and is well tolerated* in vivo," 18(11) Nature Biotechnology 1197-1202, (Nov. 2000).

Slos, Philippe et al., "*Immunotherapy of established tumors in mice by intratumoral injection of an adenovirus vector harboring the human IL-2 cDNA: Induction of CD8$^+$ T-cell immunity and NK activity*," 8(5) Cancer Gene Therapy 321-332 (2001).

Son, Young-Ik et al., "*Interleukin-18 (IL-18) Synergizes with IL-2 to Enhance Cytotoxicity, Interferon-γ Production, and Expansion of Natural Killer Cells*," 61(3) Cancer Research 884-888 (Feb. 1, 2001).

Vaquez, Nancy et al., "*Interleukin-15 Augments Superoxide Production and Microbicidal Activity of Human Monocytes against Candida albicans*,"66(1) Infection and Immunity 145-150 (Jan. 1, 1998).

Wang, Q. et al., "*Intratumoral IL-18 gene transfer improves therapeutic efficacy of antibody-targeted superantigen in established murine melanoma*," 8(7) Gene Therapy 542-550 (Apr. 2001).

Wigginton, Jon et al., "*Synergistic Engagement of an Ineffective Endogenous Anti-Tumor Immune Response and Induction of IFN-γ and FAS-Ligand-Dependent Tumor Eradication by Combined Administration of IL-18 and IL-2*," 169(8) The Journal of Immunology 4467-4474 (Oct. 15, 2002).

SEQUENCE LISTING

<160> NUMBER OF SEQ ID NOS: 59

<210> SEQ ID NO 1
<211> LENGTH: 345
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-7/linker/human IL-2"

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys

```
                    20                  25                  30
Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His Gly Gly Gly Gly Ser Gly Gly Gly Gly Ser Gly Gly Gly Gly Ser
            180                 185                 190

Met Tyr Arg Met Gln Leu Leu Ser Cys Ile Ala Leu Ser Leu Ala Leu
        195                 200                 205

Val Thr Asn Ser Ala Pro Thr Ser Ser Ser Thr Lys Lys Thr Gln Leu
    210                 215                 220

Gln Leu Glu His Leu Leu Leu Asp Leu Gln Met Ile Leu Asn Gly Ile
225                 230                 235                 240

Asn Asn Tyr Lys Asn Pro Lys Leu Thr Arg Met Leu Thr Phe Lys Phe
                245                 250                 255

Tyr Met Pro Lys Lys Ala Thr Glu Leu Lys His Leu Gln Cys Leu Glu
            260                 265                 270

Glu Glu Leu Lys Pro Leu Glu Glu Val Leu Asn Leu Ala Gln Ser Lys
        275                 280                 285

Asn Phe His Leu Arg Pro Arg Asp Leu Ile Ser Asn Ile Asn Val Ile
    290                 295                 300

Val Leu Glu Leu Lys Gly Ser Glu Thr Thr Phe Met Cys Glu Tyr Ala
305                 310                 315                 320

Asp Glu Thr Ala Thr Ile Val Glu Phe Leu Asn Arg Trp Ile Thr Phe
                325                 330                 335

Cys Gln Ser Ile Ile Ser Thr Leu Thr
            340                 345

<210> SEQ ID NO 2
<211> LENGTH: 333
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL7/linker/murine IL-2"

<400> SEQUENCE: 2

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30
```

```
Glu Gly Lys Ala Tyr Glu Ser Val Leu Met Ile Ser Ile Asp Glu Leu
             35                  40                  45

Asp Lys Met Thr Gly Thr Asp Ser Asn Cys Pro Asn Asn Glu Pro Asn
 50                  55                  60

Phe Phe Arg Lys His Val Cys Asp Asp Thr Lys Glu Ala Ala Phe Leu
 65                  70                  75                  80

Asn Arg Ala Ala Arg Lys Leu Lys Gln Phe Leu Lys Met Asn Ile Ser
                 85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
            115                 120                 125

Lys Asn Asp Ala Cys Phe Leu Lys Arg Leu Leu Arg Glu Ile Lys Thr
130                 135                 140

Cys Trp Asn Lys Ile Leu Lys Gly Ser Ile Gly Gly Gly Ser Gly
145                 150                 155                 160

Gly Gly Gly Ser Met Tyr Ser Met Gln Leu Ala Ser Cys Val Thr Leu
                165                 170                 175

Thr Leu Val Leu Val Asn Ser Ala Pro Thr Ser Ser Ser Thr Ser
            180                 185                 190

Ser Ser Thr Ala Glu Ala Gln Gln Gln Gln Gln Gln Gln Gln Gln Gln
            195                 200                 205

Gln Gln His Leu Glu Gln Leu Leu Met Asp Leu Gln Glu Leu Leu Ser
            210                 215                 220

Arg Met Glu Asn Tyr Arg Asn Leu Lys Leu Pro Arg Met Leu Thr Phe
225                 230                 235                 240

Lys Phe Tyr Leu Pro Lys Gln Ala Thr Glu Leu Lys Asp Leu Gln Cys
                245                 250                 255

Leu Glu Asp Glu Leu Gly Pro Leu Arg His Val Leu Asp Leu Thr Gln
            260                 265                 270

Ser Lys Ser Phe Gln Leu Glu Asp Ala Glu Asn Phe Ile Ser Asn Ile
            275                 280                 285

Arg Val Thr Val Val Lys Leu Lys Gly Ser Asp Asn Thr Phe Glu Cys
290                 295                 300

Gln Phe Asp Asp Glu Ser Ala Thr Val Val Asp Phe Leu Arg Arg Trp
305                 310                 315                 320

Ile Ala Phe Cys Gln Ser Ile Ile Ser Thr Ser Pro Gln
                325                 330

<210> SEQ ID NO 3
<211> LENGTH: 330
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-2/linker/human IL-15"

<400> SEQUENCE: 3

Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
             20                  25                  30

Gln Leu Glu His Leu Leu Leu Asp Leu Gln Met Ile Leu Asn Gly Ile
             35                  40                  45

Asn Asn Tyr Lys Asn Pro Lys Leu Thr Arg Met Leu Thr Phe Lys Phe
 50                  55                  60
```

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Met Arg Ile Ser Lys Pro His Leu
                165                 170                 175

Arg Ser Ile Ser Ile Gln Cys Tyr Leu Cys Leu Leu Leu Asn Ser His
            180                 185                 190

Phe Leu Thr Glu Ala Gly Ile His Val Phe Ile Leu Gly Cys Phe Ser
        195                 200                 205

Ala Gly Leu Pro Lys Thr Glu Ala Asn Trp Val Asn Val Ile Ser Asp
    210                 215                 220

Leu Lys Lys Ile Glu Asp Leu Ile Gln Ser Met His Ile Asp Ala Thr
225                 230                 235                 240

Leu Tyr Thr Glu Ser Asp Val His Pro Ser Cys Lys Val Thr Ala Met
                245                 250                 255

Lys Cys Phe Leu Leu Glu Leu Gln Val Ile Ser Leu Glu Ser Gly Asp
            260                 265                 270

Ala Ser Ile His Asp Thr Val Glu Asn Leu Ile Ile Leu Ala Asn Asn
        275                 280                 285

Ser Leu Ser Ser Asn Gly Asn Val Thr Glu Ser Gly Cys Lys Glu Cys
    290                 295                 300

Glu Glu Leu Glu Glu Lys Asn Ile Lys Glu Phe Leu Gln Ser Phe Val
305                 310                 315                 320

His Ile Val Gln Met Phe Ile Asn Thr Ser
                325                 330

<210> SEQ ID NO 4
<211> LENGTH: 330
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-15/linker/human IL-2"

<400> SEQUENCE: 4

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln

```
              85                  90                  95
Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
            130                 135                 140

Lys Glu Phe Leu Gln Ser Phe Val His Ile Val Gln Met Phe Ile Asn
145                 150                 155                 160

Thr Ser Gly Gly Gly Gly Ser Gly Gly Gly Gly Ser Gly Gly Gly Gly
                165                 170                 175

Ser Met Tyr Arg Met Gln Leu Leu Ser Cys Ile Ala Leu Ser Leu Ala
                180                 185                 190

Leu Val Thr Asn Ser Ala Pro Thr Ser Ser Ser Thr Lys Lys Thr Gln
            195                 200                 205

Leu Gln Leu Glu His Leu Leu Leu Asp Leu Gln Met Ile Leu Asn Gly
            210                 215                 220

Ile Asn Asn Tyr Lys Asn Pro Lys Leu Thr Arg Met Leu Thr Phe Lys
225                 230                 235                 240

Phe Tyr Met Pro Lys Lys Ala Thr Glu Leu Lys His Leu Gln Cys Leu
                245                 250                 255

Glu Glu Glu Leu Lys Pro Leu Glu Glu Val Leu Asn Leu Ala Gln Ser
                260                 265                 270

Lys Asn Phe His Leu Arg Pro Arg Asp Leu Ile Ser Asn Ile Asn Val
            275                 280                 285

Ile Val Leu Glu Leu Lys Gly Ser Glu Thr Thr Phe Met Cys Glu Tyr
290                 295                 300

Ala Asp Glu Thr Ala Thr Ile Val Glu Phe Leu Asn Arg Trp Ile Thr
305                 310                 315                 320

Phe Cys Gln Ser Ile Ile Ser Thr Leu Thr
                325                 330

<210> SEQ ID NO 5
<211> LENGTH: 350
<212> TYPE: PRT
<213> ORGANISM: artificial sequence
<220> FEATURE:
<221> NAME/KEY: source
<223> OTHER INFORMATION: /note= "Description of artificial sequence:
      fusion signal IL-2/human IL-15/linker/human IL-2"

<400> SEQUENCE: 5

Met Tyr Arg Met Gln Leu Leu Ser Cys Ile Ala Leu Ser Leu Ala Leu
1               5                   10                  15

Val Thr Asn Ser Met Arg Ile Ser Lys Pro His Leu Arg Ser Ile Ser
            20                  25                  30

Ile Gln Cys Tyr Leu Cys Leu Leu Leu Asn Ser His Phe Leu Thr Glu
        35                  40                  45

Ala Gly Ile His Val Phe Ile Leu Gly Cys Phe Ser Ala Gly Leu Pro
    50                  55                  60

Lys Thr Glu Ala Asn Trp Val Asn Val Ile Ser Asp Leu Lys Lys Ile
65                  70                  75                  80

Glu Asp Leu Ile Gln Ser Met His Ile Asp Ala Thr Leu Tyr Thr Glu
                85                  90                  95

Ser Asp Val His Pro Ser Cys Lys Val Thr Ala Met Lys Cys Phe Leu
            100                 105                 110
```

```
Leu Glu Leu Gln Val Ile Ser Leu Glu Ser Gly Asp Ala Ser Ile His
        115                 120                 125
Asp Thr Val Glu Asn Leu Ile Ile Leu Ala Asn Asn Ser Leu Ser Ser
130                 135                 140
Asn Gly Asn Val Thr Glu Ser Gly Cys Lys Glu Cys Glu Glu Leu Glu
145                 150                 155                 160
Glu Lys Asn Ile Lys Glu Phe Leu Gln Ser Phe Val His Ile Val Gln
                165                 170                 175
Met Phe Ile Asn Thr Ser Gly Gly Gly Ser Gly Gly Gly Gly Ser
        180                 185                 190
Gly Gly Gly Gly Ser Met Tyr Arg Met Gln Leu Leu Ser Cys Ile Ala
        195                 200                 205
Leu Ser Leu Ala Leu Val Thr Asn Ser Ala Pro Thr Ser Ser Ser Thr
210                 215                 220
Lys Lys Thr Gln Leu Gln Leu Glu His Leu Leu Leu Asp Leu Gln Met
225                 230                 235                 240
Ile Leu Asn Gly Ile Asn Asn Tyr Lys Asn Pro Lys Leu Thr Arg Met
                245                 250                 255
Leu Thr Phe Lys Phe Tyr Met Pro Lys Lys Ala Thr Glu Leu Lys His
        260                 265                 270
Leu Gln Cys Leu Glu Glu Glu Leu Lys Pro Leu Glu Glu Val Leu Asn
        275                 280                 285
Leu Ala Gln Ser Lys Asn Phe His Leu Arg Pro Arg Asp Leu Ile Ser
290                 295                 300
Asn Ile Asn Val Ile Val Leu Glu Leu Lys Gly Ser Glu Thr Thr Phe
305                 310                 315                 320
Met Cys Glu Tyr Ala Asp Glu Thr Ala Thr Ile Val Glu Phe Leu Asn
                325                 330                 335
Arg Trp Ile Thr Phe Cys Gln Ser Ile Ile Ser Thr Leu Thr
        340                 345                 350

<210> SEQ ID NO 6
<211> LENGTH: 324
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-2/linker/murine IL-15"

<400> SEQUENCE: 6

Met Tyr Ser Met Gln Leu Ala Ser Cys Val Thr Leu Thr Leu Val Leu
1               5                   10                  15
Leu Val Asn Ser Ala Pro Thr Ser Ser Ser Thr Ser Ser Ser Thr Ala
                20                  25                  30
Glu Ala Gln Gln Gln Gln Gln Gln Gln Gln Gln Gln Gln His Leu
        35                  40                  45
Glu Gln Leu Leu Met Asp Leu Gln Glu Leu Leu Ser Arg Met Glu Asn
50                  55                  60
Tyr Arg Asn Leu Lys Leu Pro Arg Met Leu Thr Phe Lys Phe Tyr Leu
65                  70                  75                  80
Pro Lys Gln Ala Thr Glu Leu Lys Asp Leu Gln Cys Leu Glu Asp Glu
                85                  90                  95
Leu Gly Pro Leu Arg His Val Leu Asp Leu Thr Gln Ser Lys Ser Phe
        100                 105                 110
Gln Leu Glu Asp Ala Glu Asn Phe Ile Ser Asn Ile Arg Val Thr Val
        115                 120                 125
```

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly
                165                 170                 175

Gly Gly Ser Met Tyr Ser Met Gln Leu Ala Ser Cys Val Thr Leu Thr
            180                 185                 190

Leu Val Leu Leu Val Asn Ser Ala Gly Ala Asn Trp Ile Asp Val Arg
        195                 200                 205

Tyr Asp Leu Glu Lys Ile Glu Ser Leu Ile Gln Ser Ile His Ile Asp
    210                 215                 220

Thr Thr Leu Tyr Thr Asp Ser Asp Phe His Pro Ser Cys Lys Val Thr
225                 230                 235                 240

Ala Met Asn Cys Phe Leu Leu Glu Leu Gln Val Ile Leu His Glu Tyr
                245                 250                 255

Ser Asn Met Thr Leu Asn Glu Thr Val Arg Asn Val Leu Tyr Leu Ala
            260                 265                 270

Asn Ser Thr Leu Ser Ser Asn Lys Asn Val Ala Glu Ser Gly Cys Lys
        275                 280                 285

Glu Cys Glu Glu Leu Glu Glu Lys Thr Phe Thr Glu Phe Leu Gln Ser
    290                 295                 300

Phe Ile Arg Ile Val Gln Met Phe Ile Asn Thr Ser Asp Tyr Lys Asp
305                 310                 315                 320

Asp Asp Asp Lys

<210> SEQ ID NO 7
<211> LENGTH: 324
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-15/linker/murine IL-2"

<400> SEQUENCE: 7

Met Tyr Ser Met Gln Leu Ala Ser Cys Val Thr Leu Thr Leu Val Leu
1               5                   10                  15

Leu Val Asn Ser Ala Gly Ala Asn Trp Ile Asp Val Arg Tyr Asp Leu
            20                  25                  30

Glu Lys Ile Glu Ser Leu Ile Gln Ser Ile His Ile Asp Thr Thr Leu
        35                  40                  45

Tyr Thr Asp Ser Asp Phe His Pro Ser Cys Lys Val Thr Ala Met Asn
    50                  55                  60

Cys Phe Leu Leu Glu Leu Gln Val Ile Leu His Glu Tyr Ser Asn Met
65                  70                  75                  80

Thr Leu Asn Glu Thr Val Arg Asn Val Leu Tyr Leu Ala Asn Ser Thr
                85                  90                  95

Leu Ser Ser Asn Lys Asn Val Ala Glu Ser Gly Cys Lys Glu Cys Glu
            100                 105                 110

Glu Leu Glu Glu Lys Thr Phe Thr Glu Phe Leu Gln Ser Phe Ile Arg
        115                 120                 125

Ile Val Gln Met Phe Ile Asn Thr Ser Asp Tyr Lys Asp Asp Asp Asp
    130                 135                 140

Lys Gly Gly Gly Gly Ser Gly Gly Gly Gly Ser Met Tyr Ser Met Gln
145                 150                 155                 160

```
Leu Ala Ser Cys Val Thr Leu Thr Leu Val Leu Leu Val Asn Ser Ala
                165                 170                 175

Pro Thr Ser Ser Thr Ser Ser Thr Ala Glu Ala Gln Gln Gln
            180                 185                 190

Gln Gln Gln Gln Gln Gln Gln Gln His Leu Glu Gln Leu Leu Met
            195                 200                 205

Asp Leu Gln Glu Leu Leu Ser Arg Met Glu Asn Tyr Arg Asn Leu Lys
    210                 215                 220

Leu Pro Arg Met Leu Thr Phe Lys Phe Tyr Leu Pro Lys Gln Ala Thr
225                 230                 235                 240

Glu Leu Lys Asp Leu Gln Cys Leu Glu Asp Glu Leu Gly Pro Leu Arg
                245                 250                 255

His Val Leu Asp Leu Thr Gln Ser Lys Ser Phe Gln Leu Glu Asp Ala
                260                 265                 270

Glu Asn Phe Ile Ser Asn Ile Arg Val Thr Val Val Lys Leu Lys Gly
                275                 280                 285

Ser Asp Asn Thr Phe Glu Cys Gln Phe Asp Asp Glu Ser Ala Thr Val
    290                 295                 300

Val Asp Phe Leu Arg Arg Trp Ile Ala Phe Cys Gln Ser Ile Ile Ser
305                 310                 315                 320

Thr Ser Pro Gln

<210> SEQ ID NO 8
<211> LENGTH: 361
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-2/linker/human pro IL-18"

<400> SEQUENCE: 8

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr Gly Gly Gly Gly Ser Gly Gly
145                 150                 155                 160

Gly Gly Ser Gly Gly Gly Ser Met Ala Ala Glu Pro Val Glu Asp
            165                 170                 175

Asn Cys Ile Asn Phe Val Ala Met Lys Phe Ile Asp Asn Thr Leu Tyr
            180                 185                 190
```

```
Phe Ile Ala Glu Asp Asp Glu Asn Leu Glu Ser Asp Tyr Phe Gly Lys
            195                 200                 205
Leu Glu Ser Lys Leu Ser Val Ile Arg Asn Leu Asn Asp Gln Val Leu
            210                 215                 220
Phe Ile Asp Gln Gly Asn Arg Pro Leu Phe Glu Asp Met Thr Asp Ser
225                 230                 235                 240
Asp Cys Arg Asp Asn Ala Pro Arg Thr Ile Phe Ile Ile Ser Met Tyr
                245                 250                 255
Lys Asp Ser Gln Pro Arg Gly Met Ala Val Thr Ile Ser Val Lys Cys
            260                 265                 270
Glu Lys Ile Ser Thr Leu Ser Cys Glu Asn Lys Ile Ile Ser Phe Lys
            275                 280                 285
Glu Met Asn Pro Pro Asp Asn Ile Lys Asp Thr Lys Ser Asp Ile Ile
            290                 295                 300
Phe Phe Gln Arg Ser Val Pro Gly His Asp Asn Lys Met Gln Phe Glu
305                 310                 315                 320
Ser Ser Ser Tyr Glu Gly Tyr Phe Leu Ala Cys Glu Lys Glu Arg Asp
                325                 330                 335
Leu Phe Lys Leu Ile Leu Lys Lys Glu Asp Glu Leu Gly Asp Arg Ser
            340                 345                 350
Ile Met Phe Thr Val Gln Asn Glu Asp
            355                 360

<210> SEQ ID NO 9
<211> LENGTH: 361
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-2/linker/ human pro IL-18 K89A"

<400> SEQUENCE: 9

Met Tyr Arg Met Gln Leu Leu Ser Cys Ile Ala Leu Ser Leu Ala Leu
1               5                   10                  15
Val Thr Asn Ser Ala Pro Thr Ser Ser Ser Thr Lys Lys Thr Gln Leu
            20                  25                  30
Gln Leu Glu His Leu Leu Leu Asp Leu Gln Met Ile Leu Asn Gly Ile
        35                  40                  45
Asn Asn Tyr Lys Asn Pro Lys Leu Thr Arg Met Leu Thr Phe Lys Phe
    50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
            85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
            115                 120                 125
Asp Glu Thr Ala Thr Ile Val Glu Phe Leu Asn Arg Trp Ile Thr Phe
            130                 135                 140
Cys Gln Ser Ile Ile Ser Thr Leu Thr Gly Gly Gly Ser Gly Gly Gly
145                 150                 155                 160
Gly Gly Ser Gly Gly Gly Ser Met Ala Ala Glu Pro Val Glu Asp
                165                 170                 175
Asn Cys Ile Asn Phe Val Ala Met Lys Phe Ile Asp Asn Thr Leu Tyr
```

```
                    180                 185                 190
Phe Ile Ala Glu Asp Asp Glu Asn Leu Glu Ser Asp Tyr Phe Gly Lys
            195                 200                 205

Leu Glu Ser Lys Leu Ser Val Ile Arg Asn Leu Asn Asp Gln Val Leu
            210                 215                 220

Phe Ile Asp Gln Gly Asn Arg Pro Leu Phe Glu Asp Met Thr Asp Ser
225                 230                 235                 240

Asp Cys Arg Asp Asn Ala Pro Arg Thr Ile Phe Ile Ile Ser Met Tyr
                245                 250                 255

Ala Asp Ser Gln Pro Arg Gly Met Ala Val Thr Ile Ser Val Lys Cys
            260                 265                 270

Glu Lys Ile Ser Thr Leu Ser Cys Glu Asn Lys Ile Ile Ser Phe Lys
            275                 280                 285

Glu Met Asn Pro Pro Asp Asn Ile Lys Asp Thr Lys Ser Asp Ile Ile
            290                 295                 300

Phe Phe Gln Arg Ser Val Pro Gly His Asp Asn Lys Met Gln Phe Glu
305                 310                 315                 320

Ser Ser Ser Tyr Glu Gly Tyr Phe Leu Ala Cys Glu Lys Glu Arg Asp
                325                 330                 335

Leu Phe Lys Leu Ile Leu Lys Lys Glu Asp Glu Leu Gly Asp Arg Ser
            340                 345                 350

Ile Met Phe Thr Val Gln Asn Glu Asp
            355                 360

<210> SEQ ID NO 10
<211> LENGTH: 325
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-2/linker/mature human IL-18"

<400> SEQUENCE: 10

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Tyr Phe Gly Lys Leu Glu Ser Lys
                165                 170                 175
```

```
Leu Ser Val Ile Arg Asn Leu Asn Asp Gln Val Leu Phe Ile Asp Gln
            180                 185                 190

Gly Asn Arg Pro Leu Phe Glu Asp Met Thr Asp Ser Asp Cys Arg Asp
        195                 200                 205

Asn Ala Pro Arg Thr Ile Phe Ile Ile Ser Met Tyr Lys Asp Ser Gln
    210                 215                 220

Pro Arg Gly Met Ala Val Thr Ile Ser Val Lys Cys Glu Lys Ile Ser
225                 230                 235                 240

Thr Leu Ser Cys Glu Asn Lys Ile Ile Ser Phe Lys Glu Met Asn Pro
            245                 250                 255

Pro Asp Asn Ile Lys Asp Thr Lys Ser Asp Ile Ile Phe Phe Gln Arg
        260                 265                 270

Ser Val Pro Gly His Asp Asn Lys Met Gln Phe Glu Ser Ser Ser Tyr
    275                 280                 285

Glu Gly Tyr Phe Leu Ala Cys Glu Lys Glu Arg Asp Leu Phe Lys Leu
        290                 295                 300

Ile Leu Lys Lys Glu Asp Glu Leu Gly Asp Arg Ser Ile Met Phe Thr
305                 310                 315                 320

Val Gln Asn Glu Asp
            325

<210> SEQ ID NO 11
<211> LENGTH: 325
<212> TYPE: PRT
<213> ORGANISM: artificial sequence
<220> FEATURE:
<221> NAME/KEY: source
<223> OTHER INFORMATION: /note= "Description of artificial sequence:
      fusion human IL-2/linker/ mature human IL-18 K89A"

<400> SEQUENCE: 11

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
            85                  90                  95

Asn Phe His Leu Arg Pro Arg Asp Leu Ile Ser Asn Ile Asn Val Ile
        100                 105                 110

Val Leu Glu Leu Lys Gly Ser Glu Thr Thr Phe Met Cys Glu Tyr Ala
    115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Tyr Phe Gly Lys Leu Glu Ser Lys
            165                 170                 175

Leu Ser Val Ile Arg Asn Leu Asn Asp Gln Val Leu Phe Ile Asp Gln
        180                 185                 190

Gly Asn Arg Pro Leu Phe Glu Asp Met Thr Asp Ser Asp Cys Arg Asp
    195                 200                 205
```

```
Asn Ala Pro Arg Thr Ile Phe Ile Ile Ser Met Tyr Ala Asp Ser Gln
    210                 215                 220

Pro Arg Gly Met Ala Val Thr Ile Ser Val Lys Cys Glu Lys Ile Ser
225                 230                 235                 240

Thr Leu Ser Cys Glu Asn Lys Ile Ile Ser Phe Lys Glu Met Asn Pro
                245                 250                 255

Pro Asp Asn Ile Lys Asp Thr Lys Ser Asp Ile Ile Phe Phe Gln Arg
                260                 265                 270

Ser Val Pro Gly His Asp Asn Lys Met Gln Phe Glu Ser Ser Ser Tyr
                275                 280                 285

Glu Gly Tyr Phe Leu Ala Cys Glu Lys Glu Arg Asp Leu Phe Lys Leu
                290                 295                 300

Ile Leu Lys Lys Glu Asp Glu Leu Gly Asp Arg Ser Ile Met Phe Thr
305                 310                 315                 320

Val Gln Asn Glu Asp
                325

<210> SEQ ID NO 12
<211> LENGTH: 371
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-2/linker/murine pro-IL-18"

<400> SEQUENCE: 12

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln Gln His Leu
                35                  40                  45

Glu Gln Leu Leu Met Asp Leu Gln Glu Leu Leu Ser Arg Met Glu Asn
            50                  55                  60

Tyr Arg Asn Leu Lys Leu Pro Arg Met Leu Thr Phe Lys Phe Tyr Leu
65              70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
                100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
            130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly
                165                 170                 175

Gly Gly Ser Met Ala Ala Met Ser Glu Asp Ser Cys Val Asn Phe Lys
                180                 185                 190

Glu Met Met Phe Ile Asp Asn Thr Leu Tyr Phe Ile Pro Glu Glu Asn
            195                 200                 205

Gly Asp Leu Glu Ser Asp Asn Phe Gly Arg Leu His Cys Thr Thr Ala
            210                 215                 220

Val Ile Arg Asn Ile Asn Asp Gln Val Leu Phe Val Asp Lys Arg Gln
```

-continued

```
                225                 230                 235                 240
Pro Val Phe Glu Asp Met Thr Asp Ile Asp Gln Ser Ala Ser Glu Pro
                245                 250                 255

Gln Thr Arg Leu Ile Ile Tyr Met Tyr Lys Asp Ser Glu Val Arg Gly
                260                 265                 270

Leu Ala Val Thr Leu Ser Val Lys Asp Ser Lys Met Ser Thr Leu Ser
                275                 280                 285

Cys Lys Asn Lys Ile Ile Ser Phe Glu Glu Met Asp Pro Pro Glu Asn
                290                 295                 300

Ile Asp Ile Gln Ser Asp Leu Ile Phe Phe Gln Lys Arg Val Pro
305                 310                 315                 320

Gly His Asn Lys Met Glu Phe Glu Ser Ser Leu Tyr Glu Gly His Phe
                325                 330                 335

Leu Ala Cys Gln Lys Glu Asp Asp Ala Phe Lys Leu Ile Leu Lys Lys
                340                 345                 350

Lys Asp Glu Asn Gly Asp Lys Ser Val Met Phe Thr Leu Thr Asn Leu
                355                 360                 365

His Gln Ser
    370

<210> SEQ ID NO 13
<211> LENGTH: 371
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-2/linker/murine pro IL-18 K89A"

<400> SEQUENCE: 13

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln Gln His Leu
                35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
                100                 105                 110

Gln Leu Glu Asp Ala Glu Asn Phe Ile Ser Asn Ile Arg Val Thr Val
                115                 120                 125

Val Lys Leu Lys Gly Ser Asp Asn Thr Phe Glu Cys Gln Phe Asp Asp
                130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly
                165                 170                 175

Gly Gly Ser Met Ala Ala Met Ser Glu Asp Ser Cys Val Asn Phe Lys
                180                 185                 190

Glu Met Met Phe Ile Asp Asn Thr Leu Tyr Phe Ile Pro Glu Glu Asn
                195                 200                 205
```

-continued

```
Gly Asp Leu Glu Ser Asp Asn Phe Gly Arg Leu His Cys Thr Thr Ala
            210                 215                 220

Val Ile Arg Asn Ile Asn Asp Gln Val Leu Phe Val Asp Lys Arg Gln
225                 230                 235                 240

Pro Val Phe Glu Asp Met Thr Asp Ile Asp Gln Ser Ala Ser Glu Pro
            245                 250                 255

Gln Thr Arg Leu Ile Ile Tyr Met Tyr Ala Asp Ser Glu Val Arg Gly
            260                 265                 270

Leu Ala Val Thr Leu Ser Val Lys Asp Ser Lys Met Ser Thr Leu Ser
            275                 280                 285

Cys Lys Asn Lys Ile Ile Ser Phe Glu Glu Met Asp Pro Pro Glu Asn
            290                 295                 300

Ile Asp Asp Ile Gln Ser Asp Leu Ile Phe Phe Gln Lys Arg Val Pro
305                 310                 315                 320

Gly His Asn Lys Met Glu Phe Glu Ser Ser Leu Tyr Glu Gly His Phe
            325                 330                 335

Leu Ala Cys Gln Lys Glu Asp Asp Ala Phe Lys Leu Ile Leu Lys Lys
            340                 345                 350

Lys Asp Glu Asn Gly Asp Lys Ser Val Met Phe Thr Leu Thr Asn Leu
            355                 360                 365

His Gln Ser
    370

<210> SEQ ID NO 14
<211> LENGTH: 336
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-2/linker/ mature murine IL-18"

<400> SEQUENCE: 14

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
            85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly
            165                 170                 175

Gly Gly Ser Asn Phe Gly Arg Leu His Cys Thr Thr Ala Val Ile Arg
            180                 185                 190
```

```
Asn Ile Asn Asp Gln Val Leu Phe Val Asp Lys Arg Gln Pro Val Phe
            195                 200                 205
Glu Asp Met Thr Asp Ile Asp Gln Ser Ala Ser Glu Pro Gln Thr Arg
            210                 215                 220
Leu Ile Ile Tyr Met Tyr Lys Asp Ser Glu Val Arg Gly Leu Ala Val
225                 230                 235                 240
Thr Leu Ser Val Lys Asp Ser Lys Met Ser Thr Leu Ser Cys Lys Asn
                245                 250                 255
Lys Ile Ile Ser Phe Glu Glu Met Asp Pro Pro Glu Asn Ile Asp Asp
                260                 265                 270
Ile Gln Ser Asp Leu Ile Phe Phe Gln Lys Arg Val Pro Gly His Asn
            275                 280                 285
Lys Met Glu Phe Glu Ser Ser Leu Tyr Glu Gly His Phe Leu Ala Cys
            290                 295                 300
Gln Lys Glu Asp Asp Ala Phe Lys Leu Ile Leu Lys Lys Lys Asp Glu
305                 310                 315                 320
Asn Gly Asp Lys Ser Val Met Phe Thr Leu Thr Asn Leu His Gln Ser
                325                 330                 335

<210> SEQ ID NO 15
<211> LENGTH: 336
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-2/linker/mature murine IL-18 K89A"

<400> SEQUENCE: 15

Met Tyr Ser Met Gln Leu Ala Ser Cys Val Thr Leu Thr Leu Val Leu
1               5                   10                  15
Leu Val Asn Ser Ala Pro Thr Ser Ser Ser Thr Ser Ser Ser Thr Ala
                20                  25                  30
Glu Ala Gln Gln Gln Gln Gln Gln Gln Gln Gln Gln Gln His Leu
            35                  40                  45
Glu Gln Leu Leu Met Asp Leu Gln Glu Leu Leu Ser Arg Met Glu Asn
            50                  55                  60
Tyr Arg Asn Leu Lys Leu Pro Arg Met Leu Thr Phe Lys Phe Tyr Leu
65                  70                  75                  80
Pro Lys Gln Ala Thr Glu Leu Lys Asp Leu Gln Cys Leu Glu Asp Glu
                85                  90                  95
Leu Gly Pro Leu Arg His Val Leu Asp Leu Thr Gln Ser Lys Ser Phe
                100                 105                 110
Gln Leu Glu Asp Ala Glu Asn Phe Ile Ser Asn Ile Arg Val Thr Val
            115                 120                 125
Val Lys Leu Lys Gly Ser Asp Asn Thr Phe Glu Cys Gln Phe Asp Asp
130                 135                 140
Glu Ser Ala Thr Val Val Asp Phe Leu Arg Arg Trp Ile Ala Phe Cys
145                 150                 155                 160
Gln Ser Ile Ile Ser Thr Ser Pro Gln Gly Gly Gly Ser Gly Gly
            165                 170                 175
Gly Gly Ser Asn Phe Gly Arg Leu His Cys Thr Thr Ala Val Ile Arg
                180                 185                 190
Asn Ile Asn Asp Gln Val Leu Phe Val Asp Lys Arg Gln Pro Val Phe
            195                 200                 205
Glu Asp Met Thr Asp Ile Asp Gln Ser Ala Ser Glu Pro Gln Thr Arg
```

```
           210                 215                  220
Leu Ile Ile Tyr Met Tyr Ala Asp Ser Glu Val Arg Gly Leu Ala Val
225                 230                 235                 240

Thr Leu Ser Val Lys Asp Ser Lys Met Ser Thr Leu Ser Cys Lys Asn
                    245                 250                 255

Lys Ile Ile Ser Phe Glu Glu Met Asp Pro Pro Glu Asn Ile Asp Asp
                260                 265                 270

Ile Gln Ser Asp Leu Ile Phe Phe Gln Lys Arg Val Pro Gly His Asn
            275                 280                 285

Lys Met Glu Phe Glu Ser Ser Leu Tyr Glu Gly His Phe Leu Ala Cys
        290                 295                 300

Gln Lys Glu Asp Asp Ala Phe Lys Leu Ile Leu Lys Lys Asp Glu
305                 310                 315                 320

Asn Gly Asp Lys Ser Val Met Phe Thr Leu Thr Asn Leu His Gln Ser
                325                 330                 335
```

<210> SEQ ID NO 16
<211> LENGTH: 347
<212> TYPE: PRT
<213> ORGANISM: artificial sequence
<220> FEATURE:
<221> NAME/KEY: source
<223> OTHER INFORMATION: /note= "Description of artificial sequence: fusion human IL-21/linker/ human IL-2"

<400> SEQUENCE: 16

```
Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
                20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
                100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
        130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile Gly Gly Gly Ser Gly Gly Gly Ser Gly Gly Gly
                180                 185                 190

Gly Ser Met Tyr Arg Met Gln Leu Leu Ser Cys Ile Ala Leu Ser Leu
            195                 200                 205

Ala Leu Val Thr Asn Ser Ala Pro Thr Ser Ser Thr Lys Lys Thr
        210                 215                 220

Gln Leu Gln Leu Glu His Leu Leu Leu Asp Leu Gln Met Ile Leu Asn
225                 230                 235                 240
```

```
Gly Ile Asn Asn Tyr Lys Asn Pro Lys Leu Thr Arg Met Leu Thr Phe
            245                 250                 255

Lys Phe Tyr Met Pro Lys Lys Ala Thr Glu Leu Lys His Leu Gln Cys
            260                 265                 270

Leu Glu Glu Glu Leu Lys Pro Leu Glu Val Leu Asn Leu Ala Gln
            275                 280                 285

Ser Lys Asn Phe His Leu Arg Pro Arg Asp Leu Ile Ser Asn Ile Asn
            290                 295                 300

Val Ile Val Leu Glu Leu Lys Gly Ser Glu Thr Thr Phe Met Cys Glu
305                 310                 315                 320

Tyr Ala Asp Glu Thr Ala Thr Ile Val Glu Phe Leu Asn Arg Trp Ile
            325                 330                 335

Thr Phe Cys Gln Ser Ile Ile Ser Thr Leu Thr
            340                 345

<210> SEQ ID NO 17
<211> LENGTH: 325
<212> TYPE: PRT
<213> ORGANISM: artificial sequence
<220> FEATURE:
<221> NAME/KEY: source
<223> OTHER INFORMATION: /note= "Description of artificial sequence:
      fusion murine IL-21/linker/murine IL-2"

<400> SEQUENCE: 17

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
            35                  40                  45

Leu Asp Pro Glu Leu Leu Ser Ala Pro Gln Asp Val Lys Gly His Cys
        50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
            85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
            115                 120                 125

Phe Leu Glu Arg Leu Lys Trp Leu Leu Gln Lys Met Ile His Gln His
            130                 135                 140

Leu Ser Gly Gly Gly Gly Ser Gly Gly Gly Gly Ser Met Tyr Ser Met
145                 150                 155                 160

Gln Leu Ala Ser Cys Val Thr Leu Thr Leu Val Leu Val Asn Ser
            165                 170                 175

Ala Pro Thr Ser Ser Ser Thr Ser Ser Ser Thr Ala Glu Ala Gln Gln
            180                 185                 190

Gln Gln Gln Gln Gln Gln Gln Gln Gln His Leu Glu Gln Leu Leu
            195                 200                 205

Met Asp Leu Gln Glu Leu Leu Ser Arg Met Glu Asn Tyr Arg Asn Leu
210                 215                 220

Lys Leu Pro Arg Met Leu Thr Phe Lys Phe Tyr Leu Pro Lys Gln Ala
225                 230                 235                 240

Thr Glu Leu Lys Asp Leu Gln Cys Leu Glu Asp Glu Leu Gly Pro Leu
            245                 250                 255
```

Arg His Val Leu Asp Leu Thr Gln Ser Lys Ser Phe Gln Leu Glu Asp
            260                 265                 270

Ala Glu Asn Phe Ile Ser Asn Ile Arg Val Thr Val Val Lys Leu Lys
            275                 280                 285

Gly Ser Asp Asn Thr Phe Glu Cys Gln Phe Asp Asp Glu Ser Ala Thr
            290                 295                 300

Val Val Asp Phe Leu Arg Arg Trp Ile Ala Phe Cys Gln Ser Ile Ile
305                 310                 315                 320

Ser Thr Ser Pro Gln
            325

<210> SEQ ID NO 18
<211> LENGTH: 334
<212> TYPE: PRT
<213> ORGANISM: artificial sequence
<220> FEATURE:
<221> NAME/KEY: source
<223> OTHER INFORMATION: /note= "Description of artificial sequence:
      fusion human IFN-g/linker/human IL-2"

<400> SEQUENCE: 18

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln Gly Gly Gly Ser Gly Gly Gly Gly Ser
                165                 170                 175

Gly Gly Gly Gly Ser Met Tyr Arg Met Gln Leu Leu Ser Cys Ile Ala
            180                 185                 190

Leu Ser Leu Ala Leu Val Thr Asn Ser Ala Pro Thr Ser Ser Ser Thr
        195                 200                 205

Lys Lys Thr Gln Leu Gln Leu Glu His Leu Leu Leu Asp Leu Gln Met
    210                 215                 220

Ile Leu Asn Gly Ile Asn Asn Tyr Lys Asn Pro Lys Leu Thr Arg Met
225                 230                 235                 240

Leu Thr Phe Lys Phe Tyr Met Pro Lys Lys Ala Thr Glu Leu Lys His
                245                 250                 255

Leu Gln Cys Leu Glu Glu Glu Leu Lys Pro Leu Glu Glu Val Leu Asn
            260                 265                 270

Leu Ala Gln Ser Lys Asn Phe His Leu Arg Pro Arg Asp Leu Ile Ser

```
                    275                 280                 285

Asn Ile Asn Val Ile Val Leu Glu Leu Lys Gly Ser Glu Thr Thr Phe
            290                 295                 300

Met Cys Glu Tyr Ala Asp Glu Thr Ala Thr Ile Val Glu Phe Leu Asn
305                 310                 315                 320

Arg Trp Ile Thr Phe Cys Gln Ser Ile Ile Ser Thr Leu Thr
                325                 330

<210> SEQ ID NO 19
<211> LENGTH: 334
<212> TYPE: PRT
<213> ORGANISM: artificial sequence
<220> FEATURE:
<221> NAME/KEY: source
<223> OTHER INFORMATION: /note= "Description of artificial sequence:
      fusion murine IFN-g/linker/murine IL-2"

<400> SEQUENCE: 19

Met Asn Ala Thr His Cys Ile Leu Ala Leu Gln Leu Phe Leu Met Ala
1               5                   10                  15

Val Ser Gly Cys Tyr Cys His Gly Thr Val Ile Glu Ser Leu Glu Ser
            20                  25                  30

Leu Asn Asn Tyr Phe Asn Ser Ser Gly Ile Asp Val Glu Glu Lys Ser
        35                  40                  45

Leu Phe Leu Asp Ile Trp Arg Asn Trp Gln Lys Asp Gly Asp Met Lys
    50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
            100                 105                 110

Phe Met Ser Ile Ala Lys Phe Glu Val Asn Asn Pro Gln Val Gln Arg
        115                 120                 125

Gln Ala Phe Asn Glu Leu Ile Arg Val Val His Gln Leu Leu Pro Glu
    130                 135                 140

Ser Ser Leu Arg Lys Arg Lys Arg Ser Arg Cys Gly Gly Gly Gly Ser
145                 150                 155                 160

Gly Gly Gly Gly Ser Met Tyr Ser Met Gln Leu Ala Ser Cys Val Thr
                165                 170                 175

Leu Thr Leu Val Leu Leu Val Asn Ser Ala Pro Thr Ser Ser Ser Thr
            180                 185                 190

Ser Ser Ser Thr Ala Glu Ala Gln Gln Gln Gln Gln Gln Gln Gln Gln
        195                 200                 205

Gln Gln Gln His Leu Glu Gln Leu Leu Met Asp Leu Gln Glu Leu Leu
    210                 215                 220

Ser Arg Met Glu Asn Tyr Arg Asn Leu Lys Leu Pro Arg Met Leu Thr
225                 230                 235                 240

Phe Lys Phe Tyr Leu Pro Lys Gln Ala Thr Glu Leu Lys Asp Leu Gln
                245                 250                 255

Cys Leu Glu Asp Glu Leu Gly Pro Leu Arg His Val Leu Asp Leu Thr
            260                 265                 270

Gln Ser Lys Ser Phe Gln Leu Glu Asp Ala Glu Asn Phe Ile Ser Asn
        275                 280                 285

Ile Arg Val Thr Val Val Lys Leu Lys Gly Ser Asp Asn Thr Phe Glu
    290                 295                 300
```

```
Cys Gln Phe Asp Asp Glu Ser Ala Thr Val Val Asp Phe Leu Arg Arg
305                 310                 315                 320

Trp Ile Ala Phe Cys Gln Ser Ile Ile Ser Thr Ser Pro Gln
                325                 330
```

```
<210> SEQ ID NO 20
<211> LENGTH: 26
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning murine IL-2"

<400> SEQUENCE: 20
cggaattcca cagtgacctc aagtcc                                      26

<210> SEQ ID NO 21
<211> LENGTH: 24
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning murine IL-2"

<400> SEQUENCE: 21
ggggtacccc ttatgtgttg taag                                        24

<210> SEQ ID NO 22
<211> LENGTH: 34
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning variant N88G of murine IL-2"

<400> SEQUENCE: 22
gagaatttca tcagcggtat cagagtaact gttg                             34

<210> SEQ ID NO 23
<211> LENGTH: 34
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning variant N88G of murine IL-2"

<400> SEQUENCE: 23
caacagttac tctgataccg ctgatgaaat tctc                             34

<210> SEQ ID NO 24
<211> LENGTH: 34
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning variant N88R of murine IL-2"

<400> SEQUENCE: 24
gagaatttca tcagccgtat cagagtaact gttg                             34

<210> SEQ ID NO 25
<211> LENGTH: 34
<212> TYPE: DNA
```

```
<213> ORGANISM: artificial sequence
<220> FEATURE:
<221> NAME/KEY: source
<223> OTHER INFORMATION: /note= "Description of artificial sequence:
      antisense primer for cloning variant N88R of murine IL-2"

<400> SEQUENCE: 25
caacagttac tctgatacgg ctgatgaaat tctc                                34

<210> SEQ ID NO 26
<211> LENGTH: 43
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning variant Q126M of murine IL-2"

<400> SEQUENCE: 26
ggagatggat agccttctgt atgagcatca tctcaacaag ccc                      43

<210> SEQ ID NO 27
<211> LENGTH: 43
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning variant Q126M of murine IL-2"

<400> SEQUENCE: 27
gggcttgttg agatgatgct catacagaag gctatccatc tcc                      43

<210> SEQ ID NO 28
<211> LENGTH: 27
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning variant D20I of murine IL-2"

<400> SEQUENCE: 28
gagcagctgt tgatgatcct acaggag                                        27

<210> SEQ ID NO 29
<211> LENGTH: 27
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning variant D20I of murine IL-2"

<400> SEQUENCE: 29
ctcctgtagg atcatcaaca gctgctc                                        27

<210> SEQ ID NO 30
<211> LENGTH: 35
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning murine IL-7"

<400> SEQUENCE: 30
ccgctcgagc ggatgttcca tgtttctttt agata                               35
```

<210> SEQ ID NO 31
<211> LENGTH: 33
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning murine IL-7"

<400> SEQUENCE: 31
cggggtaccc cgttatatac tgcccttcaa aat                                  33

<210> SEQ ID NO 32
<211> LENGTH: 32
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning murine IL-18"

<400> SEQUENCE: 32
ccgctcgagc ggatggctgc catgtcagaa ga                                   32

<210> SEQ ID NO 33
<211> LENGTH: 43
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning murine IL-18"

<400> SEQUENCE: 33
cggggtaccc cgctaacttt gatgtaagtt agtgagagtg aac                       43

<210> SEQ ID NO 34
<211> LENGTH: 43
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning variant K89A of murine IL-18"

<400> SEQUENCE: 34
ccagactgat aatatacatg tacgcagaca gtgaagtaag agg                       43

<210> SEQ ID NO 35
<211> LENGTH: 43
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning variant K89A of murine IL-18"

<400> SEQUENCE: 35
cctcttactt cactgtctgc gtacatgtat attatcagtc tgg                       43

<210> SEQ ID NO 36
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning mature murine IL-18"

```
<400> SEQUENCE: 36
ggtggaggcg gttcaggcgg aggtggctct aactttggcc gacttcactg          50

<210> SEQ ID NO 37
<211> LENGTH: 31
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning mature murine IL-18"

<400> SEQUENCE: 37
ctaactttga tgtaagttag tgagagtgaa c                              31

<210> SEQ ID NO 38
<211> LENGTH: 32
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning murine IL-21"

<400> SEQUENCE: 38
ccgctcgagc ggatggagag gacccttgtc tg                             32

<210> SEQ ID NO 39
<211> LENGTH: 37
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning murine IL-21"

<400> SEQUENCE: 39
cggggtaccc cgctaggaga gatgctgatg aatcatc                        37

<210> SEQ ID NO 40
<211> LENGTH: 32
<212> TYPE: DNA
<213> ORGANISM: artificial sequence
<220> FEATURE:
<221> NAME/KEY: source
<223> OTHER INFORMATION: /note= "Description of artificial sequence:
      sense primer for cloning murine IL-15"

<400> SEQUENCE: 40
ccgctcgagc ggatgtacag catgcagctc gc                             32

<210> SEQ ID NO 41
<211> LENGTH: 31
<212> TYPE: DNA
<213> ORGANISM: artificial sequence
<220> FEATURE:
<221> NAME/KEY: source
<223> OTHER INFORMATION: /note= "Description of artificial sequence:
      antisense primer for cloning murine IL-15"

<400> SEQUENCE: 41
cggggtaccc cgctacttgt catcgtcgtc c                              31

<210> SEQ ID NO 42
<211> LENGTH: 32
<212> TYPE: DNA
<213> ORGANISM: artificial sequence
<220> FEATURE:
```

```
<221> NAME/KEY: source
<223> OTHER INFORMATION: /note= "Description of artificial sequence:
      primer 5' for generating the mIL2/IL18 fusion"

<400> SEQUENCE: 42
ccgctcgagc ggatgtacag catgcagctc ga                                32

<210> SEQ ID NO 43
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      5' linker primer for generating the lIL2/IL18 fusion"

<400> SEQUENCE: 43
ggtggaggcg gttcaggcgg aggtggctct atggctgcca tgtcagaaga             50

<210> SEQ ID NO 44
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      3' linker primer for generating the mIL2/IL18 fusion"

<400> SEQUENCE: 44
agagccacct ccgcctgaac cgcctccacc ttgagggctt gttgagatga             50

<210> SEQ ID NO 45
<211> LENGTH: 49
<212> TYPE: DNA
<213> ORGANISM: artificial sequence
<220> FEATURE:
<221> NAME/KEY: source
<223> OTHER INFORMATION: /note= "Description of artificial sequence:
      5' linker primer for generating the mIL18/IL2 fusion"

<400> SEQUENCE: 45
ggtggaggcg gttcaggcgg aggtggctct atgtacagca tgcagctcg              49

<210> SEQ ID NO 46
<211> LENGTH: 60
<212> TYPE: DNA
<213> ORGANISM: artificial sequence
<220> FEATURE:
<221> NAME/KEY: source
<223> OTHER INFORMATION: /note= "Description of artificial sequence:
      3' linker primer for generating the mIL18/IL2 fusion"

<400> SEQUENCE: 46
agagccacct ccgcctgaac cgcctccacc actttgatgt aagttagtga gagtgaacat  60

<210> SEQ ID NO 47
<211> LENGTH: 31
<212> TYPE: DNA
<213> ORGANISM: artificial sequence
<220> FEATURE:
<221> NAME/KEY: source
<223> OTHER INFORMATION: /note= "Description of artificial sequence:
      3' primer for generating the mIL18/IL2 fusion"

<400> SEQUENCE: 47
cggggtaccc cgttattgag ggcttgttga g                                 31

<210> SEQ ID NO 48
```

```
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      sequence for generating the mIL2/mature IL18 fusion"

<400> SEQUENCE: 48
ggtggaggcg gttcaggcgg aggtggctct aactttggcc gacttcactg         50

<210> SEQ ID NO 49
<211> LENGTH: 31
<212> TYPE: DNA
<213> ORGANISM: artificial sequence
<220> FEATURE:
<221> NAME/KEY: source
<223> OTHER INFORMATION: /note= "Description of artificial sequence:
      3' primer for generating the mIL2/ mature IL18 fusion"

<400> SEQUENCE: 49
ctaactttga tgtaagttag tgagagtgaa c                              31

<210> SEQ ID NO 50
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      5' linker primer for generating the mIL2/IL7 fusion"

<400> SEQUENCE: 50
ggtggaggcg gttcaggcgg aggtggctct atgttccatg tttcttttag          50

<210> SEQ ID NO 51
<211> LENGTH: 49
<212> TYPE: DNA
<213> ORGANISM: artificial sequence
<220> FEATURE:
<221> NAME/KEY: source
<223> OTHER INFORMATION: /note= "Description of artificial sequence:
      3' linker primer for generating the mIL7/IL2 fusion"

<400> SEQUENCE: 51
agagccacct ccgcctgaac cgcctccacc tatactgccc ttcaaaatt           49

<210> SEQ ID NO 52
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      5' linker primer for generating the mIL2/IL21 fusion"

<400> SEQUENCE: 52
ggtggaggcg gttcaggcgg aggtggctct atggagagga cccttgtctg          50

<210> SEQ ID NO 53
<211> LENGTH: 52
<212> TYPE: DNA
<213> ORGANISM: artificial sequence
<220> FEATURE:
<221> NAME/KEY: source
<223> OTHER INFORMATION: /note= "Description of artificial sequence:
      3' linker primer for generating the mIL21/IL2 fusion"

<400> SEQUENCE: 53
```

-continued agagccacct ccgcctgaac cgcctccacc ggagagatgc tgatgaatca tc      52

<210> SEQ ID NO 54
<211> LENGTH: 55
<212> TYPE: DNA
<213> ORGANISM: artificial sequence
<220> FEATURE:
<221> NAME/KEY: source
<223> OTHER INFORMATION: /note= "Description of artificial sequence:
      5' linker primer for generating the mIL2/IFNg fusion"

<400> SEQUENCE: 54
ggtggaggcg gttcaggcgg aggtggctct atgaacgcta cacactgcat cttgg      55

<210> SEQ ID NO 55
<211> LENGTH: 33
<212> TYPE: DNA
<213> ORGANISM: artificial sequence
<220> FEATURE:
<221> NAME/KEY: source
<223> OTHER INFORMATION: /note= "Description of artificial sequence:
      sequence for generating the mIL2/IFNg fusion"

<400> SEQUENCE: 55
cggggtaccc cgtcagcagc gactcctttt ccg      33

<210> SEQ ID NO 56
<211> LENGTH: 37
<212> TYPE: DNA
<213> ORGANISM: artificial sequence
<220> FEATURE:
<221> NAME/KEY: source
<223> OTHER INFORMATION: /note= "Description of artificial sequence:
      5' primer for cloning the mIFNg/IL2 fusion"

<400> SEQUENCE: 56
ccgctcgagc ggatgaacgc tacacactgc atcttgg      37

<210> SEQ ID NO 57
<211> LENGTH: 49
<212> TYPE: DNA
<213> ORGANISM: artificial sequence
<220> FEATURE:
<221> NAME/KEY: source
<223> OTHER INFORMATION: /note= "Description of artificial sequence:
      3' linker primer for generating the mIFNg/IL2 fusion"

<400> SEQUENCE: 57
agagccacct ccgcctgaac cgcctccacc gcagcgactc cttttccgc      49

<210> SEQ ID NO 58
<211> LENGTH: 50
<212> TYPE: DNA
<213> ORGANISM: artificial sequence
<220> FEATURE:
<221> NAME/KEY: source
<223> OTHER INFORMATION: /note= "Description of artificial sequence:
      5' linker primer for generating the mIL2/IL15 fusion"

<400> SEQUENCE: 58
ggtggaggcg gttcaggcgg aggtggctct atgtacagca tgcagctcgc      50

<210> SEQ ID NO 59
<211> LENGTH: 49
<212> TYPE: DNA
<213> ORGANISM: artificial sequence
<220> FEATURE:
<221> NAME/KEY: source
<223> OTHER INFORMATION: /note= "Description of artificial sequence:

-continued

3' linker primer for generating the mIL15/IL2 fusion"

<400> SEQUENCE: 59
agagccacct ccgcctgaac cgcctccacc cttgtcatcg tcgtccttg         49

VIRAL PARTICLES ENCODING MULTIFUNCTIONAL CYTOKINES

CROSS REFERENCE TO RELATED APPLICATIONS

This is a Divisional of U.S. application Ser. No. 10/565,371, filed Dec. 13, 2006 now U.S. Pat. No. 7,534,585, which is a 371 Application of International Application No. PCT/EP2004/008114, filed Jul. 20, 2004, which claims priority to U.S. Provisional Application No. 60/539,320, filed Jan. 28, 2004 and EP 03360086.7, filed Jul. 21, 2003, all of which are incorporated herein by reference.

The present invention relates to a novel fusion protein with the formula X-Y, or Y-X, wherein X represents a first immunoregulating polypeptide and Y represents a second immunoregulating polypeptide different from X. The present invention also relates to a nucleic acid molecule encoding such a fusion protein and a vector comprising such a nucleic acid molecule. The present invention also provides infectious viral particles and host cells comprising such a nucleic acid molecule or such a vector as well as a process for producing such infectious viral particles. The present invention also relates to a method for recombinantly producing such a fusion protein. Finally, the present invention also provides a pharmaceutical composition comprising such a fusion protein, a nucleic acid molecule, a vector, infectious viral particles and a host cell as well as the therapeutic use thereof.

The present invention is particularly useful in the field of gene therapy and immunotherapy, especially for treating or preventing a variety of diseases, including cancers and infectious diseases (bacteria and virus infections).

Broadly speaking, host's immune responses fall into two categories: nonspecific (or innate) and specific (or adaptive or acquired). The differences between these is that an specific immune response is highly specific for a particular antigen whereas nonspecific response does not rely on a repeated exposure to a given pathogen/antigen. The networks controlling the immune system rely on secreted proteins (e.g. cytokines) to turn on and off the functions of immune cells as well as to regulate their proliferation and to control the magnitude of the immune response. Specifically, two types of lymphocytes—B and T cells—are at the core of specific immunity. Upon being triggered by an antigen, B cells divide and the daughter cells synthesize and secrete antibody molecules (humoral immunity). T cell activation entails development of cell-mediated immunity, mediated among others by cytotoxic T lymphocytes (CTL) that specifically eliminates non-self antigen-bearing target cells (e.g. infected or tumoral cells). Activation of a specific (or adaptive) immune response is orchestrated by numerous cytokines. Of particular importance are interleukin (IL)-1, IL-2, IL-6, IL-7, IL-15 and interferon gamma (IFNg). On the other hand, nonspecific (innate) responses involve different types of immune cells, including natural killer (NK) cells, Natural Killer T cells (NKT), dendritic cells (DCs) and macrophages, and are among others mediated by the secretion of cytokines such as IL-2, IL-12, IL-15, IL-18 and IL-21. In reality, however, a strict distinction between specific and nonspecific immune responses is somewhat arbitrary, as the elimination of pathogens and tumors in viva is likely to involve both types of immune responses acting in concert. Also, through cytokine signalling pathways, specific effectors may play a major role in the induction and activation of nonspecific effectors and vice versa. For example, one striking property of NKT cells is their capacity to rapidly produce large amounts of cytokines in response to T-cell receptor engagement, suggesting that activated NKT cells can also modulate specific immune responses. For a general discussion of immune response, immune effector cells and immune mediators, see for example the most updated editions of "Encyclopedia of Immunology" (Edited by Ivan Roitt and Peter Delves; Academic Press Limited) and "Fundamental Immunology (e.g. $2^{nd}$ edition, Edited by W. Paul; Raven Press).

It is generally accepted that cancer is a multistep process which results from a loss of the control of cell multiplication. An extensive body of research exists to support the involvement of tumor-associated antigens (TAAs) in the onset of the malignant phenotype. These antigens include oncogene products (e.g. p53, ras, neu, erb), reactivated embryonic gene products (e.g. P91A found in P815 mastocytoma), modified self-antigens (e.g. hyperglycosylated MUC-1), oncogenic viral genes (e.g. early antigens of papillomavirus) and a variety of others. With regard to the mechanism that operates in the recognition and elimination of tumor cells, it has been shown that T lymphocytes play a key role in conferring specificity to tumor rejection. In particular, CD8+ cytotoxic T lymphocytes (CTL) were identified as important effector cells for recognizing specific tumor antigens. CTLs can kill tumors only after they have been presensitized to a tumor antigen and only when it is presented at the cell surface by MHC class I gene products. In many cases, the induction of the anti-tumoral response is also dependent on the presence of CD4+ T cells. In addition to these specific immune effector cells, roles have been identified in tumor rejection for NK cells and other nonspecific effector cells such as NKT and macrophages, which can lyse tumor cells in a manner that is not antigen-dependent and not MHC-restricted.

Despite the fact that the vast majority of tumor-associated antigens is capable of being recognized as foreign by the immune system of the patient and the abundance of tumoricidal immune mechanisms, most cancers do not provoke immunological responses sufficient to control the growth of malignant cells. Tumor cells have developed several mechanisms which enable them to escape host immunity due to a reduction in antigen presentation by the tumor cells or due to a generalized decline in patient's immunity. As the expression of MHC class I determinants on cell surface is essential for the recognition of foreign antigens by CTLs, suppression or failure to express MHC class I antigens is one of the documented mechanisms used by tumor cells to evade the immune system (Tanaka et al., 1988, Ann. Rev. Immunol. 6, 359-380). Another mechanism of immune anergy involves the shedding of tumor antigens, thus preventing the interaction of the immune cells with the tumor target cell itself. Moreover, tumors can activate immunosuppressive molecules to dampen the vigor of immune responses to tumor antigens or to activate apoptosis of immune effector cells. For example, IL-2 may have in some circumstances, a critical role in the maintenance of peripheral tolerance. As a result of its pivotal role in activation-induced cell death (AICD), the T cells generated in response to tumour vaccines containing IL-2 may interpret the tumor cells as self and the tumor-reactive T cells may be killed by AICD-induced apoptosis (Lenardo, 1996, J. Exp. Med. 183, 721-724). Furthermore, IL-2 maintains $CD4^+$ $CD25^+$ negative regulatory T cells and has been reported to terminate $CD8^+$ memory T cell persistence (Shevach, 2000, Ann. Rev. Immunol. 18, 423-449).

A number of studies have documented a critical role for tumor-specific CD4(+) cells in the augmentation of immunotherapeutic effector mechanisms. However, chronic stimulation of such CD4(+) T cells often leads to the up-regulation of both Fas and Fas ligand, and coexpression of these molecules can potentially result in activation-induced cell death (AICD)

and the subsequent loss of anti-tumor response. By contrast, resistance to AICD significantly enhances T cell effector activity (Saff et al. 2004, J. Immunol. 172, 6598-6606).

A number of previous approaches have used cytokines to enhance host's immunity, and thus to overcome tumor-induced state of immune anergy. For example, human IL-2 (Proleukin) is an approved therapeutic for advanced-stage metastatic cancer. However, the systemic administration of cytokines is often poorly tolerated by the patients and is frequently associated with a number of side-effects including nausea, bone pain and fever (Mire-Sluis, 1993, TIBTech vol. 11; Moore, 1991, Ann Rev Immunol. 9, 159-191). These problems are exacerbated by the dose levels that are required to maintain effective plasma concentrations. Cytokine delivery using virus vectors and cell vehicles have been proposed to reduce systemic toxicity.

Genetically modified tumor cells releasing various cytokines have been shown to enhance tumor immunogenicity and to induce the regression of pre-existing tumors. Immunization with tumor cells modified to secrete IL-2 (Karp et al., 1993, J. Immunol. 150, 896-908), alpha interferon (IFNa) (Porgador et al., 1993, J. Immunol. 150, 1458-1470) or GM-CSF (Dranoff et al., 1993, PNAS 90, 3539-3543) have been shown to enhance tumor immunogenicity and to induce the regression of preexisting tumors. In some instances, immunological memory has been generated to resist the subsequent challenge with unmodified, parental tumor cells. Moreover, cytokine-transduced tumors may attract an inflammatory exudate in vivo that generally results in tumor destruction in animal models. Experimental animals and a small number of patients with established neoplasms treated with the cytokine-secreting tumor cells survived for a longer period of time, although in most instances tumor-growth eventually recurred.

The direct injection into solid tumors of vectors carrying genes encoding a variety of cytokines and chemokines has also been attempted in order to enhance the presentation of T-cell epitopes or to enhance the activation of tumor-specific T-lymphocytes. Many cytokines, including gamma interferon (IFN-g), IL-2 (Slos et al., 2001, Cancer Gene Ther. 8, 321-332), IL-7 (Miller et al., 2000, Human Gene Therapy 11(1), 53-65; Sharma et al., 1996, Cancer Gene Therapy 3, 302-313), IL-12 (Melero et al., 2001, Trends Immunol. 22, 113-115), IL-15 (Suzuki et al., 2001, J. Leukoc. Biol. 69, 531-537; Kimura et al., 1999, Eur. J. Immunol. 29, 1532-1542), IL-18 (Cao et al., 1999, FASEB J. 13, 2195-2202), and IL-21 (Ugai et al., 2003, Cancer Gene Therapy 10, 187-192) have demonstrated significant antitumor activity in mice. For example, intra-tumoral injection of dendritic cells transduced with an adenovirus expressing IL-7 leads to significant systemic immune responses and potent anti-tumor effects in murine lung cancer models (Miller et al., 2000, Hum Gene Ther. 11, 53-65).

More recently, many studies with both mouse and human tumor models have shown the importance of cytokine combinations in the development of optimal immune responses (see for example Putzer et al., 1997, Proc Natl Acad Sci USA. 94, 10889-10894; Melero et al., 2001, Trends Immunol. 22, 113-115; Zhu et al., 2001, Cancer Res. 61, 3725-3734). For example, the combination of IL-12 with the Th1 promoting IL-18 has been shown useful for the stimulation of the cell-mediated immune response (Hashimoto et al., 1999, J. Immunol. 163, 583-589; Barbulescu et al., 1998, J. Immunol. 160, 3642-3647). IL-2 and IFNg have been shown to cooperate for inhibiting tumor cell growth (U.S. Pat. No. 5,082,658). More recently, IL-21 was described to synergize the effects of IL-15 or IL-18 in the enhancement of 11-Ng production in human NK and T cells (Strengell et al., 2003, J. Immunol., 170, 5464-5469). The combination of IL-4 and GM-CSF is particularly useful in stimulating DCs (Palucka et al., 1998, J. Immunol. 160, 4587-4595). In other studies, it was found that the combination of IL-3 and IL-11 had a synergistic effect with IL-12 on the proliferation of early hematopoktic progenitor cells (Trinchieri et al., 1994, Blood 84, 4008-4027). Graham and colleagues pioneered the combination of two adenoviruses, one encoding IL-2 and the other IL-12 (Addison et al., 1998, Gene Ther. 5, 1400-1409). They observed complete regression in more than 60% of established mammary carcinomas and induction of potent antitumor CTL activity. Recent data show that IL-15 can also synergize with IL-12 after double-transfection of human lung cancer cells (Di Carlo et al., 2000, J. Immunol. 165, 3111-3118). Also, IL-18 has been identified as a potent inducer of IFNg, and importantly, upregulates the expression of IL-12 receptors (Nakanishi et al., 2001, Ann. Rev. Immunol. 19, 423-474). In a reported poorly immunogenic tumor (MCA205), a clear synergy between these two cytokines was observed with antitumor effects mainly mediated by NK, cells.

However, in many of these studies, it was found that the relative level of each cytokine was very important. For example, synergy studies between IL-12 and other cytokines for the generation of antitumor responses in mice have shown mixed results. Whereas the addition of IL-12 in the presence of suboptimal amounts of IL-2 led to synergy in the induction, proliferation, cytolytic activity and IFNg induction, combinations of IL-2 and IL-12 using a high dose of one cytokine were found to be antagonistic (Perussia et al., 1992, J Immunol. 149, 3495-3502; Mehrotra et al., 1993, J. Immunol. 151, 2444-2452). In some models, a non-optimal dose of one cytokine with respect to the other led to an enhanced toxicity, while in other models, combinations of IL-12 and IL-2 showed little or no synergy (e.g. Nastala et al., 1994, J. Immunol. 153, 1697-1706). A similar situation occurs with combinations of IL-12 and IL-7. These results may reflect the inherent difficulty of combining two potentially synergistic cytokines in vivo, especially when there is a need to maintain a fixed ratio of activities of two components with different pharmacological properties, such as different circulating half life and biodistribution.

To reduce the difficulties inherent to cytokine combinations, one strategy is to fuse the cytokines. Fusions between two cytokines have already been proposed in the literature. For example, WO 01/10912 describes fusions between IL-12 and a second cytokine with short half life in order to provide a longer pharmacokinetic behavior similar to that of IL-12 itself. The fusion of IL-12 with either IL-2, granulocyte-macrophage colony-stimulating factor (GM-CSF) or IL-4 is specifically disclosed. U.S. Pat. No. 5,883,320 and WO 92/04455 disclose fusions between IL-3 and a second cytokine, which may be used in the treatment of diseases associated with a decreased level of hematopoïetic cells. The fusion between IL-3 and IL-11 was shown to be useful for stimulating the production of megakaryocytes and platelets. Drexler et al. (1998, Leuk Lymphoma 29, 119-128) describe the fusion of GM-CSF and IL-3. Finally, U.S. Pat. No. 6,261,550 envisages the fusion of G-CSF with a cytokine to enhance hematopoïesis, e.g. to compensate hematopoïetic deficits resulting from chemotherapy or radiation therapy in cancer patients.

The development of efficient molecules against human tumors has been a long sought goal which has yet to be achieved. In light of the forgoing, there remains a need for cytokine fusions which evoke an immune response and are capable of bypassing tumor immunosuppression.

This technical problem is solved by the provision of the embodiments as defined in the claims.

The present invention provides novel fusion proteins that are useful for enhancing an immune response, especially a specific together with a nonspecific immune response in a host organism. The resulting response is useful for reversing immunosuppression or anergy mechanisms induced by pathogens or cancer cells. These fusion proteins or vectors expressing them can be used for protecting an animal or a human against a variety of clinical conditions, such as acute or chronic infections or cancers. The present invention illustrates fusion proteins that provide a high rate of tumor rejection after intratumoral delivery of adenoviral vectors encoding them into various animal models, providing evidence for significant immunostimulation. In accordance with the present invention, these fusion proteins or their encoding sequences may also be used as immunoadjuvant to vaccine technologies (e.g. in combination with one or more immunogen(s)) or in combination with suicide gene approaches, in the prevention and treatment of cancer or infectious diseases in humans and other mammals.

Accordingly, in a first aspect, the present invention provides a novel fusion protein with the formula:

$$X\text{-}Y, \text{ or} \qquad a)$$

$$Y\text{-}X, \qquad b)$$

wherein X represents a first immunoregulatory polypeptide;

Y represents a second immunoregulatory polypeptide; and X is different from Y.

As used herein throughout the entire application, the terms "a" and "an" are used in the sense that they mean "at least one", "at least a first", "one or more" or "a plurality" of the referenced compounds or steps, unless the context dictates otherwise. For example, the term "a cell" includes a plurality of cells including a mixture thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, when used to define products, compositions and methods, the teen "comprising" is intended to mean that the products, compositions and methods include the referenced components or steps, but not excluding others. "Consisting essentially of" shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The term "polypeptide" or "protein" are used herein interchangeably to refer to polymers of amino acids of any length, preferably of at least 50 amino acid residues. The polymer may be linear or branched, it may comprise modified amino acids, and it may be interrupted by non-amino acids. The term also encompasses an amino acid polymer that has been modified in one or more amino acid residue(s) by way of substitution or addition of moieties or by chemical modification techniques well known in the art. Included within the scope of the present invention are for example disulfide bond formation, glycosylation, lipidation, iodination, hydroxylation, methylation, acetylation, acylation, gamma carboxylation, phosphorylation, proteolytic processing, or any other manipulations such as conjugation or binding with a detectable moiety (i.e. a scintigraphic, radioactive, fluorescent, or dye labels and the like). Suitable radioactive labels include but are not limited to $^{99m}$Tc, $^{123}$I and $^{111}$In. In the context of this invention, the terms "amino acid" and "residue" are synonyms. They encompass natural, unnatural and/or synthetic amino acids, including D or L optical isomers, modified amino acids and amino acid analogs.

The term "fusion" or "fusion protein" or "fusion cytokine" as used herein refers to the combination of amino acid sequences of the first polypeptide and of the second polypeptide in one polypeptide chain, preferably by in frame fusion of corresponding coding nucleotide sequences. In the nature, the X and Y entities may normally exist in separate proteins, which are brought together in the fusion protein of the invention. In the fusion protein of the present invention, the coding sequence of the first polypeptide (X) is fused in frame with the coding sequence of the second polypeptide (Y) either directly or through a linker. By "fused in frame" is meant that the expression of the fused coding sequences results in the fusion protein comprising both the first and the second polypeptides. This means for example that there is no translational terminator between the reading frames of the X and Y polypeptides. Even through the fusion between the X and Y entities can take place internally at any site, the Y entity is preferably fused to either the COOH or the NH2 terminus of the X entity (resulting in a fusion of the formula X-Y and Y-X respectively). As used herein, the term "directly" refers to a fusion of the polypeptides X and Y without a peptide linker in between (i.e. the codons encoding the X entity are contiguous to the codons encoding the Y entity). In addition, the fusion protein may also include further elements apart from X, Y and a linker, such as an initiator methionine, a signal peptide and/or a propeptide. Fusion proteins essentially consisting of or consisting of X and Y, and optionally a linker, are preferred embodiments in the context of the present invention.

The term "immunoregulatory polypeptide" as used herein refers to a polypeptide capable of regulating an immune response in an animal or human organism. "Regulating an immune response" refers to modulating the activity of immune effector cells or mediator molecules involved in an immune response. The term "regulate" can refer to enhancing or reducing an immune response, with a special preference for an enhancement. As used herein the tens "enhancing" refers to inducing the onset and/or modulating the magnitude and duration of an immune response leading to the activation, differentiation, maturation and/or proliferation of one or more immune effector cells and/or to the production of appropriate immune mediators, and/or to the improvement of antigen presentation, and/or to the onset of a clinical benefit (e.g. inhibition of tumor growth, tumor regression). Regulation of an immune response can be determined using methods known in the art as well as methods disclosed herein.

The fusion protein of the invention "enhances" an immune response when the immune response—whether specific or nonspecific—observed with the addition of the fusion protein is greater or intensified in any way when compared to the same immune response measured without its addition. Preferably, the enhancement of the immune response provided by the fusion protein of the invention leads to the amelioration of a disease condition. The ability of the fusion polypeptide of the invention to enhance an immune response can be evaluated either in vitro or in vivo using a variety of assays which are standard in the art. For a general description of techniques available to evaluate the onset and activation of an immune response, whether specific or non specific, see for example Coligan et al. (1992 and 1994, Current Protocols in Immunology; ed J Wiley & Sons Inc, National Institute of Health;

incorporated herein by reference). Testing and validation of the fusion proteins of the invention are also illustrated in the appended Example section. Suitable assays include without limitation the determination of the activation status for a particular type of immune effector cells, the proliferation rate of such cells, the quantification of the cell-surface markers, the lytic activity of the immune effector cells towards appropriate tumor or target cells, the measurement of cytokine expression profiles secreted by the activated effector cells. Suitable methods for proceeding to the evaluation of an immune response are conventional and include among others ELISA, immunofluorescence, Western blotting, immunohistochemistry, histology, flow cytometry (FACS). For example, T cell proliferation can be determined, e.g. by a classical [$^3$H]thymidine uptake assay. As another example, the lytic activity of cytotoxic T cells can be measured, e.g. using a $^{51}$Cr release assay, with and without the fusion protein. Naive and activated immune effector cells can also be discriminated by the identification of specific cell surface markers. For example, immature or nave T cells may be identified by their expression of the high molecular weight isoform of the CD45 molecule known as CD45RA. Mature T cells express the low molecular weight isoform of CD45 known as CD45RO. Upregulation of CD80, CD86 and MHCII-Iab reflects maturation of dendritic cells. The presence of CD8 is a marker of activated CTLs. Other informative markers of the type or maturation/activation status of these immune cells are known in the art. Suitably, the candidate fusion protein can also be tested in an appropriate animal model to evaluate its anti-tumor activity, reflecting an enhancement of the immune response. For example, the fusion protein can be administered into tumor animal models and the tumor growth and/or the survival rate are evaluated periodically as compared to a control. In addition to in vivo methods for determining tumor inhibition, a variety of in vitro methods may be utilized in order to predict in vivo tumor inhibition. Representative examples include lymphocyte mediated anti-tumor cytolytic activity determined, for example, by a $^{51}$Cr release assay, tumor dependent lymphocyte proliferation (Ioannides et al., 1991, J. Immunol. 146, 1700-1707), in vitro generation of tumor-specific antibodies (Herlyn et al., 1984, J. Immunol. Meth. 73, 157-167), cell (e.g., CTL, helper T cell) or humoral (e.g., antibody)-mediated inhibition of cell growth in vitro (Gazit et al., 1992, Cancer Immunol. Immunother. 35; 135-144) and determination of cell precursor frequency (Vose, 1982, hit. J. Cancer 30, 135-142).

In a preferred embodiment, the fusion protein of the invention provides an enhancement of the immune response as compared to the corresponding immune response when said fusion protein is not added, by a factor of at least 2, more preferably by a factor of at least 3.

The fusion proteins encompassed by the present invention are not limited by the particular identity of X and Y, nor by the number of X and/or Y entities employed in the fusion protein. The X and the Y polypeptides are different, i.e. heterologous with respect to one another. The difference may be in terms of structure (e.g. below 40% of identity between their respective amino acid sequence) and/or in terms of their respective biological activity (e.g. X and Y are involved in different pathways of the immune system). The X and Y entities involved in the fusion protein of the invention may individually originate (be obtained, isolated) from human or animal origin (e.g. canine, avian, bovine, murine, ovine, porcine, feline, simian and the like). The fusion protein may also comprise X and Y entities of diverse origins (e.g. X of human origin and Y of animal origin).

In a preferred embodiment, X represents an immunoregulatory polypeptide capable of enhancing a specific immune response, whereas Y represents an immunoregulatory polypeptide capable of enhancing a nonspecific immune response.

According to a preferred embodiment, the X and Y immunoregulatory polypeptides in the above formulae each represents a cytokine. As used herein, "cytokine" refers to a polypeptide that generally acts as a mediator of immunity being specific and/or non specific. It will be appreciated that the present invention aims at providing a "multifunctional" fusion cytokine capable of inducing or enhancing an immune response in a host cell or organism, thus allowing to reduce or inhibit at least one mechanism of immune anergy that has been developed by tumor or infected cells to escape host immunity.

In accordance with the general goal of the present invention, X preferably represents a cytokine capable of enhancing a nonspecific (innate) immune response, especially an immune response mediated by one or more of the effector cells selected from the group consisting of macrophages, dendritic cells, NK cells and NKT cells. Y preferably represents a cytokine capable of enhancing a specific (adaptative) immunity, especially an immune response mediated by effector cells such as B and/or T lymphocytes (CD4+ and/or CD8+ T cells).

A non-exclusive list of cytokines which are comprised by the definition of X and/or Y includes the interleukins (IL), interferons (IFN), chemokines, Tumor Necrosis Factor receptor ligands (e.g. 4-1BBL, OX40L, GITRL), KIR (Killing Inhibitory Receptor) ligands, KAR (Killing activatory Receptor) ligands (e.g. RAE-1 as disclosed in Genbank accession number AF346595) and H60; see for example Diefenbach et al., 2001, Nature 413, 165-171; Diefenbach et al., 2003, Eur. J. Immunol. 33, 381-391), IRFs (IFN regulatory factors) (e.g. IRF-3 as disclosed in Genbank accession number NM001571), IRF-7 as disclosed in Genbank accession number U53830 or chimeras thereof; see for example Au et al., 1995, Proc. Natl. Acad. Sci. USA 92, 11657-11661; Zhang and Pagano, 1997, Mol. Cell. Biol. 17, 5748-5757; Nguyen, et al., 1997, Cytokine Growth Factor Rev. 8, 293-312; Duguay et al., 2002, Cancer Res. 62, 5148-5152; Sharma et al., 2003, Science 300, 1148-1151; Bramson et al., 2003, Vaccine 21, 1363-1370) and B cell stimulatory factors. X and Y may include independently, without limitation, precursor, mature forms, variants of cytokines. Appropriate cytokines include without limitation IL-1 through IL-31, and IFNs alpha through gamma. It will be appreciated that these cytokines and the methods available to quantify their levels in a given medium are described in basic text books such as Oppenheim et al. (2001, Cytokine Reference; A compendium of cytokines and other mediators of host defense; Eds Durum et al. Academic Press). Preferred fusion proteins are those wherein X and Y are independently IL-2, IL-7, IL-15, IL-18, IL-21, IL-27, IL-31 or IFNg. Preferably Y is not GM-CSF when X is IL-2 and Y is not IL-2, GM-CSF or IL-4 when X is IL-12.

IL-2 is a pleiotropic cytokine acting both in specific and non specific immunity. After more than 20 years of research, it has been established that IL-2 is a potent growth and differentiation factor for T cells. IL-2 also stimulates the cytolytic activity of NK cells (Caligiuri et al., 1990, J. Exp. Med. 171, 1509-1526) and of the so-called lymphocyte activated killer (LAK) cells (Pawelec et al., 1999, Crit. Rev Oncog. 10, 83-127). IL-2 induces the secretion of other cytokines including IFN-g (Trinchieri et al., 1984, J. Exp. Med. 160, 1147-1169). IL-2 also shows strong B cell growth factor activity and can stimulate monocyte-lineage cells. IL-2 appears to be produced exclusively by antigen-activated T lymphocytes including both CD4+ and CD8+ T cells. IL-2 mediates its biological activities by binding to IL-2 receptors (IL-2R), which are expressed transiently on antigen-activated T cells and continuously by NK cells. The mature human IL-2 protein consists of 133 amino acids (Taniguchi et al., 1983, Nature 302, 305-310). It is synthesized as a precursor containing 153 amino acids with a 20-residue hydrophobic leader sequence (signal peptide) that is cleaved to produce the mature protein prior to or during secretion. The amino acid and nucleotide sequence of IL-2 from 31 species are now well known. For example, the sequence of human IL-2 protein in NCBI Genbank under accession number P01585. Genbank accession numbers NM008366 and NM000586 describe the mouse and human IL-2 gene sequences, respectively (all accession numbers incorporated herein by reference).

IL-7 plays an essential role in the development of T and B cells. It also plays a role in differentiation of these cells. IL-7 stimulates the growth of immature and mature T cells, affects survival and proliferation of mature T cells, and promotes the expansion and effector functions of cytolytic T cells and their precursors. Additionally, IL-7 enhances LAK cell activity in peripheral blood and can stimulate the anti-tumor activity of monocytes and macrophages. IL-7 also down-regulates both macrophage and tumor production of TGFβ and thus may serve to limit tumor-induced immune anergy (Dubinett et al., 1993, J. Immunol. 151, 6670-6680; Miller et al., 1993, Blood 82, 3686-3694). IL-7 is a single chain glycosylated protein produced predominantly by epithelial cells, especially keratinocytes and thymic epithelial cells. The human IL-7 cDNA contains an open reading frame encoding a protein of 177 amino acids including a 25 amino acid signal peptide which is cleaved from the mature protein during the secretion process. The DNA and amino acid sequences of IL-7 from a number of species are now well known (see for example Namen et al., 1988, J. Exp. Med. 167, 988-1002; Namen et al., 1988, Nature, 333, 571-573; Conlon et al., 1989, Blood 74, 1368-1373). For example, the sequences of human, bovine and murine IL-7 proteins are disclosed in GenEMBL under accession numbers NP000871, CAA45838 and CAA30779, respectively. The nucleotide sequence of the mouse IL-7 gene is available in Genbank under accession number NM008371. The nucleotide sequence of the human IL-7 gene is available under accession number NM000880. The bovine IL-7 gene is disclosed under accession number X64540 (all accession numbers incorporated herein by reference). It will be appreciated that human (152 amino acids) and murine (127 amino acids) IL-7 show 60% sequence homology at the protein level.

Like IL-2, IL-15 is a pleiotropic cytokine acting both in specific and nonspecific immunity. The human IL-15 cDNA encodes a 162 amino acid precursor consisting of a 48 amino acid leader peptide and a 114 mature protein (Grabstein et al., 1994, Science 264, 965-968). IL-15 exerts its biological activities through binding to the IL-2R beta and gamma chains, supplemented by a specific IL-15R alpha chain (Giri et al., 1995, EMBO J. 14, 3654-3663). This sharing of receptor subunits probably accounts for the similar functional activities of IL-2 and IL-15 observed on T, B and NK, cells. IL-15 like IL-2 has been defined as a T cell growth factor (Grabstein et al., 1994, Science 264, 965-968; Nishimura et al., 1996, J. Immunol. 156, 663-669). One of the most critical functions of IL-15 is its pivotal role in the development, survival and activation of NK cells. Treatment of NK cells with IL-15 results in the proliferation and enhancement of cytotoxic activity and in the production of IFN-g, TNFa and GM-CSF (Carson et al., 1994, J. Exp. Med. 180, 1395-1403). Apart from its activities on T and NK cells, IL-15 costimulates, in a comparable way as IL-2, the proliferation of activated B cells (Armitage et al., 1995, J. 1 mmol. 154, 483-490). IL-15 promotes the generation and persistence of CD4+ memory cells (WO 98/36768). The most striking differences, however, between IL-15 and IL-2 reside in their expression pattern. Contrary to IL-2, IL-15 mRNA is widely distributed in a variety of non-lymphoid tissues such as fibroblasts and epithelial cells. On the other hand, it is not present in resting or activated T cells, the predominant source of IL-2. Grabstein et al. (1994, Science 264, 965-968) provides disclosure relating to obtaining the sequence for human IL-15. Genbank accession numbers NM008357 and NM000585 provide the mouse and human. IL-15 nucleotide sequences, respectively. Accession numbers in GenEMBL for IL-15 amino acid sequences are: human protein (P40933), murine protein (P48346), rat protein (P97604) and bovine protein (Q28028) (all accession numbers incorporated herein by reference).

IL-18 is a recently discovered Th1 cytokine that was described as having significant immunoregulatory fractions on both T and NK cells (Okamura et al., 1995, Nature 378, 88-91). In particular, IL-18 augments the proliferation of T cells, enhances cytotoxic activity of NK cells, induces secretion of GM-CSF from both NK and T cells, and synergizes with IL-12 in terms of IFN-g production (Okamura et al., 1998, Curr Opin Immunol. 10, 259-264). IL-18 is synthesized as a biologically inactive precursor molecule (pro-IL-18). To generate the active form of IL-18, the pro sequence needs to be cleaved by the intracellular cysteine protease, IL-1beta converting enzyme ICE, at the Asp-X processing site. IL-18 can inhibit tumor growth in some murine tumor systems, but regression of established tumor by IL-18 gene therapy alone has not been demonstrated (Micallef et al., 1997, Cancer Immunol Immunother. 43, 361-367; Osaki et al., 1998, J. Immunol. 160, 1742-1749; Osaki et al., 1999, Gene Ther. 6, 808-815; Hashimoto et al., 1999, J. Immunol. 163, 583-589). The DNA and protein sequences of the IL-18 molecule are published (see for example Okamura et al., 1995, Nature 378, 88-91; Ushio et al., 1996, J. Immunol., 156, 4274-4279; Genbank accession numbers NM008360 and NM001562 describing respectively the mouse and human IL-18 nucleotide sequences, and NP_001553 for the human IL-18 protein; all accession numbers incorporated herein by reference).

IL-21 is a recently identified cytokine with a four-helix-bundle structure (Parrish-Novak et al., 2000, Nature 408, 57-63). The expression and function of this cytokine and its receptor suggest that IL-21 is a new player in lymphoid differentiation. IL-21 was found to have potent effects on all classes of lymphocytes: B, T and NK cells. One of the most interesting biological activities of IL-21 is to substantially increase the cytotoxic activity of mature NK cells, independently of proliferation. The DNA and protein sequences of the IL-21 molecule are disclosed in the literature (see for example Parrish-Novak et al., 2000, Nature 408, 57-63; Genbank accession numbers NM021782 and NM021803 describing respectively the mouse and human IL-21 nucleotide sequences, and NP_065386 for the human IL-21 protein; all accession numbers incorporated herein by reference).

One cytokine that is well recognized to play a central role in coordinating tumor immune responses is IFNg. IFNg is mainly produced by activated lymphocytes and exerts its activities in specific immune responses. In this regard, IFN-g augments expression of the MHC class I molecules in professional as well as non-professional antigen-presenting cells. It is involved in T and B lymphocyte proliferation and differentiation. Production of IFNg by T helper cells is a hallmark of the Th1-type phenotype. Thus, high-level production of IFN-g is typically associated with an effective host defense against intracellular pathogens. The importance of IFNg in anti-tumor therapy is based on its anti-angiogenic properties, and its ability to down-regulate the expression of immunosuppressive molecules secreted by tumors. By increasing tumor immunogenicity, IFNg ultimately enhances tumor recognition by tumor-specific cytotoxic T lymphocytes, and favors tumor rejection (Beatty et al., 2001, Immunol Res. 24, 201-10). The DNA and protein sequences of the IFNg molecule are disclosed in the literature (see for example Gray et al., 1982, Nature 295, 503-508; Gray et al., 1983, Proc. Natl. Acad. Sci. USA 80, 5842-5846; Genbank accession number K00083 describing the mouse IFNg gene sequence and Genbank accession number NM000619 describing the human IFNg gene sequence, and II01579 for the human IFNg protein; all accession numbers incorporated herein by reference).

In a preferred aspect of the present invention, the fusion protein of the invention is a fusion protein wherein:
 (a) X is IL-2 and Y is selected from the group consisting of IL-7, IL-15, IL-18, IL-21, IL-27, IL-31 and IFN-g,
 (b) X is IL-12 and Y is selected from the group consisting of IL-15, IL-18 and IL-21,
 (c) X is IL-15 and Y is selected from the group consisting of IL-7, IL-18 and IL; 21; and
 (d) X is IL-18 and Y is IL-21;

In the context of the present invention, the X and Y entities used in the fusion proteins of the invention can be obtained (isolated or derived) from any species. Particularly preferred are fusions involving either the native or a biologically active modified form of the human cytokines. When referring to IL-12, it is mentioned that IL-12 can be in the form of a heterodimeric protein composed of 35 and 40 kDa subunits (in this case the Y entity is fused either to the 35 or the 40 kDa subunit) or in the form of a monomeric protein where 35 and 40 kDa subunits are fused together as a single chain protein (in this case the Y entity is fused to the 35-40 kDa fusion), this latter being preferred in the context of the present invention. Preferably, the IL-12 entity (p35 or p40 or p35-p40 single chain) is placed at the N-terminus of the fusion protein of the invention (e.g. IL-12/IL-15, IL-12/IL-21).

The conformation of the fusion may be important to reach the optimal activity of the fusion protein of the invention. Accordingly, the present invention provides fusion proteins which comprise, or alternatively consist essentially of, or alternatively consist of a fusion protein, which:
 (a) has the formula Y-X, wherein X is IL-2 and Y is IL-7 (i.e. wherein IL-7 is fused to the NH2-terminus of IL-2, said fusion protein being designated IL-7/IL-2);
 (b) has the formula X-Y, wherein X is IL-2 and Y is IL-15 (i.e. wherein IL-15 is fused to the COOH-terminus of IL-2, said fusion protein being designated IL-2/IL-15), or has the formula Y-X, wherein X is IL-2 and Y is IL-15 (i.e. wherein IL-15 is fused to the NH2-terminus of IL-2, said fusion protein being designated IL-15/IL-2);
 (c) has the formula X-Y, wherein X is IL-2 and Y is IL-18 (i.e. wherein IL-18 is fused to the COOH-terminus of IL-2, said fusion protein being designated IL-2/IL-18);
 (d) has the formula Y-X, wherein X is IL-2 and Y is IL-21 (i.e. wherein IL-21 is fused to the NH2-terminus of IL-2, said fusion protein being designated IL-21/IL-2);
 (e) has the formula Y-X, wherein X is IL-2 and Y is IFNg (i.e. wherein IFNg is fused to the NH2-terminus of IL-2, said fusion protein being designated IFNg/IL-2);
 (f) has the formula X-Y, wherein X is IL-15 and Y is IL-7 (i.e. wherein IL-15 is fused to the NH2 terminus of IL-7, said fusion protein being designed IL-15/IL-7);
 (g) has the formula X-Y, wherein X is IL-15 and Y is IL-18 (i.e. wherein IL-18 is fused to the COOH-terminus of IL-15, said fusion protein being designated IL-15/IL-18), or has the formula Y-X, wherein X is IL-15 and Y is IL-18 (i.e. wherein IL-18 is fused to the NH2-terminus of IL-15, said fusion protein being designated IL-18/IL-15);
 (h) has the formula X-Y, wherein X is IL-15 and Y is IL-21 (i.e. wherein IL-21 is fused to the COOH-terminus of IL-15, said fusion protein being designated IL-15/IL-21), or has the formula Y-X, wherein X is IL-15 and Y is IL-21 (i.e. wherein IL-21 is fused to the NH2 terminus of IL-15, said fusion protein being designated IL-21/IL-15); or
 (i) has the formula X-Y, wherein X is IL-18 and Y is IL-21 (i.e. wherein IL-21 is fused to the COOH-terminus of IL-18, said fusion protein being designated IL-18/IL-21) or has the formula Y-X, wherein X is IL-18 and Y is IL-21 (i.e. wherein IL-21 is fused to the NH2-terminus of IL-18, said fusion protein being designated IL-21/IL-18).

As mentioned before, the present invention encompasses fusion proteins involving full-length pre-processed forms, as well as mature processed forms, fragments thereof and variants of each or both of the X and Y entities, including allelic as well as non-naturally occurring variants. In addition to naturally-occurring allelic variants of the X and/or Y entities that may exist in the population, the skilled artisan will further appreciate that changes (i.e. one or more deletions, additions and/or substitutions of one or more amino acid) can be introduced by mutation using classic or recombinant techniques to effect random or targeted mutagenesis. A suitable variant in use in the present invention preferably has an amino acid sequence having a high degree of homology with the amino acid sequence of the corresponding native cytokine. In one embodiment, the amino acid sequence of the variant cytokine in use in the fusion protein of the invention is at least 70%, at least about 75%, at least about 80%, at least about 90%, preferably at least about 95%, more preferably at least about 97% and even more preferably at least about 99% identical to the corresponding native sequence.

Percent identities between amino acid or nucleic acid sequences can be determined using standard methods known to those of skill in the art. For instance for determining the percentage of homology between two amino acid sequences, the sequences are aligned for optimal comparison purposes. The amino acid residues at corresponding amino acid positions are then compared. Gaps can be introduced in one or both amino acid sequence(s) for optimal alignment and non-homologous sequences can be disregarded for comparison purposes. When a position in the first sequence is occupied by the same amino acid residue as the corresponding position in the second sequence, then the sequences are identical at that position. The percent identity between the two sequences is a function of the number of identical positions shared by the sequences, taking into account the number of gaps which need to be introduced for optimal alignment and the length of each gap. The comparison of sequences and determination of percent identity and similarity between two sequences can be accomplished using a mathematical algorithm (e.g. Computational Molecular Biology, 1988, Ed Lesk A M, Oxford University Press, New York; Biocomputing: Informatics and Genome Projects, 1993, Ed Smith D. W., Academic Press, New York; Computer Analysis of Sequence Data, 1994, Eds Griffin A. M. and Griffin H. G., Human Press, New Jersey; Sequence Analysis Primer, 1991, Eds Griskov M. and Devereux J., Stockton Press, New York). Moreover, various computer programs are available to determine percentage identities between amino acid sequences and between nucleic acid sequences, such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.).

Suitable variants of X and/or Y entities for use in the present invention are biologically active and retain at least one of the activities described herein in connection with the corresponding native cytokine. Preferably, the therapeutic effect (e.g. anti-tumor activity, by-pass of tumor-induced immune anergy) is preserved, although a given function of the native cytokine(s) may be positively or negatively affected to some degree, e.g. with variants exhibiting reduced cytotoxicity or enhanced biological activity. Amino acids that are essential for a given function can be identified by methods known in the art, such as by site-directed mutagenesis. Amino acids that are critical for binding a partner/substrate (e.g. a receptor) can also be determined by structural analysis such as crystallization, nuclear magnetic resonance and/or photo-affinity labeling. The resulting variant can be tested for biological activity in assays such as those described above.

For example, in one class of functional variants, one or more amino acid residues are conservatively substituted. A "conservative amino acid substitution" is one in which the amino acid residue in the native polypeptide is replaced with an amino acid residue having a similar side chain. Families of amino acid residues having similar side chains have been defined in the art (see for example the matrix of FIGS. 84 and 85 of the Atlas of Protein Sequence and Structure, 1978, Vol. 5, ed. M. O. Dayhoff, National Biomedical Research Foundation, Washington, D.C.). Typically, substitutions are regarded as conservative when the replacement, one for another, is among the aliphatic amino acids Ala, Val, Leu, and Ile; the hydroxyl residues Ser and Thr; the acidic residues Asp and Glu; the amide residues Asn and Gln; the basic residues Lys and Arg; or the aromatic residues Phe and Tyr. Alternatively, in another embodiment, mutations can be introduced randomly along all or part of a cytokine coding sequence, such as by saturation mutagenesis, and the resultant mutant can be screened for its biological activity as described herein to identify mutants that retain at least therapeutic activity.

In accordance with the present invention, particularly important are IL-2 variants which exhibit a reduced cytotoxicity as compared to the corresponding native IL-2. Suitable IL-2 variants include without limitation those described in European patent EP 673 257 and U.S. Pat. No. 5,229,109 (incorporated by reference herein) having an amino acid substitution within the B alpha helix formed by residues 33-46 of the human IL-2. Specific examples of low toxic IL-2 variants include the variant F42K having the phenyl alanine residue in position 42 of the native IL-2 substituted by a lysine residue, or the variant R38A having the arginine residue in position 38 of the native IL-2 substituted by an alanine residue. Further IL-2 variants suitable for use in the present invention also include those described in WO 99/60128 and by Shanafelt et al. (2000, Nat Biotech 18, 1197-1202) (incorporated by reference herein). Specific examples include the variant D20I having the aspartic acid in position 20 of the native IL-2 substituted by an isoleucine residue, the variant N88G having the asparagine in position 88 of the native IL-2 substituted by a glycine residue, the variant N88R having the asparagine in position 88 of the native IL-2 substituted by an arginine residue and the variant Q126M having the glutamine in position 126 of the native IL-2 substituted by a methionine residue or any combination thereof. The term "in position" as used herein encompasses the meaning that the respective cytokine variant is mutated at a site corresponding that of the position in the respectively cited native cytokine.

Suitable IL-15 variants for use in the present invention include without limitation those described in WO 02/63044 relating to genetic variants of human IL-15 gene as well as any variant of IL-15 which is mutated at one or more amino acid residue(s) which interferes with the binding to alpha chain of IL-15 receptor (e.g. those described by Bernard et al. (2004, J. Biol. Chem. 279, 24313-22 with a special preference for variants L45E, S51D, L52D, E64K, N65K and I68D, where the mutation positions are indicated by reference to Bernard et al. with +1 corresponding to the first residue of the mature IL-15).

In the context of the present invention, particularly important are IL-18 variants which exhibit an enhanced biological activity as compared to the corresponding native IL-18. Suitable IL-18 variants include without limitation those described by Kim et al. (2002, J. Biol. Chem. 277, 10998-11003) and Kim et al. (2001, Proc. Natl. Acad. Sci. USA 98, 3304-3309) (incorporated by reference herein), and more particularly the variant E42A having the glutamic acid residue in position 42 of the native IL-18 substituted by an alanine residue or the variant K89A having the lysine residue in position 89 of the native IL-18 substituted by an alanine residue or a variant combining both substitutions. Preferably, the IL-18 comprising fusion proteins of the present invention involve a mutated IL-18 having the lysine in position 89 of the native IL-18 substituted by an alanine residue (K89A).

Moreover, as mentioned above, the term IL-18 as used herein encompasses both proIL-18 and mature IL-18. According to one and preferred embodiment, the IL-18 polypeptide used in the present invention is a pro-IL-18 (i.e. comprising its endogenous prosequence), especially when it is fused to the NH2 terminus of the other cytokine partner. But, the use of an IL-18 entity (e.g. mature IL-18) comprising an heterologous (with respect to IL-18) prosequence can also be envisaged. According to another embodiment, the IL-18 polypeptide used in the present invention lacks its prosequence, especially when it is fused to the COOH terminus of the other cytokine partner.

Although the X and Y entities can be directly fused in the fusion protein of the invention, it is however preferred to use a linker peptide for joining X and Y. The purpose of the linker is to allow the correct formation, folding and/or functioning of each of the X and Y entities. It should be sufficiently flexible and sufficiently long to achieve that purpose. Preferably, the coding sequence of the linker may be chosen such that it encourages translational pausing and therefore independent folding of the X and Y entities. A person skilled in the art will be able to design suitable linkers in accordance with the invention. The present invention is, however, not limited by the form, size or number of linker sequences employed. Multiple copies of the linker sequence of choice may be inserted between X and Y. The only requirement for the linker sequence is that it functionally does not adversely interfere with the folding and/or functioning of the individual entities of the fusion protein. For example, a suitable linker is 5 to 50 amino acid long and may comprise amino acids such as glycine, serine, threonine, asparagine, alanine and proline (see for example Wiederrecht et al., 1988, Cell 54, 841; Dekker et al., 1993, Nature 362, 852; Sturm et al., 1988, Genes and Dev. 2, 1582; Aumailly et al., 1990 FEBS Lett. 262, 82). Repeats comprising serine and glycine residues are preferred in the context of the invention. A specific example of suitable linkers consists of two or three or more (e.g. up to eight) copies of the sequence Gly-Gly-Gly-Gly-Ser (GGGGS). It will be evident that the invention is not limited to the use of this particular linker.

The invention further includes fusion proteins which comprise, or alternatively consist essentially of, or alternatively consist of an amino acid sequence which is at least 70%, 75%, 80%, 90%, 95%, 97%, 99% homologous or even better 100% homologous (identical) to all or part of any of the amino acid sequences recited in SEQ ID NO: 1-19.

The sequence recited in SEQ ID NO:1 corresponds to the fusion between human IL7 and human IL-2, with the human IL-7 extending from amino acid residue 1 to amino acid residue 177, the linker peptide extending from amino acid residue 178 to amino acid residue 192, and the human IL-2 extending from amino acid residue 193 to amino acid residue 345. The sequence recited in SEQ ID NO: 2 corresponds to the fusion between murine IL7 and murine IL-2, with the murine IL-7 extending from amino acid residue 1 to amino acid residue 154, the linker peptide extending from amino acid residue 155 to amino acid residue 164, and the murine IL-2 extending from amino acid residue 165 to amino acid residue 333.

The sequence recited in SEQ ID NO:3 corresponds to the fusion between human IL-2 and human IL-15, with the human IL-2 extending from amino acid residue 1 to amino acid residue 153, the linker peptide extending from amino acid residue 154 to amino acid residue 168, and the human IL-15 extending from amino acid residue 169 to amino acid residue 330. The sequence recited in SEQ ID NO:4 corresponds to the fusion between human IL-15 and human IL-2, with the human IL-15 extending from amino acid residue 1 to amino acid residue 162, the linker peptide extending from amino acid residue 163 to amino acid residue 177, and the human IL-2 extending from amino acid residue 178 to amino acid residue 330. The sequence recited in SEQ ID NO:5 corresponds to the fusion between the signal peptide of human IL-2, human IL-15 and human IL-2, with the signal peptide of human IL-2 extending from amino acid residue 1 to amino acid residue 20, the human IL-15 extending from amino acid residue 21 to amino acid residue 182, the linker peptide extending from amino acid residue 183 to amino acid residue 197, and the human IL-2 extending from amino acid residue 198 to amino acid residue 350. The sequence recited in SEQ ED NO:6 corresponds to the fusion between murine IL-2 and murine IL-15, with the murine IL-2 extending from amino acid residue 1 to amino acid residue 169, the linker peptide extending from amino acid residue 170 to amino acid residue 179, and the murine IL-15 extending from amino acid residue 180 to amino acid residue 324. The sequence recited in SEQ ID NO: 7 corresponds to the fusion between murine IL-15 and murine IL-2, with the murine IL-15 extending from amino acid residue 1 to amino acid residue 145, the linker peptide extending from amino acid residue 146 to amino acid residue 155, and the murine IL-2 extending from amino acid residue 156 to amino acid residue 324.

The sequence recited in SEQ ID NO: 8 corresponds to the fusion between human IL-2 and human IL-18 (pro-IL-18), with the human IL-2 extending from amino acid residue 1 to amino acid residue 153, the linker peptide extending from amino acid residue 154 to amino acid residue 168, and the human pro-IL-18 extending from amino acid residue 169 to amino acid residue 361. The sequence recited in SEQ ID NO: 9 corresponds to the fusion between human IL-2 and the variant K89A of human pro-IL-18, with the human IL-2 extending from amino acid residue 1 to amino acid residue 153, the linker peptide extending from amino acid residue 154 to amino acid residue 168, and the variant of human pro-IL-18 extending from amino acid residue 169 to amino acid residue 361 with the amino acid residue 257 being an alanine instead of a lysine in the native IL-18. The sequence recited in SEQ ID NO: 10 corresponds to the fusion between human IL-2 and human mature IL-18, with the human IL-2 extending from amino acid residue 1 to amino acid residue 153, the linker peptide extending from amino acid residue 154 to amino acid residue 168, and the human mature IL-18 extending from amino acid residue 169 to amino acid residue 325. The sequence recited in SEQ ID NO: 11 corresponds to the fusion between human IL-2 and the variant K89A of human mature IL-18, with the human IL-2 extending from amino acid residue 1 to amino acid residue 153, the linker peptide extending from amino acid residue 154 to amino acid residue 168, and the variant of human mature IL-18 extending from amino acid residue 169 to amino acid residue 325 with the amino acid residue 221 being an alanine instead of a lysine in the native IL-18. The sequence recited in SEQ ID NO: 12 corresponds to the fusion between murine IL-2 and murine pro-IL-18, with the murine IL-2 extending from amino acid residue 1 to amino acid residue 169, the linker peptide extending from amino acid residue 170 to amino acid residue 179, and the murine pro-IL-18 extending from amino acid residue 180 to amino acid residue 371. The sequence recited in SEQ ID NO: 13 corresponds to the fusion between murine IL-2 and the variant K89A of the murine IL-18, with the murine IL-2 extending from amino acid residue 1 to amino acid residue 169, the linker peptide extending from amino acid residue 170 to amino acid residue 179, and the variant of the murine IL-18 extending from amino acid residue 180 to amino acid residue 371 with the amino acid residue 266 being an alanine instead of a lysine in the native IL-18. The sequence recited in SEQ ID NO: 14 corresponds to the fusion between murine IL-2 and murine mature IL-18, with the murine IL-2 extending from amino acid residue 1 to amino acid residue 169, the linker peptide extending from amino acid residue 170 to amino acid residue 179 and the murine mature IL-18 extending from amino acid residue 180 to amino acid residue 336. The sequence recited in SEQ ID NO: 15 corresponds to the fusion between murine IL-2 and the variant K89A of the murine mature IL-18, with the murine IL-2 extending from amino acid residue 1 to amino acid residue 169, the linker peptide extending from amino acid residue 170 to amino acid residue 179 and the variant of the murine mature IL-18 extending from amino acid residue 180 to amino acid residue 336, with the amino acid residue 231 being an alanine instead of a lysine in the native IL-18.

The sequence recited in SEQ ID NO: 16 corresponds to the fusion between human IL-21 and human IL-2, with the human IL-21 extending from amino acid residue 1 to amino acid residue 179, the linker peptide extending from amino acid residue 180 to amino acid residue 194 and the human IL-2 extending from amino acid residue 195 to amino acid residue 347. The sequence recited in SEQ ID NO: 17 corresponds to the fusion between murine IL-21 and murine IL-2, with the murine IL-21 extending from amino acid residue 1 to amino acid residue 146, the linker peptide extending from amino acid residue 147 to amino acid residue 156 and the murine IL-2 extending from amino acid residue 157 to amino acid residue 325.

The sequence recited in SEQ ID NO: 18 corresponds to the fusion between human IFNg and human IL-2, with the human IFNg extending from amino acid residue 1 to amino acid residue 166, the linker peptide extending from amino acid residue 167 to amino acid residue 181 and the human IL-2 extending from amino acid residue 182 to amino acid residue 334. The sequence recited in SEQ ID NO: 19 corresponds to the fusion between murine IFNg and murine IL-2, with the murine IFNg extending from amino acid residue 1 to amino acid residue 155, the linker peptide extending from amino acid residue 156 to amino acid residue 165 and the murine IL-2 extending from amino acid residue 166 to amino acid residue 334.

In the context of the present invention, a protein "consists of" an amino acid sequence when the protein does not contain any amino acids but the recited amino acid sequence. A protein "consists essentially of" an amino acid sequence when such an amino acid sequence is present together with only a few additional amino acid residues, typically from about 1 to about 50 or so additional residues. A protein "comprises" an amino acid sequence when the amino acid sequence is at least part of the final (i.e. mature) amino acid sequence of the protein. Such a protein can have a few up to several hundred additional amino acids residues. Such additional amino acid residues can be naturally associated with each or both entities contained in the fusion or heterologous amino acid/peptide sequences (heterologous with respect to the respective entities). Such additional amino acid residues may play a role in processing of the fusion protein from a precursor to a mature form, may facilitate protein trafficking, prolong or shorten protein half-life or facilitate manipulation of the fusion protein for assay or production, among other things. Preferably, the fusion proteins of the invention comprise a signal peptide at the NH2-terminus in order to promote secretion in the host cell or organism. For example, the endogenous signal peptide (i.e. naturally present in the cytokine present at the NH2 terminus of said fusion) can be used or alternatively a suitable heterologous (with respect to the cytokine in question) signal peptide sequence can be added to the cytokine entity present at the NH2 terminus of the fusion or inserted in replacement of the endogenous one. Suitably, when IL-15 is present at the NH2 terminus of the fusion protein of the invention, a heterologous peptide signal (heterologous with respect to IL-15) can be added to or can replace the native signal of IL-15, in order to promote or increase secretion in a given host. Suitable heterologous signal peptides include without limitation the signal peptides of IL-2 and signal peptide of immunoglobulins (Ig) such as the signal peptide of the Kappa light chain of a mouse IgG (Meazza et al., 2000, Int. J. Cancer 87, 574; Susuki et al., 2001, J. Leukoc. Biol. 69, 531). An illustrative example of this embodiment is provided by the fusion protein recited in SEQ ID NO: 5. Alternatively, it is also possible to use the endogenous IL-15 peptide signal either the short or the long form thereof (Kuryus et al., 2000, J. Biol. Chem. 275, 30653). In addition, the fusion protein may also be fused to a tag peptide, for example, a peptide that facilitates identification and/or purification.

In the context of the invention, the fusion proteins of the invention can comprise cytokine entities of any origin, i.e. any human or animal source (including canine, avian, bovine, murine, ovine, feline, porcine, etc). Although "chimeric" fusion proteins are also encompassed by the invention (e.g. one cytokine entity of human origin and the other of an animal source), it is preferred that each entity be of the same origin (e.g. both from humans).

The fusion proteins of the present invention can be produced by standard techniques. Polypeptide and DNA sequences for each of the cytokines involved in the fusion protein of the present invention are published in the art, as are methods for obtaining expression thereof through recombinant or chemical synthetic techniques. In another embodiment, a fusion-encoding DNA sequence can be synthesized by conventional techniques including automated DNA synthesizers. Then, the DNA sequence encoding the fusion protein may be constructed in a vector and operably linked to a regulatory region capable of controlling expression of the fusion protein in a host cell or organism. Techniques for cloning DNA sequences for instance in viral vectors or plasmids are known to those of skill in the art (Sambrook et al, 2001, "Molecular Cloning. A Laboratory Manual", Laboratory Press, Cold Spring Harbor N.Y.). The fusion protein of the invention can be purified from cells that have been transformed to express it as described below.

The fusion protein of the present invention may be characterized by having the usual activity of at least one of the X and Y entities forming the fusion or it may be further characterized by having a biological activity greater than simply the additive functions of X and Y. This enhancement of activity provides an enhanced therapeutic effects, thus allowing to reduce dosing regimens, improve compliance and maintenance therapy, to reduce emergency situations and to improve quality of life. In certain cases, the fusion molecule of the present invention may also unexpectedly provide an activity different from that expected by the presence of X or Y. For example, one specific unexpected activity highlighted in connection with this invention is the ability of IL-2/IL-18 (IL-2/proIL-18 or IL-2/mature IL-18) and IL-7/IL-2 fusions to activate the maturation of dendritic cells, for example for the purpose of enhancing a nonspecific immune response against tumor or viral antigens. Another activity discovered for the IL-2/IL-18 fusion (IL-2/proIL-18 or IL-2/mature IL-18) is to activate NKT cells, e.g. for the purpose of enhancing a non-specific immune response against tumor or viral antigens. Another unexpected effect discovered in connection with this invention is the limited cytotoxicity (AICD activity) provided by IL-2/IL-18 (IL-2/proIL-18 or IL-2/mature IL-18) and IL-7/IL-2 fusions as compared upon administration of the individual cytokine(s) in a given organism, which can be used e.g. for reducing cytotoxic side effects.

Further included in the scope of the present invention are novel peptide fragments of the fusion proteins of the invention, and especially of those recited in any of SEQ ID NO: 1-19. As used herein, a fragment comprises at least 8, 15, 20, 50 or more contiguous amino acid residues from the fusion proteins disclosed herein. Such fragments can be chosen based on their ability to retain one or more of the therapeutic and/or biological activities of the fusion protein or could be chosen for their ability to perform a function, e.g. to bind a substrate or to act as an immunogen. Suitable peptide fragments are typically those comprising a domain or motif of the fusion protein containing novel immunogenic structures. Predicted immunogenic sites are readily identifiable by computer programs well known and readily available to those of skill in the art. Particularly important are peptide fragments overlapping the fusion site between the X and Y entities. Peptide fragments of the fusion protein of the invention can also be synthesized using known protein synthesis methods.

The present invention also provides a nucleic acid molecule encoding the fusion protein of the invention.

Within the context of the present invention, the term "nucleic acid" and "polynucleotide" are used interchangeably and define a polymer of nucleotides of any length, either deoxyribonucleotide (DNA) molecules (e.g., cDNA or genomic DNA) and ribonucleotide (RNA) molecules (e.g., mRNA) and analogs of the DNA or RNA generated using nucleotide analogs (see U.S. Pat. No. 5,525,711, U.S. Pat. No. 4,711,955 or EPA 302 175 as examples of nucleotide analogs). If present, modifications to the nucleotide structure may be imparted before or after assembly of the polymer. The sequence of nucleotides may also be interrupted by non-nucleotide elements. The nucleic acid molecule may be further modified after polymerization, such as by conjugation with a labeling component. The nucleic acid, especially DNA, can be double-stranded or single-stranded, but preferably is double-stranded DNA. Single-stranded nucleic acids can be the coding strand (sense strand) or the non-coding strand (anti-sense strand).

The nucleic acid molecules of the invention include, but are not limited to, the sequence encoding the fusion protein alone, but may comprise additional non-coding sequences, for example introns and non-coding 5' and 3' sequences that play a role in transcription, mRNA processing (including splicing and polyadenylation signals), ribosome binding and mRNA stability. For example, the nucleic acid molecule of the invention can contain less than about 5 kb, 4 kb, 3 kb, 2 kb, 1 kb, 0.5 kb or 0.1 kb of nucleotide sequences which naturally flank (i.e. sequences located at the 5' and 3' ends) or are present within the genomic DNA encoding X and/or Y entities.

According to a preferred embodiment, the present invention provides nucleic acid molecules which comprise, or alternatively consist essentially of, or alternatively consist of a nucleotide sequence encoding all or part of an amino acid sequence encoding a fusion protein which is at least about 70%, at least about 75%, at least about 80%, at least about 90%, at least about 95%, preferably at least about 97%, more preferably at least about 99% homologous or even more preferably 100% homologous to any of the amino acid sequences shown in SEQ ID NO: 1-19.

In another embodiment, a nucleic acid molecule of the invention comprises a nucleic acid molecule which is a complement of all or part of a nucleotide sequence encoding the fusion protein shown in any of SEQ ID NO: 1-19. A nucleic acid molecule which is complementary to the nucleotide sequence of the present invention is one which is sufficiently complementary such that it can hybridize to the fusion-encoding nucleotide sequence under stringent conditions, thereby forming a stable duplex. Such stringent conditions are known to those skilled in the art. A preferred, non-limiting example of stringent hybridization conditions are hybridization in 6 times sodium chloride/sodium citrate (SSC) at about 45° C., followed by one or more washes in 0.2 times SSC, 0.1% SDS at 50-65° C. In one embodiment, the invention pertains to antisense nucleic acid to the nucleic acid molecules of the invention. The antisense nucleic acid can be complementary to an entire coding strand, or to only a portion thereof.

In still another embodiment, the invention encompasses variants of the above-described nucleic acid molecules of the invention, e.g. that encode variants of the fusion proteins that are described above. The variation(s) encompassed by the present invention can be created by introducing one or more nucleotide substitutions, additions and/or deletions into the nucleotide sequence by standard techniques, such as site-directed mutagenesis and PCR-mediated mutagenesis. Following mutagenesis, the variant nucleic acid molecule can be expressed recombinantly as described herein and the activity of the resulting protein can be determined using, for example, assays described herein. Alternatively, the nucleic acid molecule of the invention can be altered to provide preferential codon usage for a specific host cell (for example E. coli; Wada et al., 1992, Nucleic Acids Res. 20, 2111-2118). The invention further encompasses nucleic acid molecules that differ due to the degeneracy of the genetic code and thus encode for example the same fusion protein as any of those shown in SEQ ID NO: 1-19.

Another embodiment of the invention pertains to fragments of the nucleic acid molecule of the invention, e.g. restriction endonuclease and PCR-generated fragments. Such fragments can be used as probes, primers or fragments encoding an immunogenic portion of the fusion protein.

The nucleic acid molecules of the present invention can be generated using the sequence information provided herein. The nucleic acid encoding each of the X and Y entities can be cloned or amplified using cDNA or, alternatively, genomic DNA, as a template and appropriate probes or oligonucleotide primers according to standard molecular biology techniques (e.g., as described in Sambrook, et al. "Molecular Cloning: A Laboratory Manual", Cold Spring Harbor Laboratory Press, Cold Spring Harbor, N.Y., 2001) or standard PCR amplification techniques based on sequence data accessible in the art (such as those provided above in connection with the fusion proteins of the invention or those provided in the Examples part). Fusing of the X sequence to the Y sequence may be accomplished as described in the Examples below or by conventional techniques. For example, the X and Y-encoding sequences can be ligated together in-frame either directly or through a sequence encoding a peptide linker. The X-encoding sequence can also be inserted directly into a vector which contains the Y-encoding sequence, or vice versa. Alternatively, PCR amplification of the X and Y-encoding sequences can be carried out using primers which give rise to complementary overhangs which can subsequently be annealed and re-amplified to generate a fusion gene sequence.

Also provided by the present invention is a vector containing the nucleic acid molecule of the invention.

The term "vector" as used herein refers to both expression and nonexpression vectors and includes viral as well as non-viral vectors, including autonomous self-replicating circular plasmids. Where a recombinant microorganism or cell culture is described as hosting an "expression vector," this includes both extrachromosomal circular DNA and DNA that has been incorporated into the host chromosome(s). Preferred vectors of the invention are expression vectors. An expression vector contains multiple genetic elements positionally and sequentially oriented, i.e., operatively linked with other necessary elements such that nucleic acid molecule in the vector encoding the fusion proteins of the invention can be transcribed, and when necessary, translated in the host cells.

Any type of vector can be used in the context of the present invention, whether of plasmid or viral origin, whether it is an integrating or nonintegrating vector. Such vectors are commercially available or described in the literature. Particularly important in the context of the invention are vectors for use in gene therapy (i.e. which are capable of delivering the nucleic acid molecule to a target cell) as well as expression vectors for use in recombinant techniques (i.e. which are capable for example of expressing the nucleic acid molecule of the invention in cultured host cells).

The vectors of the invention can function in prokaryotic or eukaryotic cells or in both (shuttle vectors). Suitable vectors include without limitation vectors derived from bacterial plasmids, bacteriophages, yeast episomes, artificial chromosomes, such as BAC, PAC, YAC, or MAC, and vectors derived from viruses such as baculoviruses, papovaviruses (e.g. SV40), herpes viruses, adenoviruses, adenovirus-associated viruses (AAV), poxviruses, foamy viruses, and retroviruses. Vectors may also be derived from combinations of these sources such as those derived from plasmid and bacteriophage genetic elements, e.g. cosmids and phagemids. Viral vectors can be replication-competent, conditionally replicative or replication-defective. In the case in which viral replication is defective, replication will occur in host cells providing functions that complement the defects.

Examples of suitable plasmids include but are not limited to those derived from pBR322 (Gibco BRL), pUC (Gibco BRL), pBluescript (Stratagene), p Poly (Lathe et al., 1987, Gene 57, 193-201), pTrc (Amann et al., 1988, Gene 69, 301-315) and pET 11d (Studier et al., 1990, Gene Expression Technology: Methods in Enzymology 185, 60-89). It is well known that the four of the plasmid can affect the expression efficiency, and it is preferable that a large fraction of the vector be in supercoiled form. Examples of vectors for expression in yeast (e.g. *S. cerevisiae*) include pYepSec1 (Baldari et al., 1987, EMBO J. 6, 229-234), pMFa (Kujan et al., 1982, Cell 30, 933-943), pJRY88 (Schultz et al., 1987, Gene 54, 113-123), and pYES2 (Invitrogen Corporation, San Diego, Calif.). The vectors of the invention can also be derived from baculoviruses to be expressed in cultured insect cells (e.g. Sf 9 cells).

According to a preferred embodiment of the invention, the nucleic acid molecules described herein are expressed by using mammalian expression vectors. Examples of mammalian expression vectors include pREP4, pCEP4 (Invitrogene), pCI (Promega), pCDM8 (Seed, 1987, Nature 329, 840) and pMT2PC (Kaufman et al., 1987, EMBO J. 6, 187-195). The expression vectors listed herein are provided by way of example only of some well-known vectors available to those of ordinary skill in the art. The person of ordinary skill in the art would be aware of other vectors suitable for maintenance, propagation or expression of the nucleic acid molecules described herein.

Moreover, the vector of the present invention may also comprise a marker gene in order to select or to identify the transfected cells (e.g. by complementation of a cell auxotrophy or by antibiotic resistance), stabilising elements (e.g. cer sequence; Summers and Sherrat, 1984, Cell 36, 1097-1103), integrative elements (e.g. LTR viral sequences and transposons) as well as elements providing a self-replicating function and enabling the vector to be stably maintained in cells, independently of the copy number of the vector in the cell. Markers include tetracycline or ampicillin-resistance genes for prokaryotic host cells and dihydrofolate reductase or neomycin resistance for eukaryotic host cells. However, any marker that provides selection for a phenotypic trait will be effective. The self-replicating function may be provided by using a viral origin of replication and providing one or more viral replication factors that are required for replication mediated by that particular viral origin (WO 95/32299). Origins of replication and any replication factors may be obtained from a variety of viruses, including Epstein-Barr virus (EBV), human and bovine papilloma viruses and papovavirus BK.

Particularly preferred vectors of the present invention are viral vectors and especially adenoviral vectors, which have a number of well-documented advantages as vectors for gene therapy. The adenoviral genome consists of a linear double-stranded DNA molecule of approximately 36 kb carrying more than about thirty genes necessary to complete the viral cycle. The early genes are divided into 4 regions (E1 to E4) that are essential for viral replication (Pettersson and Roberts, 1986, In Cancer Cells (Vol 4): DNA Tumor Viruses, Botchan and Glodzicker Sharp Eds pp 37-47, Cold Spring Harbor Laboratory, Cold Spring Harbor, N.Y.; Halbert et al., 1985, J. Virol. 56, 250-257) with the exception of the E3 region, which is believed dispensable for viral replication based on the observation that naturally-occurring mutants or hybrid viruses deleted within the E3 region still replicate like wild-type viruses in cultured cells (Kelly and Lewis, 1973, J. Virol. 12, 643-652). The E1 gene products encode proteins responsible for the regulation of transcription of the viral genome. The E2 gene products are required for initiation and chain elongation in viral DNA synthesis. The proteins encoded by the E3 prevent cytolysis by cytotoxic T cells and tumor necrosis factor (Wold and Gooding, 1991, Virology 184, 1-8). The proteins encoded by the E4 region are involved in DNA replication, late gene expression and splicing and host cell shut off (Halbert et al., 1985, J. Virol. 56, 250-257). The late genes (L1 to L5) encode in their majority the structural proteins constituting the viral capsid. They overlap at least in part with the early transcription units and are transcribed from a unique promoter (MLP for Major Late Promoter). In addition, the adenoviral genome carries at both extremities cis-acting 5' and 3' ITRs (Inverted Terminal Repeat) and the encapsidation region, both essential for DNA replication. The ITRs harbor origins of DNA replication whereas the encapsidation region is required for the packaging of adenoviral DNA into infectious particles.

As used herein, the term "adenoviral vector" encompasses vector DNA as well as viral particles generated thereof by conventional technologies.

The adenoviral vectors for use in accordance with the present invention, preferably infects human cells. It can be derived from any human or animal source, in particular canine (e.g. CAV-1 or CAV-2; Genbank ref CAV1GENOM and CAV77082 respectively), avian (Genbank ref AAVEDS-DNA), bovine (such as BAV3; Seshidhar Reddy et al., 1998, J. Virol. 72, 1394-1402), murine (Genbank ref ADRMUS-MAV1), ovine, feline, porcine or simian adenovirus or alternatively from a hybrid thereof. Any serotype can be employed from the adenovirus serotypes 1 through 51. For instance, an adenovirus can be of subgroup A (e.g. serotypes 12, 18, and 31), subgroup B (e.g. serotypes 3, 7, 11, 14, 16, 21, 34, and 35), subgroup C (e.g. serotypes 1, 2, 5, and 6), subgroup D (e.g. serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. However, the human adenoviruses of the B or C sub-group are preferred and especially adenoviruses 2 (Ad2), 5 (Ad5) and 35 (Ad35). Generally speaking, adenoviral stocks that can be employed as a source of the cited adenovirus are currently available from the American Type Culture Collection (ATCC, Rockville, Md.), or from any other source. Moreover, such adenoviruses have been the subject of numerous publications describing their sequence, organization and biology, allowing the artisan to apply them. Adenoviral vectors, methods of producing adenoviral vectors, and methods of using adenoviral vectors are disclosed, for example in U.S. Pat. No. 6,133,028 and U.S. Pat. No. 6,040,174, U.S. Pat. No. 6,110,735, U.S. Pat. No. 6,399,587, WO 00/50573 and EP 1016711 for group C adenoviral vectors and for example in U.S. Pat. No. 6,492,169 and WO 02/40665 for non-group C adenoviral vectors.

In one embodiment, the adenoviral vector of the present invention is replication-competent. The term "replication-competent" as used herein refers to an adenoviral vector capable of replicating in a host cell in the absence of any trans-complementation. In the context of the present invention, this term also encompasses replication-selective or conditionally-replicative adenoviral vectors which are engineered to replicate better or selectively in cancer or hyperproliferative host cells. Examples of such replication-competent adenoviral vectors are well known in the art and readily available to those skill in the art (see, for example, Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727).

Replication-competent adenoviral vectors according to the invention can be a wild-type adenovirus genome or can be derived therefrom by introducing modifications into the viral genome, e.g., for the purpose of generating a conditionally-replicative adenoviral vector. Such modification(s) include the deletion, insertion and/or mutation of one or more nucleotide(s) in the coding sequences and/or the regulatory sequences. Preferred modifications are those that render said replication-competent adenoviral vector dependent on cellular activities specifically present in a tumor or cancerous cell. In this regard, viral gene(s) that become dispensable in tumor cells, such as the genes responsible for activating the cell cycle through p53 or Rb binding, can be completely or partially deleted or mutated. By way of illustration, such conditionally-replicative adenoviral vectors can be engineered by the complete deletion of the adenoviral MB gene encoding the 55 kDa protein or the complete deletion of the MB region to abrogate p53 binding (see for example U.S. Pat. No. 5,801,029 and U.S. Pat. No. 5,846,945). This prevents the virus from inactivating tumor suppression in normal cells, which means that the virus cannot replicate. However, the virus will replicate and lyse cells that have shut off p53 or Rb expression through oncogenic transformation. As another example, the complete deletion of the E1A region makes the adenoviral vector dependent on intrinsic or IL-6-induced E1A-like activities. Optionally, an inactivating mutation may also be introduced in the E1A region to abrogate binding to the Rb. Rb defective mutation/deletion is preferably introduced within the E1A CR1 and/or CR2 domain (see for example WO00/24408). In a second strategy optionally or in combination to the first approach, native viral promoters controlling transcription of the viral genes can be replaced with tissue or tumor-specific promoters. By way of illustration, regulation of the E1A and/or the E1B genes can be placed under the control of a tumor-specific promoter such as the PSA, the kallikrein, the probasin, the AFP, the a-fetoprotein or the telomerase reverse transcriptase (TERT) promoter (see for example U.S. Pat. No. 5,998,205, WO 99/25860, U.S. Pat. No. 5,698,443 and WO 00/46355) or a cell-cycle specific promoter such as E2F-1 promoter (WO00/15820 and WO01/36650). Particularly preferred in this context is the exemplary vector designated ONYX-411 which combines a Rb defective deletion of 8 amino acid residues within the MA CR2 domain and the use of E2F-1 promoter to control expression of both the E1A and E4 viral genes.

According to another and preferred embodiment, the adenoviral vector of the invention is replication-defective. Replication-defective adenoviral vectors are known in the art and can be defined as being deficient in one or more regions of the adenoviral genome that are essential to the viral replication (e.g., E1, E2 or E4 or combination thereof), and thus unable to propagate in the absence of trans-complementation (e.g., provided by either complementing cells or a helper virus). The replication-defective phenotype is obtained by introducing modifications in the viral genome to abrogate the function of one or more viral gene(s) essential to the viral replication. Preferred replication-defective vectors are E1-deleted, and thus defective in E1 function. Such E1-deleted adenoviral vectors include those described in U.S. Pat. No. 6,063,622; U.S. Pat. No. 6,093,567; WO 94/28152; WO 98/55639 and EP 974 668 (the disclosures of all of these publications are hereby incorporated herein by reference). A preferred E1 deletion covers approximately the nucleotides (nt) 459 to 3328 or 459 to 3510, by reference to the sequence of the human adenovirus type 5 (disclosed in the Genbank under the accession number M 73260 and in Chroboczek et al., 1992, Virol. 186, 280-285).

Furthermore, the adenoviral backbone of the vector may comprise modifications (e.g. deletions, insertions or mutations) in additional viral region(s), to abolish the residual synthesis of the viral antigens and/or to improve long-term expression of the nucleic acid molecules in the transduced cells (see for example WO 94/28152; Lusky et al., 1998, J. Virol 72, 2022-2032; Yeh et al., 1997, FASEB J. 11, 615-623). In this context, the present invention contemplates the use of adenoviral vectors lacking E1, or E1 and E2, or E1 and E3, or E1 and E4, or E1 and E2 and E3, or E1 and E2 and E4, or E1 and E3 and E4, or E1 and E2 and E3 and E4 functions. An adenoviral vector defective for E2 function may be deleted of all or part of the E2 region (preferably within the E2A or alternatively within the E2B or within both the E2A and the E2B regions) or comprises one or more mutations, such as the thermosensitive mutation of the DBP (DNA Binding Protein) encoding gene (Ensinger et al., J. Virol. 10 (1972), 328-339). The adenoviral vector may also be deleted of all or part of the E4 region (see, for example, EP 974 668 and WO 00/12741). An exemplary E4 deletion covers approximately the nucleotides from position 32994 to position 34998, by reference to the sequence of the human adenovirus type 5. In addition, deletions within the non-essential E3 region (e.g. from Ad5 position 28597 to position 30469) may increase the cloning capacity, but it may be advantageous to retain the E3 sequences coding for gp19k, 14.7K and/or RID allowing to escape the host immune system (Gooding et al., 1990, Critical Review of Immunology 10, 53-71) and inflammatory reactions (EP 00 440 267.3). It is also conceivable to employ a minimal (or gutless) adenoviral vector which lacks all functional genes including early (E1, E2, E3 and E4) and late genes (L1, L2, L3, L4 and L5) with the exception of cis-acting sequences (see for example Kovesdi et al., 1997, Current Opinion in Biotechnology 8, 583-589; Yeh and Perricaudet, 1997, FASEB 11, 615-623; WO 94/12649; and WO 94/28152). The replication-deficient adenoviral vector may be readily engineered by one skilled in the art, taking into consideration the required minimum sequences, and is not limited to these exemplary embodiments.

The nucleic acid molecule of the present invention can be inserted in any location of the adenoviral genome, with the exception of the cis-acting sequences. Preferably, it is inserted in replacement of a deleted region (E1, E3 and/or E4), with a special preference for the deleted E1 region. In addition, the expression cassette may be positioned in sense or antisense orientation relative to the natural transcriptional direction of the region in question.

A retroviral vector is also suitable in the context of the present invention. Retroviruses are a class of integrative viruses which replicate using a virus-encoded reverse transcriptase, to replicate the viral RNA genome into double stranded DNA which is integrated into chromosomal DNA of the infected cells. The numerous vectors described in the literature may be used within the framework of the present invention and especially those derived from murine leukemia viruses, especially Moloney (Gilboa et al., 1988, Adv. Exp. Med. Biol. 241, 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (U.S. Pat. No. 5,747,323). The nucleic acid molecule of the invention can be inserted downstream of the encapsidation sequence, preferably in opposite direction relative to the retroviral genome.

A poxyiral vector is also suitable in the context of the present invention. Poxviruses are a group of complex enveloped viruses that distinguish from the above-mentioned viruses by their large DNA genome and their cytoplasmic site of replication. The genome of several members of poxyiridae has been mapped and sequenced. It is a double-stranded DNA of approximately 200 kb coding for about 200 proteins of which approximately 100 are involved in virus assembly. In the context of the present invention, a poxyiral vector may be obtained from any member of the poxyiridae, in particular canarypox, fowlpox and vaccinia virus, the latter being preferred. Suitable vaccinia viruses include without limitation the Copenhagen strain (Goebel et al., 1990, Virol. 179, 247-266 and 517-563; Johnson et al., 1993, Virol. 196, 381-401), the Wyeth strain and the modified Ankara (MVA) strain (Antoine et al., 1998, Virol. 244, 365-396). The general conditions for constructing poxvirus comprising a nucleic acid molecule are well known in the art (see for example EP 83 286; EP 206 920 for Copenhagen vaccinia viruses and Mayr et al., 1975, Infection 3, 6-14; Sutter and Moss, 1992, Proc. Natl. Acad. Sci. USA 89, 10847-10851, U.S. Pat. No. 6,440,422 for MVA viruses). The nucleic acid molecule of the present invention is preferably inserted within the poxyiral genome in a non-essential locus, such as non-coding intergenic regions or any gene for which inactivation or deletion does not significantly impair viral growth and replication. Thymidine kinase gene is particularly appropriate for insertion in Copenhagen vaccinia viruses (Hruby et al., 1983, Proc. Natl. Acad. Sci. USA 80, 3411-3415; Weir et al., 1983, J. Virol. 46, 530-537). As far as MVA is concerned, insertion of the nucleic acid molecule can be performed in any of the excisions I to VII, and preferably in excision II or III (Meyer et al., 1991, J. Gen. Virol. 72, 1031-1038; Sutter et al., 1994, Vaccine 12, 1032-1040) or in D4R locus. For fowlpox virus, although insertion within the thymidine kinase gene may be considered, the nucleic acid molecule is preferably introduced into a non-coding intergenic region (see for example EP 314 569 and U.S. Pat. No. 5,180,675). One may also envisage insertion in an essential viral locus provided that the defective function be supplied in trans, via a helper virus or by expression in the producer cell line. Suitable poxyiral vectors can be readily generated from wild type poxviruses available in recognized collections such as ATCC (fowlpox ATCC VR-251, monkey pox ATCC VR-267, swine pox ATCC VR-363, canarypox ATCC VR-111, cowpox ATCC VR-302) or ICTV (Canberra, Australia) (Copenhagen virus code 58.1.1.0.001; GenBank accession number M35027).

According to a preferred embodiment, the vectors of the invention comprise the nucleic acid molecule of the invention in a form suitable for its expression in a host cell or organism, which means that the nucleic acid molecule is placed under the control of one or more regulatory sequences, selected on the basis of the vector type and/or host cell, which is operatively linked to the nucleic acid molecule to be expressed. As used herein, the term "regulatory sequence" refers to any sequence that allows, contributes or modulates the functional regulation of the nucleic acid molecule, including replication, duplication, transcription, splicing, translation, stability and/or transport of the nucleic acid or one of its derivative (i.e. mRNA) into the host cell or organism. In the context of the invention, this term encompasses promoters, enhancers and other expression control elements (e.g., polyadenylation signals and elements that affect mRNA stability). "Operably linked" is intended to mean that the nucleic acid molecule of interest is linked to the regulatory sequence(s) in a manner which allows for expression of the nucleic acid molecule (e.g., in a host cell or organism). It will be appreciated by those skilled in the art that the design of the expression vector can depend on such factors as the choice of the host cell to be transformed, the level of expression of protein desired, etc.

Regulatory sequences include promoters which direct constitutive expression of a nucleic acid molecule in many types of host cell and those which direct expression of the nucleotide sequence only in certain host cells (e.g., tissue-specific regulatory sequences) or in response to specific events or exogenous factors (e.g. by temperature, nutrient additive, hormone or other ligand).

Suitable regulatory sequences useful in the context of the present invention include, but are not limited to, the left promoter from bacteriophage lambda, the lac, TRP, and TAC promoters from *E. coli*, the early and late promoters from SV40, the cytomegalovirus (CMV) immediate early promoter or enhancer (Boshart et al., 1985, Cell 41, 521-530), the adenovirus early and late promoters, the phosphoglycero kinase (PGK) promoter (Hitzeman et al., 1983, Science 219, 620-625; Adra et al., 1987, Gene 60, 65-74), the thymidine kinase (TK) promoter of herpes simplex virus (HSV)-1 and retroviral long-terminal repeats (e.g. MoMuLV and Rous sarcoma virus (RSV) LTRs). Suitable promoters useful to drive expression of the nucleic acid molecule of the invention in a poxyiral vector include the 7.5K, H5R, TK, p28, p11 or K1L promoters of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxyiral promoters.

Inducible promoters are regulated by exogenously supplied compounds, and include, without limitation, the zinc-inducible metallothionein (MT) promoter (Mc Ivor et al., 1987, Mol. Cell. Biol. 7, 838-848), the dexamethasone (Dex)-inducible mouse mammary tumor virus (MMTV) promoter, the T7 polymerase promoter system (WO 98/10088), the ecdysone insect promoter (No et al., 1996, Proc. Natl. Acad. Sci. USA 93, 3346-3351), the tetracycline-repressible promoter (Gossen et al., 1992, Proc. Natl. Acad. Sci. USA 89, 5547-5551), the tetracycline-inducible promoter (Kim et al., 1995, J. Virol. 69, 2565-2573), the RU486-inducible promoter (Wang et al., 1997, Nat. Biotech. 15, 239-243 and Wang et al., 1997, Gene Ther. 4, 432-441) and the rapamycin-inducible promoter (Magari et al., 1997, J. Clin. Invest. 100, 2865-2872).

The regulatory sequences in use in the context of the present invention can also be tissue-specific to drive expression of the nucleic acid molecule in the tissues where therapeutic benefit is desired. Exemplary liver-specific regulatory sequences include but are not limited to those of HMG-CoA reductase (Luskey, 1987, Mol. Cell. Biol. 7, 1881-1893); sterol regulatory element 1 (SRE-1; Smith et al., 1990, J. Biol. Chem. 265, 2306-2310); albumin (Pinkert et al., 1987, Genes Dev. 1, 268-277); phosphoenol pyruvate carboxy kinase (PEPCK) (Eisenberger et al., 1992, Mol. Cell. Biol. 12, 1396-1403); human C-reactive protein (CRP) (Li et al., 1990, J. Biol. Chem. 265, 4136-4142); human glucokinase (Tanizawa et al., 1992, Mol. Endocrinology. 6, 1070-1081); cholesterol 7-alpha hydroylase (CYP-7) (Lee et al., 1994, J. Biol. Chem. 269, 14681-14689); alpha-1 antitrypsin (Ciliberto et al., 1985, Cell 41, 531-540); insulin-like growth factor binding protein (IGFBP-1) (Babajko et al., 1993, Biochem Biophys. Res. Comm. 196, 480-486); human transferrin (Mendelzon et al., 1990, Nucl. Acids Res. 18, 5717-5721); collagen type I (Houglum et al., 1994, J. Clin. Invest. 94, 808-814) and FIX (U.S. Pat. No. 5,814,716) genes. Exemplary prostate-specific regulatory sequences include but are not limited to those of the prostatic acid phosphatase (PAP) (Balms et al., 1994, Biochim. Biophys. Acta. 1217, 188-194); prostatic secretory protein 94 (PSP 94) (Nolet et al., 1991, Biochim. Biophys. Acta 1089, 247-249); prostate specific antigen complex (Kasper et al., 1993, J. Steroid Biochem. Mol. Biol. 47, 127-135); human glandular kallikrein (hgt-1) (Lilja et al., 1993, World J. Urology 11, 188-191) genes. Exemplary pancreas-specific regulatory sequences include but are not limited to those of pancreatitis associated protein (PAP) promoter (Dusetti et al., 1993, J. Biol. Chem. 268, 14470-14475); elastase 1 transcriptional enhancer (Kruse et al., 1993, Genes and Development 7, 774-786); pancreas specific amylase and elastase enhancer/promoter (Wu et al., 1991, Mol. Cell. Biol. 11, 4423-4430; Keller et al., 1990, Genes & Dev. 4, 1316-1321); pancreatic cholesterol esterase gene promoter (Fontaine et al., 1991, Biochemistry 30, 7008-7014) and the insulin gene promoter (Edlund et al., 1985, Science 230, 912-916). Exemplary neuron-specific regulatory sequences include but are not limited to neuron-specific enolase (NSE) (Forss-Petter et al., 1990, Neuron 5, 187-197) and the neurofilament (Byrne and Ruddle, 1989, Proc. Natl. Acad. Sci. USA 86, 5473-5477) gene promoters. Exemplary regulatory sequences for expression in the brain include but are not limited to the neurofilament heavy chain (NF-H) promoter (Schwartz et al., 1994, J. Biol. Chem. 269, 13444-13450). Exemplary lymphoid-specific regulatory sequences include but are not limited to the human CGL1/granzyme B promoter (Hanson et al., 1991, J. Biol. Chem. 266, 24433-24438); terminal deoxy transferase (TdT), lymphocyte specific tyrosine protein kinase (p561ck) promoters (Lo et al., 1991, Mol. Cell. Biol. 11, 5229-5243); the human CD2 promoter/enhancer (Lake et al., 1990, EMBO J. 9, 3129-3136), the human NK and T cell specific activation (NKG5) (Houchins et al., 1993, Immunogenetics 37, 102-107), T cell receptor (Winoto and Baltimore, 1989, EMBO J. 8, 729-733) and immunoglobulin (Banerji et al., 1983, Cell 33, 729-740; Queen and Baltimore, 1983, Cell 33, 741-748) promoters. Exemplary colon-specific regulatory sequences include but are not limited to pp 60c-src tyrosine kinase (Talamonti et al., 1993, J. Clin. Invest 91, 53-60); organ-specific neoantigens (OSNs), mw 40 kDa (p40) (Ilantzis et al., 1993, Microbiol. Immunol. 37, 119-128); and colon specific antigen-P promoter (Sharkey et al., 1994, Cancer 73, 864-877) promoters. Exemplary regulatory sequences for expression in mammary gland and breast cells include but are not limited to the human alpha-lactalbumin (Thean et al., 1990, British J. Cancer. 61, 773-775) and milk whey (U.S. Pat. No. 4,873,316) promoters. Exemplary muscle-specific regulatory sequences include but are not limited to SM22 (WO 98/15575; WO 97/35974), the desmin (WO 96/26284), mitochondrial creatine kinase (MCK) promoters, and the chimeric promoter disclosed in EP 1310561. Exemplary lung-specific regulatory sequences include but are not limited to the CFTR and surfactant promoters.

Additional promoters suitable for use in this invention can be taken from genes that are preferentially expressed in proliferative tumor cells. Such genes can be identified for example by display and comparative genomic hybridization (see for example U.S. Pat. Nos. 5,759,776 and 5,776,683). Exemplary tumor specific promoters include but are not limited to the promoters of the MUC-1 gene overexpressed in breast and prostate cancers (Chen et al., 1995, J. Clin. Invest. 96, 2775-2782), of the Carcinoma Embryonic Antigen (CEA)-encoding gene overexpressed in colon cancers (Schrewe et al., 1990, Mol. Cell. Biol. 10, 2738-2748), of the ERB-2 encoding gene overexpressed in breast and pancreas cancers (Harris et al., 1994, Gene Therapy 1, 170-175), of the alpha-foetoprotein gene overexpressed in liver cancers (Kanai et al., 1997, Cancer Res. 57, 461-465), of the telomerase reverse transcriptase (TERT) (WO99/27113, WO 02/053760 and Horikawa et al., 1999, Cancer Res. 59, 826), hypoxia-responsive element (HRE), autocrine motility factor receptor, L plasmin and hexokinase II.

Those skilled in the art will appreciate that the regulatory elements controlling the expression of the nucleic acid molecule of the invention may further comprise additional elements for proper initiation, regulation and/or termination of transcription and translation into the host cell or organism. Such additional elements include but are not limited to non coding exon/intron sequences, transport sequences, secretion signal sequences, nuclear localization signal sequences, IRES, polyA transcription termination sequences, tripartite leader sequences, sequences involved in replication or integration. Illustrative examples of introns suitable in the context of the invention include those isolated from the genes encoding alpha or beta globin (i.e. the second intron of the rabbit beta globin gene; Green et al., 1988, Nucleic Acids Res. 16, 369; Karasuyama et al., 1988, Eur. J. Immunol. 18, 97-104), ovalbumin, apolipoprotein, immunoglobulin, factor IX, and factor VIII, the SV40 16S/19S intron (Okayma and Berg, 1983, Mol. Cell. Biol. 3, 280-289) as well as synthetic introns such as the intron present in the pCI vector (Promega Corp, pCI mammalian expression vector E1731) made of the human beta globin donor fused to the mouse immunoglobin acceptor or. Where secretion of the fusion protein is desired, appropriate secretion signals are incorporated into the vector. The signal sequence can be endogenous to the fusion protein (e.g. endogenous to the X or Y entity) or heterologous to both X and Y entities involved in the fusion protein. The person of ordinary skill in the art would be aware of the numerous regulatory sequences that are useful in expression vectors.

A preferred embodiment of the invention is directed to a E1- and E3-deleted replication-defective adenoviral vector comprising the nucleic acid molecule of the invention inserted in replacement of the E1 region and placed under the control of the CMV promoter.

In addition, the vector of the invention can further comprise one or more transgenes (i.e. a gene of interest to be expressed together with the nucleic acid molecule of the invention in a host cell or organism). Desirably, the expression of the transgene has a therapeutic or protective activity to the disease or illness condition for which the vector of the present invention is being given. Suitable transgenes include without limitation genes encoding (i) tumor proliferation inhibitors and/or (ii) at least one specific antigen against which an immune response is desired. In a preferred form of the present invention, the transgene product and the fusion protein act synergistically in the induction of immune responses or in providing a therapeutic (e.g. antitumoral) benefit. Accordingly, such combinations are not only suitable for immunoprophylaxis of diseases, but surprisingly also for immunotherapy of diseases such as viral, bacterial or parasitic infections, and also chronic disorders such as cancers.

Tumor proliferation inhibitors act by directly inhibiting cell growth, or killing the tumor cells. Representative examples of tumor proliferation inhibitors include toxins and suicide genes. Representative examples of toxins include without limitation ricin (Lamb et al., 1985, Eur. J. Biochem. 148, 265-270), diphtheria toxin (Tweten et al., 1985, J. Biol. Chem. 260, 10392-10394), cholera toxin (Mekalanos et al., 1983, Nature 306, 551-557; Sanchez and Holmgren, 1989, Proc. Natl. Acad. Sci. USA 86, 481-485), gelonin (Stirpe et al., 1980, J. Biol. Chem. 255, 6947-6953), antiviral protein (Barbieri et al., 1982, Biochem. J. 203, 55-59; Irvin et al., 1980, Arch. Biochem. Biophys. 200, 418-425), tritin, *Shigella* toxin (Calderwood et al., 1987, Proc. Natl. Acad. Sci. USA 84, 4364-4368; Jackson et al., 1987, Microb. Path. 2, 147-153) and *Pseudomonas* exotoxin A (Carroll and Collier, 1987, J. Biol. Chem. 262, 8707-8711).

<<Suicide genes>> can be defined in the context of the present invention as any gene encoding an expression product able to transform an inactive substance (prodrug) into a cytotoxic substance, thereby giving rise to cell death. The gene encoding the TK HSV-1 constitutes the prototype member of the suicide gene family (Caruso et al., 1993, Proc. Natl. Acad. Sci. USA. 90, 7024-7028; Culver et al., 1992, Science 256, 1550-1552). While the TK, polypeptide is non-toxic as such, it catalyzes the transformation of nucleoside analogs (prodrug) such as acyclovir or ganciclovir. The transformed nucleosides are incorporated into the DNA chains which are in the process of elongation, cause interruption of said elongation and therefore inhibition of cell division. A large number of suicide gene/prodrug combinations are currently available. Those which may more specifically be mentioned are rat cytochrome p450 and cyclophosphophamide (Wei et al., 1994, Human Gene Ther. 5, 969-978), *Escherichia coli* (*E. coli*) purine nucleoside phosphorylase and 6-methylpurine deoxyribonucleoside (Sorscher et al., 1994, Gene Therapy 1, 223-238), *E. coli* guanine phosphoribosyl transferase and 6-thioxanthine (Mzoz et al., 1993, Human Gene Ther. 4, 589-595). However, in a preferred embodiment, the vector of the invention comprises a suicide gene encoding a polypeptide having a cytosine deaminase (CDase) or a uracil phosphoribosyl transferase (UPRTase) activity or both CDase and UPRTase activities, which can be used with the prodrug 5-fluorocytosine (5-FC). Suitable CDase encoding genes include but are not limited to the *Saccharomyces cerevisiae* FCY1 gene (Erbs et al., 1997, Curr. Genet. 31, 1-6; WO 93/01281) and the *E. coli* codA gene (EP 402 108). Suitable UPRTase encoding genes include but are not limited to those from *E. coli* (upp gene; Anderson et al., 1992, Eur. J. Biochem. 204, 51-56), and *Saccharomyces cerevisiae* (FUR-1 gene; Kern et al., 1990, Gene 88, 149-157). Preferably, the CDase encoding gene is derived from the FCY1 gene and the UPRTase encoding gene is derived from the FUR-1 gene. Particularly important is the use of a fusion protein which encodes a two domain enzyme possessing both CDase and UPRTase activities (FCU-1) as described in WO 99/54481 (incorporated herein by reference).

Specific antigens are preferably those susceptible to confer an immune response, specific and/or nonspecific, antibody and/or cell-mediated, against a given pathogen (virus, bacterium, fungus or parasite) or against a non-self antigen (e.g. a tumor-associated antigen). Preferably, the selected antigen comprises an epitope that binds to, and is presented onto the cell surface by MHC class I proteins. Representative examples of specific antigens include without limitation:

- antigen(s) of the Hepatitis B surface antigen are well known in the art and include, inter alia, those PreS1, Pars2 S antigens set forth described in European Patent applications EP 414 374; EP 304 578, and EP 198 474.
- Antigens of the Hepatitis C virus including any immunogenic antigen or fragment thereof selected from the group consisting of the Core (C), the envelope glycoprotein E1, E2, the non-structural polypeptide NS2, NS3, NS4 (NS4a and/or NS4b), NS5 (NS5a and/or NS5b) or any combination thereof (e.g. NS3 and NS4, NS3 and NS4 and NS5b)
- Antigen(s) of the HIV-1 virus, especially gp120 and gp160 (as described WO 87/06260).
- Antigen(s) derived from the Human Papilloma Virus (HPV) considered to be associated with genital warts (HPV 6 or HPV 11 and others), and cervical cancer (HPV16, HPV18, HPV 31, HPV-33 and others). Particularly important HPV antigens are selected among the group consisting of E5, E6, E7, L1, and L2 either individually or in combination (see for example WO 94/00152, WO 94/20137, WO 93/02184, WO 90/10459, and WO 92/16636). Particularly important in the context of the invention are membrane anchored forms of non oncogenic variants of the early HPV-16 E6 and/or E7 antigens (as described in WO 99/03885) that are particularly suitable to achieve an anti-tumoral effect against an HPV-associated cancer.
- antigens from parasites that cause malaria. For example, preferred antigens from Plasmodia falciparum include RTS (WO 93/10152), and TRAP (WO 90/01496). Other plasmodia antigens that are likely candidates are *P. falciparum*. MSP1, AMA1, MSP3, EBA, GLURP, RAPT, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in other *Plasmodium* species.
- Other suitable antigens include tumour-associated antigens such as those associated with prostrate, breast, colorectal, lung, pancreatic, renal, liver, bladder, sarcoma or melanoma cancers. Exemplary antigens include MAGE 1, 3 and MAGE 4 or other MAGE antigens (WO 99/40188), PRAME, BAGE, Lage (also known as NY Eos 1) SAGE and HAGE (WO 99/53061) or GAGE (Robbins and Kawakami, 1996. Current Opinions in Immunol. 8, pps 628-636). Other suitable tumor-associated antigens include those known as prostase, including Prostate specific antigen (PSA), PAP, PSCA, PSMA. Prostase nucleotide sequence and deduced polypeptide sequence and homologs are disclosed in Ferguson, et al. (1999, Proc. Natl. Acad. Sci. USA. 96, 3114-3119) and WO 98/12302 WO 98/20117 and WO 00/04149. Other suitable tumour-associated antigens include those associated with breast cancer, such as BRCA-1, BRCA-2 and MUC-1 (see for example WO 92/07000).

The transgene in use in the present invention is placed under the control of appropriate regulatory elements to permit its expression in the selected host cell or organism in either a constitutive or inducible fashion. The choice of such regulatory elements is within the reach of the skilled artisan. It is preferably selected from the group consisting of constitutive, inducible, tumor-specific and tissue-specific promoters as described above in connection with the expression of the fusion protein of the present invention. In one example, the transgene is placed under control of the CMV promoter to ensure high level expression.

The transgene in use in the present invention can be inserted in any location of the vector. According to one alternative, it is placed preferably not in close proximity of the nucleic acid molecule of the invention. According to another alternative it can be placed in antisense orientation with respect to the nucleic acid molecule, in order to avoid transcriptional interference between the two expression cassettes. For example, in an adenoviral genome, the transgene can be inserted in a different deleted region with respect to the nucleic acid molecule of the invention (E1, E3 and/or E4) or in the same deleted region as said nucleic acid molecule but in antisense orientation to one another.

Introducing the nucleic acid molecule of the invention into a vector backbone can proceed by any genetic engineering strategy appropriate in the art for any kind of vectors such as by methods described in Sambrook et al. (2001, Molecular Cloning—A Laboratory Manual, Cold Spring Harbor Laboratory). Typically, for the introduction of the nucleic acid molecule into an adenoviral vector, a bacterial plasmid comprising the fusion-encoding nucleic acid molecule is engineered to replace an adenoviral gene required for replication or assembly (e.g. E1) with the substitute nucleic acid molecule. The plasmid is then used as a shuttle vector, and combined with a second plasmid containing the complementary portion of the adenovirus genome, permitting homologous recombination to occur by virtue of overlapping adenovirus sequences in the two plasmids. The recombination can be done directly in a suitable mammalian host (such as 293 as described in Graham and Prevect, 1991, Methods in Molecular Biology, Vol 7 "Gene Transfer and Expression Protocols"; Ed E. J. Murray, The Human Press Inc, Clinton, N.J.), or else in yeast YAC clones or E. coli (as described in WO 96/17070). The completed adenovirus genome is subsequently transfected into mammalian host cells for replication and viral encapsidation.

The present invention also encompasses vectors of the invention or particles thereof that have been modified to allow preferential targeting of a particular target cell. A characteristic feature of targeted vectors/particles of the invention (of both viral and non-viral origins, such as polymer- and lipid-complexed vectors) is the presence at their surface of a targeting moiety capable of recognizing and binding to a cellular and surface-exposed component. Such targeting moieties include without limitation chemical conjugates, lipids, glycolipids, hormones, sugars, polymers (e.g. PEG, polylysine, PEI and the like), peptides, polypeptides (for example JTS1 as described in WO 94/40958), oligonucleotides, vitamins, antigens, lectins, antibodies and fragments thereof. They are preferably capable of recognizing and binding to cell-specific markers, tissue-specific markers, cellular receptors, viral antigens, antigenic epitopes or tumor-associated markers. In this regard, cell targeting of adenoviruses can be carried out by genetic modification of the viral gene encoding the capsid polypeptide present on the surface of the virus (e.g. fiber, penton and/or pIX). Examples of such modifications are described in literature (for example in Wickam et al., 1997, J. Viral. 71, 8221-8229; Amberg et al., 1997, Virol. 227, 239-244; Michael et al., 1995, Gene Therapy 2, 660-668; WO 94/10323, EP 02 360204 and WO 02/96939). To illustrate, inserting a sequence coding for EGF within the sequence encoding the adenoviral fiber will allow to target EGF receptor expressing cells. The modification of poxyiral tropism can also be achieved as described in EP 1 146 125. Other methods for cell specific targeting can be achieved by the chemical conjugation of targeting moieties at the surface of a viral particle.

In another embodiment, the present invention relates to infectious viral particles comprising the above-described nucleic acid molecules or vectors of the present invention.

The invention also relates to a process for producing an infectious viral particle, comprising the steps of:
(a) introducing the viral vector of the invention into a suitable cell line,
(b) culturing said cell line under suitable conditions so as to allow the production of said infectious viral particle, and
(c) recovering the produced infectious viral particle from the culture of said cell line, and
(d) optionally purifying said recovered infectious viral particle.

The vector containing the nucleic acid molecule of the invention can be introduced into an appropriate cell line for propagation or expression using well-known techniques readily available to the person of ordinary skill in the art. These include, but are not limited to, microinjection of minute amounts of DNA into the nucleus of a cell (Capechi et al., 1980, Cell 22, 479-488), $CaPO_4$-mediated transfection (Chen and Okayama, 1987, Mol. Cell Biol. 7, 2745-2752), DEAE-dextran-mediated transfection, electroporation (Chu et al., 1987, Nucleic Acid Res. 15, 1311-1326), lipofection/liposome fusion (Feigner et al., 1987, Proc. Natl. Acad. Sci. USA 84, 7413-7417), particle bombardment (Yang et al., 1990, Proc. Natl. Acad. Sci. USA 87, 9568-9572), gene guns, transduction, infection (e.g. with an infective viral particle), and other techniques such as those found in Sambrook, et al. (Molecular Cloning: A Laboratory Manual, Cold Spring Harbor Laboratory, Cold Spring Harbor Laboratory Press, Cold Spring Harbor, N.Y., 2001).

When the vector of the invention is defective, the infectious particles are usually produced in a complementation cell line or via the use of a helper virus, which supplies in trans the non functional viral genes. For example, suitable cell lines for complementing adenoviral vectors include the 293 cells (Graham et al., 1997, J. Gen. Virol. 36, 59-72) as well as the PER-C6 cells (Fallaux et al., 1998, Human Gene Ther. 9, 1909-1917) commonly used to complement the E1 function. Other cell lines have been engineered to complement doubly defective adenoviral vectors (Yeh et al., 1996, J. Virol. 70, 559-565; Krougliak and Graham, 1995, Human Gene Ther. 6, 1575-1586; Wang et al., 1995, Gene Ther. 2, 775-783; Lusky et al., 1998, J. Virol. 72, 2022-2033; WO94/28152 and WO97/04119). The infectious viral particles may be recovered from the culture supernatant but also from the cells after lysis and optionally are further purified according to standard techniques (chromatography, ultracentrifugation in a cesium chloride gradient as described for example in WO 96/27677, WO 98/00524, WO 98/22588, WO 98/26048, WO 00/40702, EP 1016700 and WO 00/50573).

The invention also relates to host cells which comprise the nucleic acid molecules, vectors or infectious viral particles of the invention described herein. For the purpose of the invention, the term "host cell" should be understood broadly without any limitation concerning particular organization in tissue, organ, or isolated cells. Such cells may be of a unique type of cells or a group of different types of cells and encompass cultured cell lines, primary cells and proliferative cells.

Host cells therefore include prokaryotic cells, lower eukaryotic cells such as yeast, and other eukaryotic cells such as insect cells, plant and higher eukaryotic cells, such as vertebrate cells and, with a special preference, mammalian (e.g. human or non-human) cells. Suitable mammalian cells include but are not limited to hematopoïetic cells (totipotent, stem cells, leukocytes, lymphocytes, monocytes, macrophages, APC, dendritic cells, non-human cells and the like), pulmonary cells, tracheal cells, hepatic cells, epithelial cells, endothelial cells, muscle cells (e.g. skeletal muscle, cardiac muscle or smooth muscle) or fibroblasts. Preferred host cells include Escherichia coli, Bacillus, Listeria, Saccharomyces, BHK (baby hamster kidney) cells, MDCK cells (Madin-Darby canine kidney cell line), CRFK cells (Crandell feline kidney cell line), CV-1 cells (African monkey kidney cell line), COS (e.g., COS-7) cells, chinese hamster ovary (CHO) cells, mouse NIH/3T3 cells, HeLa cells and Vero cells. Host cells also encompass complementing cells capable of complementing at least one defective function of a replication-defective vector of the invention (e.g. adenoviral vector) such as those cited above.

The host cell of the invention can contain more than one nucleic acid molecule, vector or infectious viral particle of the invention. Further it can additionally comprise a vector encoding a transgene, e.g. a transgene as described above. When more than one nucleic acid molecule, vector or infectious viral particle is introduced into a cell, the nucleic acid molecules, vectors or infectious viral particles can be introduced independently or co-introduced.

Moreover, according to a specific embodiment, the host cell of the invention can be further encapsulated. Cell encapsulation technology has been previously described (Tresco et al., 1992, ASAJO J. 38, 17-23; Aebischer et al., 1996, Human Gene Ther. 7, 851-860). According to said specific embodiment, transfected or infected eukaryotic host cells are encapsulated with compounds which form a microporous membrane and said encapsulated cells can further be implanted in vivo. Capsules containing the cells of interest may be prepared employing hollow microporous membranes (e.g. Akzo Nobel Faser AG, Wuppertal, Germany; Deglon et al. 1996, Human Gene Ther. 7, 2135-2146) having a molecular weight cutoff appropriate to permit the free passage of proteins and nutrients between the capsule interior and exterior, while preventing the contact of transplanted cells with host cells.

Still a further aspect of the present invention is a method for recombinantly producing the fusion protein, employing the vectors, infectious viral particles and/or host cells of the invention. The method for producing the fusion protein comprises introducing a vector or an infectious viral particle of the invention into a suitable host cell to produce a transfected or infected host cell, culturing in-vitro said transfected or infected host cell under conditions suitable for growth of the host cell, and thereafter recovering said fusion protein from said culture, and optionally, purifying said recovered fusion protein. It is expected that those skilled in the art are knowledgeable in the numerous expression systems available for expression of the fusion proteins of the invention in appropriate host cells.

The host cell of the invention is preferably produced by transfecting/infecting a host cell with one or more recombinant molecules, (e.g. a vector of the invention) comprising one or more nucleic acid molecules of the present invention. Recombinant DNA technologies can be used to improve expression of the nucleic acid molecule in the host cell by manipulating, for example, the number of copies of the nucleic acid molecule within a host cell, the efficiency with which the nucleic acid molecule is transcribed, the efficiency with which the resultant transcripts are translated, the efficiency of post-translational modifications and the use of appropriate selection. Recombinant techniques useful for increasing the expression of nucleic acid molecules of the present invention include, but are not limited to, the use of high-copy number vectors, addition of vector stability sequences, substitution or modification of one or more transcriptional regulatory sequences (e.g., promoters, operators, enhancers), substitution or modification of translational regulatory sequences (e.g., ribosome binding sites, Shine-Dalgamo sequences), modification of nucleic acid molecule of the present invention to correspond to the codon usage of the host cell, and deletion of sequences that destabilize transcripts.

Host cells of the present invention can be cultured in conventional fermentation bioreactors, flasks, and petri plates. Culturing can be carried out at a temperature, pH and oxygen content appropriate for a given host cell. No attempts to describe in detail the various methods known for the expression of proteins in prokaryote and eukaryote cells will be made here. In one embodiment, the vector is a plasmid carrying the fusion-encoding nucleic acid molecule in operative association with appropriate regulatory elements. Preferred host cells in use in the method of the invention are mammalian cell lines, yeast cells and bacterial cells.

Where the fusion protein is not secreted outside the producing cell or where it is not secreted completely, it can be recovered from the cell by standard disruption procedures, including freeze thaw, sonication, mechanical disruption, use of lysing agents and the like. If secreted, it can be recovered directly from the culture medium. The fusion protein can then be recovered and purified by well-known purification methods including ammonium sulfate precipitation, acid extraction, gel electrophoresis, reverse phase chromatography, size exclusion chromatography, ion exchange chromatography, affinity chromatography, phosphocellulose chromatography, hydrophobic-interaction chromatography, hydroxylapatite chromatography, lectin chromatography, or high performance liquid chromatography. The conditions and technology used to purify a particular fusion protein of the invention will depend on the synthesis method and on factors such as net charge, molecular weight, hydrophobicity, hydrophilicity and will be apparent to those having skill in the art. It is also understood that depending upon the host cell used for the recombinant production of the fusion proteins described herein, the fusion proteins can have various glycosylation patterns, or may be non-glycosylated (e.g. when produced in bacteria). In addition, the fusion protein may include an initial methionine in some cases as a result of a host-mediated process.

The fusion protein of the invention can be "purified" to the extent that it is substantially free of cellular material. The level of purification will be based on the intended use. The critical feature is that the preparation allows for the desired function of the fusion protein, even if in the presence of considerable amounts of other components. In some uses, "substantially free of cellular material" includes preparations of the fusion protein having less than about 30% (by dry weight) other proteins (i.e., contaminating proteins), preferably less than about 20% other proteins, more preferably less than about 10% other proteins, or even more preferably less than about 5% other proteins. When the fusion protein is recombinantly produced, it can also be substantially free of culture medium, i.e., culture medium represents less than about 20% of the volume of the protein preparation.

In another aspect, this invention provides a pharmaceutical composition comprising an effective amount of the fusion protein, the expression vector, the infectious viral particle, the host cell of the invention or any combination thereof (also referred herein to "active agents") and optionally a pharmaceutically acceptable vehicle. In a special case, the composition may comprise two or more active agents, which may differ by (i) the nature of the encoded fusion protein and/or (ii) the nature of the regulatory sequence used to express the fusion protein and/or (iii) the additional presence of a transgene and/or (iv) the vector backbone.

The compositions of the present invention may be used to protect or treat a mammal susceptible to, or suffering from a disease, by means of administering said composition by a variety of modes of administration including systemic, topical and localized administration. For systemic administration, injection is preferred, e.g. subcutaneous, intradermal, intramuscular, intravenous, intraperitoneal, intrathecal, intracardiac (such as transendocardial and pericardial), intratumoral, intravaginal, intrapulmonary, intranasal, intratracheal, intravascular, intraarterial, intracoronary, intracerebroventricular, transdermal (topical) or directly into a lymph node. Intramuscular, intradermal, intravenous, or intratumoral administration constitutes the preferred routes for systemic administration. Alternatively the composition of the present invention may be administered via a mucosal route, such as the oral/alimentary, nasal, intratracheal, intravaginal or intrarectal route. The preferred mucosal route of administration is via the nasal or intratracheal route.

As used herein the language "pharmaceutically acceptable vehicle" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the invention comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is preferably isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions (see for example the most current edition of Remington: The Science and Practice of Pharmacy, A. Gennaro, Lippincott, Williams & Wilkins). The pH of the composition of the invention is suitably adjusted and buffered in order to be appropriate for use in humans or animals, preferably at a physiological or slightly basic pH (between about pH 8 to about pH 9, with a special preference for pH 8.5). Suitable buffers include phosphate buffer (e.g. PBS), bicarbonate buffer and/or Tris buffer. A particularly preferred composition is formulated in 1M saccharose, 150 mM NaCl, 1 mM $MgCl_2$, 54 mg/l Tween 80, 10 mM Tris pH 8.5. Another preferred composition is formulated in 10 mg/ml mannitol, 1 mg/ml HSA, 20 mM Tris, pH 7.2, and 150 mM NaCl. These compositions are stable at −70° C. for at least six months.

The composition of the invention can be in various forms, e.g. in solid (e.g. powder, lyophilized form), or liquid (e.g. aqueous). In the case of solid compositions, the preferred methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

nebulized or aerosolized formulations also form part of this invention. Methods of intranasal administration are well known in the art, including the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this invention. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm. 51, 210-218). Representative examples of stabilizing components include polysorbate 80, L-arginine, polyvinylpyrrolidone, trehalose, and combinations thereof. Other stabilizing components especially suitable in plasmid-based compositions include hyaluronidase (which is thought to destabilize the extra cellular matrix of the host cells as described in WO 98/53853), chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile (see EP 890 362), nuclease inhibitors such as actin G (WO 99/56784) and cationic salts such as magnesium ($Mg^{2+}$) (EP 998 945) and lithium ($Li^+$) (WO 01/47563) and any of their derivatives. The amount of cationic salt in the composition of the invention preferably ranges from about 0.1 mM to about 100 mM, and still more preferably from about 0.1 mM to about 10 mM. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

The composition of the invention may also comprise one or more adjuvant(s) suitable for systemic or mucosal application in humans. Representative examples of useful adjuvants include without limitation alum, mineral oil emulsion such as Freunds complete and incomplete, lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72, 4931-4939; WO 98/56415), Escin, Digitonin, *Gypsophila* or *Chenopodium quinoa* saponins. Alternatively the composition of the invention may be formulated with conventional vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, and lipid-based particles, etc. The composition may also be formulated in the presence of cholesterol to form particulate structures such as liposomes.

The composition may be administered to patients in an amount effective, especially to enhance an immune response in an animal or human organism. As used herein, the term <<effective amount>> refers to an amount sufficient to realize a desired biological effect. For example, an effective amount for enhancing an immune response could be that amount necessary to cause activation of the immune system, for instance resulting in the development of an anti-tumor response in a cancerous patient (e.g. size reduction or regression of the tumor into which the composition has been injected and/or distant tumors). The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. For general guidance, a composition based on viral (e.g. adenoviral) particles may be formulated in the form of doses of between $10^4$ and $10^{14}$ in (infectious units), advantageously between $10^5$ and $10^{13}$ iu and preferably between $10^6$ and $10^{12}$ iu. The titer may be determined by conventional techniques. A composition based on vector plasmids may be formulated in the form of doses of between 1 μg to 100 mg, advantageously between 10 μg and 10 mg and preferably between 100 μg and 1 mg. A composition based on proteins may be formulated in the form of doses of between 10 ng to 100 mg. A preferred dose is from about 1 μg to about 10 mg of the therapeutic protein per kg body weight. The administration may take place in a single dose or a dose repeated one or several times after a certain time interval. In one preferred embodiment, the composition of the present invention is administered by injection using conventional syringes and needles, or devices designed for ballistic delivery of solid compositions (WO 99/27961), or needleless pressure liquid jet device (U.S. Pat. No. 4,596,556; U.S. Pat. No. 5,993,412).

The composition of the invention can be enclosed in ampoules, disposable syringes or multiple dose vials made of glass or plastic. In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the active agent (e.g., a fusion protein or infectious particles) in the required amount with one or a combination of ingredients enumerated above, followed by filtered sterilization.

The pharmaceutical composition of the invention may be employed in methods for treating or preventing a variety of diseases and pathologic conditions, including genetic diseases, congenital diseases and acquired diseases such as infectious diseases (e.g. viral and/or bacterial infections), cancer, immune deficiency diseases, and autoimmune diseases. Accordingly, the present invention also encompasses the use of the fusion protein, vector, infectious viral particle, host cell or composition of the invention for the preparation of a drug intended for treating or preventing such diseases, and especially cancer or an infectious disease.

The composition of the present invention is particularly intended for the preventive or curative treatment of disorders, conditions or diseases associated with cancer. The term "cancer" encompasses any cancerous conditions including diffuse or localized tumors, metastasis, cancerous polyps and pre-neoplastic lesions (e.g. dysplasies) as well as diseases which result from unwanted cell proliferation. A variety of tumors may be selected for treatment in accordance with the methods described herein. In general, solid tumors are preferred. Cancers which are contemplated in the context of the invention include without limitation glioblastoma, sarcoma, melanomas, mastocytoma, carcinomas as well as breast cancer, prostate cancer, testicular cancer, ovarian cancer, endometrial cancer, cervical cancer (in particular, those induced by a papilloma virus), lung cancer (e.g. lung carcinomas including large cell, small cell, squamous and adeno-carcinomas), renal cancer, bladder cancer, liver cancer, colon cancer, anal cancer, pancreatic cancer, stomach cancer, gastrointestinal cancer, cancer of the oral cavity, larynx cancer, brain and CNS cancer, skin cancer (e.g. melanoma and non-melanoma), blood cancer (lymphomas, leukemia, especially if they have developed in solid mass), bone cancer, retinoblastoma and thyroid cancer. In one preferred embodiment of the use of the invention, the composition is administered into or in close proximity to a solid tumor.

Other pathologic diseases and conditions are also contemplated in the context of the invention, especially infectious diseases associated with an infection by a pathogen such as fungi, bacteria, protozoa and viruses. Representative examples of viral pathogens include without limitation human immunodeficiency virus (e.g. HIV-1 or HIV-2), human herpes viruses (e.g. HSV1 or HSV2), cytomegalovirus, Rotavirus, Epstein Barr virus (EBV), hepatitis virus (e.g. hepatitis B virus, hepatitis A virus, hepatitis C virus and hepatitis E virus), varicella-zoster virus (VZV), paramyxoviruses, coronaviruses; respiratory syncytial virus, parainfluenza virus, measles virus, mumps virus, flaviviruses (e.g. Yellow Fever Virus, Dengue Virus, Tick-borne encephalitis virus, Japanese Encephalitis Virus), influenza virus, and preferably human papilloma viruses (e.g. HPV-6, 11, 16, 18, 31. 33). Representative examples of bacterial pathogens include *Neisseria* (e.g. *N. gonorrhea* and *N. meningitidis*); *Bordetella* (e.g. *B. pertussis, B. parapertussis* and *B. bronchiseptica*), *Mycobacteria* (e.g. *M. tuberculosis, M. bovis, M. leprae, M. avium, M. paratuberculosis, M. smegmatis*); *Legionella* (e.g. *L. pneumophila*); *Escherichia* (e.g. enterotoxic *E. coli*, enterohemorragic *E. coli*, enteropathogenic *E. coli*); *Vibrio* (e.g. *V. cholera*); *Shigella* (e.g. *S. sonnei, S. dysenteriae, S. flexnerii*); *Salmonella* (e.g. *S. typhi, S. paratyphi, S. choleraesuis, S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus, S. epidermidis*); *Enterococcus* (e.g. *E. faecalis, E. faecium*), *Clostridium* (e.g. *C. tetani, C. botulinum, C. difficile*); *Bacillus* (e.g. *B. anthracis*); *Corynebacterium* (e.g. *C. diphtheriae*), and *Chlamydia* (e.g. *C. trachomatis, C. pneumoniae, C. psittaci*). Representative examples of parasite pathogens include *Plasmodium* (e.g. *P. falciparum*), *Toxoplasma* (e.g. *T. gondii*) *Leshmania* (e.g. *L. major*), *Pneumocystis* (e.g. *P. carinii*), *Trichomonas* (e.g. *T. vaginalis*), *Schisostoma* (e.g. *S. mansoni*). Representative examples of fungi include *Candida* (e.g. *C. albicans*) and *Aspergillus*.

Examples of autoimmune diseases include, but are not limited to, multiple sclerosis (MS), scleroderma, rheumatoid arthritis, autoimmune hepatitis, diabetes mellitus, ulcerative colitis, Myasthenia gravis, systemic lupus erythematosus, Graves' disease, idiopathic thrombocytopenia purpura, hemolytic anemia, multiple myositis/dermatomyositis, Hashimoto's disease, autoimmune hypocytosis, Sjogren's syndrome, angitis syndrome and drug-induced autoimmune diseases (e.g., drug-induced lupus).

Moreover, as mentioned above, the fusion protein, nucleic acid molecule, vector, infectious particle, host cell and/or composition of the present invention can be used as an adjuvant to enhance the immune response of an animal or human organism to a particular antigen. This particular use of the present invention may be made in combination with one or more transgenes or transgene products as defined above, e.g. for purposes of immunotherapy. Preferably, the active agent (e.g. fusion protein, infectious particle or pharmaceutical composition of the invention) is administered in combination with one or more transgenes or transgene products. Accordingly, there is preferably also provided a composition comprising in combination a transgene product (e.g. a viral antigen or a suicide gene product) and a fusion protein as well as a composition comprising vector(s) or viral particles encoding a transgene product and a fusion protein. The transgene and the fusion-encoding nucleic acid sequences may be expressed from the same vector or from separate vectors which may have the same origin (e.g. adenoviral vectors) or a different origin (e.g. a MVA vector encoding the particular antigen and an adenoviral vector encoding the fusion protein). The fusion protein and the transgene product (or their respective encoding vectors) can be introduced into the host cell or organism either concomitantly or sequentially either via the mucosal and/or systemic route.

A preferred combination in the context of the present invention uses a composition comprising or encoding (i) a fusion protein having an amino acid sequence as shown in any of SEQ ID NO: 1-19, and (ii) an RPV antigen (particularly preferred in this context is a nononcogenic and membrane-anchored early antigen of HPV-16). For example, a host organism can be treated with a vector which expresses the fusion protein of the invention and either with a nononcogenic and membrane-anchored HPV-16 E7 variant or a vector which expresses it. Alternatively, a host organism can be treated with the fusion protein of the invention and either with a nononcogenic and membrane-anchored HPV-16 E7 variant or a vector which expresses it. Preferably, the fusion protein of the invention is encoded by an adenoviral vector and the HPV antigen by a MVA vector. In this regard, the adenoviral vector encoding the fusion protein of the invention is initially administered in the host organism and the MVA vector encoding the immunogenic HPV antigen is subsequently administered to the same host organism after a period varying from one day to two months. The fusion protein-encoding adenoviral vector is preferably administered by the mucosal route whereas the MVA vector is injected by subcutaneous route. Compositions comprising a unique vector containing the sequences encoding both the fusion protein and a nononcogenic and membrane-anchored HPV-16 E7 variant can also be envisaged in this context. Booster vaccinations with the particular antigen or a vector expressing it can also be performed from about 2 weeks to several years after the original administration.

Another preferred combination in the context of the present invention uses (i) a fusion protein having an amino acid sequence as shown in any of SEQ ID NO: 1-19 or a vector encoding it and (ii) a vector encoding the FCU-1 gene product (Cdase-UPRTase fusion which is described in WO99/54481). Preferably, the fusion protein of the invention is encoded by an adenoviral vector and the FCU-1 gene product by a MVA vector. In this regard, both vectors can be co-administered or administered sequentially in a short time period into the host organism; e.g. by intratumor injection. The prodrug 5-FC is then given to the host organism within the day or week following the administration of both vectors.

The present invention also provides a method for the treatment of a human or animal organism, comprising administering to said organism a therapeutically effective amount of the fusion protein, the vector, the infectious viral particle, the host cell or the composition of the invention. As used herein a "therapeutically effective amount" is a dose sufficient for the alleviation of one or more symptoms normally associated with the disease or condition desired to be treated. When prophylactic use is concerned, this term means a dose sufficient to prevent or to delay the establishment of a disease or condition.

The method of the present invention can be used for preventive purposes and for therapeutic applications relative to the diseases or conditions listed above. It is to be understood that the present method can be carried out by any of a variety of approaches. For this purpose, the fusion protein, the vector, the infectious viral particle, the host cell or the composition of the invention can be administered directly in vivo by any conventional and physiologically acceptable administration route, such as those recited above, using specific delivery means adapted to this administration route. It could be advantageous to proceed to the administration of the active agent following an increase of permeability of a blood vessel. Such a permeability increase may be obtained by enhancing hydrostatic pressure (i.e. by obstructing outflow and/or inflow), osmotic pressure (i.e. with hypertonic solution) and/or by using appropriate drugs (e.g. histamine; WO 98/58542).

Alternatively, one may employ eukaryotic host cells that have been engineered ex vivo to contain the active agent according to the invention. The transfected/infected cells are grown in vitro and then reintroduced into the patient. The graft of encapsulated host cells is also possible in the context of the present invention (Lynch et al, 1992, Proc. Natl. Acad. Sci. USA 89, 1138-1142). Cells infected ex-vivo can be either autologous cells or heterologous cells, e.g. heterologous cells obtained from one or a plurality of subjects with a condition similar to that which is to be treated. The cells can be of a single cell type or of a mixture of cell types, e.g. they can comprise cells of one or plural cell lines established from clinical tumour samples. The cells for administration can preferably be inactivated, e.g. by irradiation, before administration. Among the cells that can usefully be treated in this way are for example malignant cells of human or non-human organisms (see R Jurecic et al, ch 2, pp 7-30 in 'Somatic Gene Therapy' CRC Press 1995, ed. P. L. Chang).

The efficacy of the active agent or composition of the present invention to enhance the immune response in an animal or human organism can be tested in a variety of ways including, but not limited to, detection of cellular immunity within the treated organism, determining lymphocyte or dendritic cell activity, detection of immunoglobulin levels, determining the activity of antigen presenting cells, determining dendritic cell development or challenge of the treated organism with an appropriate infectious or tumor-inducing agent to determine whether the treated organism is resistant to disease. In one embodiment, therapeutic compositions can be tested in animal models such as mice. Such techniques are known to those skilled in the art.

As discussed above, the method of the present invention is particularly intended for the treatment of cancers, to provide tumor inhibition growth or tumor regression. For example, tumor inhibition may be determined by measuring the actual tumor size over a period of time. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), may be utilized to estimate tumor size. Such methods may also utilize a variety of imaging agents, including for example, conventional imaging agents (e.g., Gallium-67 citrate), as well as specialized reagents for metabolite or receptor imaging, or immunologic imaging (e.g., radiolabeled monoclonal antibody directed to specific tumor markers). In addition, non-radioactive methods such as ultrasound (see, "Ultrasonic Differential Diagnosis of Tumors", Kossoff and Fulcuda, (eds.), Igaku-Shoin, New York, 1984), may also be used to estimate the size of a tumor. Alternatively, inhibition of tumor growth may be determined based upon a change in the presence of a tumor marker. Examples include PSA for the detection of prostate cancer and CEA for the detection of colorectal and certain breast cancers. For yet other types of cancers such as leukemia, inhibition of tumor growth may be determined based upon a decreased number of leukemic cells in a representative blood cell count.

Further validation of the therapeutic efficacy of the active agent of the invention for treating cancer can be determined in a suitable animal model, e.g. using mice injected with a representative human cancer cell line. After solid tumors have developed to a sizeable diameter, the mice are injected intravenously or intratumorally with the active agent, and then monitored for reduced tumor growth rate and increased survival (see Example 4).

Prevention or treatment of a disease or a condition can be carried out using the present method alone or, if desired, in conjunction with presently or conventional therapeutic modalities (e.g. radiation, chemotherapy and/or surgery). The use of multiple therapeutic approaches provides the patient with a broader based intervention. In one embodiment, treatment with an active agent according to the invention can be preceded by surgical intervention. In another embodiment, radiotherapy (e.g. gamma radiation) is provided in combination with the active agents according to the invention. Those skilled in the art can readily formulate appropriate radiation therapy protocols and parameters which can be used in the method of the invention (see for example Perez and Brady, 1992, Principles and Practice of Radiation Oncology, 2nd Ed. JB Lippincott Co; using appropriate adaptations and modifications as will be readily apparent to those skilled in the field). Preferably, the active agent of the invention is administered before exposing the individual to a therapeutically effective amount of anti-cancer radiation. In still another embodiment, the method of the invention is associated to chemotherapy. Chemotherapy include administration of cytotoxic and/or cytostatic agents which can be provided in a single dose or, alternatively, in multiple doses that are administered over several hours, days and/or weeks. Chemotherapeutics are delivered according to standard protocols using standard agents, dosages and regimens and their administration may proceed, be concommitant, or subsequent to the administration of the active agent of the invention. Suitable chemotherapeutics include without limitation cisplatin, carboplatin, doxirubicin, bleomycin, vinblastine, danurubicin, tamoxiphen, taxol, 5-FU and methotrexate. In some embodiments, chemotherapy and radiation treatments are both employed before or following the administration of the active agent of the invention.

When the method of the invention uses a vector, infectious particle, host cell or composition engineered to express a transgene encoding a suicide gene product, it can be advantageous to additionally administer a pharmaceutically acceptable quantity of a prodrug which is specific for the expressed suicide gene product. The two administrations can be made simultaneously or consecutively, but preferably the prodrug is administered after the active agent of the invention. By way of illustration, it is possible to use a dose of prodrug from 50 to 500 mg/kg/day, a dose of 200 mg/kg/day being preferred. The prodrug is administered in accordance with standard practice. The oral route is preferred. It is possible to administer a single dose of prodrug or doses which are repeated for a time sufficiently long to enable the toxic metabolite to be produced within the host organism or cell. As mentioned above, the prodrug ganciclovir or acyclovir can be used in combination with the TK. HSV-1 gene product and 5-FC in combination with the cytosine deaminase and/or uracil phosphotransferase gene product.

The present invention also relates to a method for enhancing an immune response in an animal or human organism comprising introducing into said organism the fusion protein, the vector, the infectious particles, the host cells or the composition of the invention, so as to enhance said immune response. The immune response can be a specific and/or a nonspecific, humoral and/or cell-mediated response. Specifically, the immune response is a T cell response, and more specifically a cytotoxic T cell response. Preferably, the method of the invention allows to enhance the number and/or the cytolytic activity of CTLs specific for a selected antigen. Introduction is preferably made subcutaneously, intradermally, intramuscularly, intranasally, intratumorally or in close proximity of a tumor. In one preferred embodiment, the method of the invention is directed to enhancing an antigen-specific immune response in a host cell or organism, by using an active agent comprising, or expressing a transgene product consisting of one or more specific antigens against which a specific immune response is desired (e.g. an HPV-16 E6 or E7 variant). In another embodiment, the method of the invention is directed to enhancing an antigen-specific immune response in a host cell or organism, by using an active agent comprising or expressing a transgene consisting of one or more tumor-associated or tumor-specific antigens present on a tumor, in order to inhibit growth or to prevent re-growth of any tumors bearing said antigen.

The present invention also provides the use of the fusion protein, the vector, the infectious particles, the host cells or the composition of the invention, for the preparation of a drug intended for the purpose of activating maturation of dendritic cells in an animal or human organism, and thus enhancing a nonspecific immune response against tumor or viral antigens. In a preferred embodiment, this use is intended to the prevention or treatment of a disease that can be reversed by the activation of maturation of dendritic cells. An enhancement of the maturation of dendritic cells can be evaluated as illustrated in Example 2. In one preferred embodiment, the fusion protein for this use is IL-2/IL-18 (with a special preference for the illustrated IL-2/proIL-18 and IL-2/proIL-18(K89A) fusions) or IL-7/IL-2.

The present invention also provides the use of the fusion protein, the vector, the infectious particles, the host cells or the composition of the invention, for the preparation of a drug intended for the purpose of activating NKT cells in an animal or human organism, and thus enhancing a nonspecific immune response against tumor or viral antigens. In a preferred embodiment, this use is intended to the prevention or treatment of a disease such as cancer and infectious disease that can be reversed by the activation NKT cells. An enhancement of the activation of NKT cells can be evaluated as illustrated in Example 2. In one preferred embodiment, the fusion protein for this use is IL-2/IL-18 (with a special preference for the illustrated IL-2/proIL-18 and IL-2/proIL-18 (K89A) fusions).

The present invention also provides the use of the fusion protein, the vector, the infectious particles, the host cells or the composition of the invention, for the preparation of a drug providing lower cytotoxicity upon administration in an animal or human organism as compared to the cytotoxicity observed upon administration of the individual X and/or Y entities. A limited cytotoxicity is especially advantageous for treating cancers and infectious diseases such as those cited above. It can be evaluated by measuring AICD activity or VLS (Vascular Leak Syndrome) as illustrated in Example 3. In one preferred embodiment, the fusion protein for this use is IL-2/IL-18 (with a special preference for the illustrated IL-2/proIL-18 and IL-2/proIL-18(K89A) fusions) or IL-7/IL-2.

The invention also provides antibodies that selectively bind to the fusion protein of the present invention or peptide fragments thereof. As used herein, an antibody selectively binds a target peptide when it binds the target peptide and does not significantly bind to unrelated proteins. In certain cases, it would be understood that antibody binding to the peptide is still selective despite some degree of cross-reactivity.

As used herein, an antibody is defined in terms consistent with that recognized within the art. The antibodies of the present invention include polyclonal antibodies and monoclonal antibodies, as well as fragments of such antibodies, including, but not limited to, Fab or F(ab').sub.2, and Fv fragments.

Many methods are known for generating and/or identifying antibodies to a given target polypeptide/peptide. Several such methods are described by Harlow (1989, Antibodies, Cold Spring Harbor Press). A preferred method to produce antibodies of the present invention includes (a) administering to an animal an effective amount of a fusion protein of the present invention and/or a peptide fragment thereof, to produce the antibodies and (b) recovering the antibodies. In another method, antibodies of the present invention are produced recombinantly using conventional techniques in the art. The full-length fusion protein or an antigenic peptide fragment can be used. Antibodies are preferably prepared from regions or discrete fragments of the secreted proteins. Particularly important regions and fragments are those comprising unique sequences of the fusion proteins of the invention, such as the ones overlapping the fusion site between X and Y entities. An antigenic fragment will typically comprise at least 8 contiguous amino acid residues. The antigenic fragment can comprise, however, at least 10, 12, 14, 16 or more amino acid residues.

Antibodies of the present invention have a variety of potential uses that are within the scope of the present invention. For example, such antibodies can be used (a) as reagents in assays to detect a fusion protein of the present invention, (b) as reagents in assays to modulate cellular activity through a fusion protein of the present invention, and/or (c) as tools to recover a fusion protein of the present invention from a mixture of proteins and other contaminants. The use of an antibody of the present invention as reagent can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. Examples of bioluminescent materials include luciferase, luciferin, and aequorin. Examples of suitable radioactive material include $^{125}I$, $^{131}I$, $^{35}S$ or $^{3}H$.

The antibodies can be used to isolate one of the fusion proteins of the present invention by standard techniques, such as affinity chromatography or immunoprecipitation. The antibodies can facilitate the purification of the recombinantly produced fusion protein from cultured cells. Also, such antibodies can be used to detect protein in situ, in vitro, or in a cell lysate or supernatant in order to evaluate the abundance and pattern of expression. Further, such antibodies are useful to detect the presence or to assess the expression of one of the fusion proteins of the present invention in cells, biological samples or tissues of an individual over the course of a treatment. Additionally, such antibodies can be used to identify individuals that require modified treatment modalities. These uses can also be applied in a therapeutic context in which treatment involves inhibiting the function of the fusion protein of the invention.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF FIGURES

FIG. 1 illustrates the schematic construction steps for generating an adenoviral vector encoding a fusion protein.

FIG. 2 illustrates the in vitro evaluation of the functionality of IL-2-containing fusion proteins by measurement of T cell costimulation. "Spleno" represents splenocytes, "ConA" represents splenocytes activated with Concanavalin A, "Anti-CD3" represents splenocytes activated with a murine CD3-specific antibody, and "½" and "1/10" represent the dilutions of the viral supernatants used in this assay. "Empty Ad" represents a negative control devoid of fusion-encoding sequences.

FIG. 3 illustrates the in vitro evaluation of the functionality of IL-7 containing fusion proteins by measurement of the proliferation of pro-B-2E8 lymphoblast cells. "rMu IL-7" represents recombinant murine IL-7 (1 to 500 ng/ml), "p" represents pure viral supernatants and "½" and "1/10" represent the dilutions of the viral supernatants used in this assay.

FIG. 4 illustrates the in vitro evaluation of the functionality of IL-18 containing fusion proteins by measurement of the induction of IFN-g secretion by ConA pre-activated murine splenocytes (Concanavaline A 10 µg/ml; 24 h). The production of IFN-g is evaluated by ELISA immunoassays. "1/20" and "1/50" represent the dilutions of the viral supernatants used in this assay. IL-18 here represents proIL-18.

FIG. 5 illustrates the in vitro activation of splenocytes. Analysis of IFNg secretion induce on ConA-primed (10 µg/ml) or unprimed splenocytes by A549 supernatants containing 20 ng/ml of mproIL-18(K89A), the combination of mIL-2+mproIL-18(K89A), mIL-2/matureIL-18 (Ad-mIL-2/IL-18), mIL-2/matureIL-18(K89A) (Ad-mIL-2/IL-18*), mIL-2/proIL-18 and mIL-2/proIL-18(K89A). As negative control, supernatant of control virus-infected A549 cells were used. These results are representative of three different experiments with similar results. IL-18* represents IL-18 (K89A).

Figure 9:
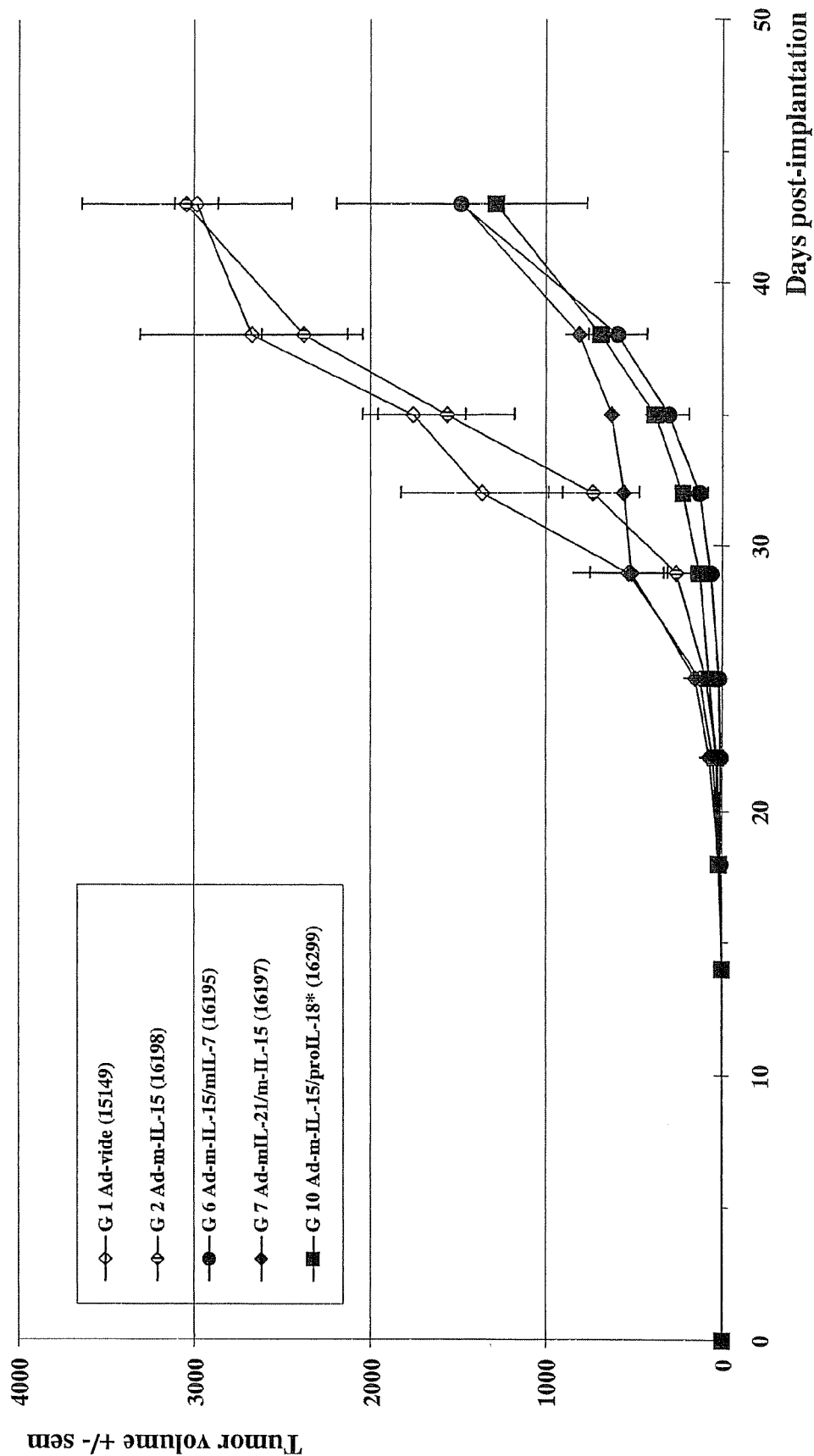

FIG. 9 illustrates the antitumor activity following three intratumoral injections of Ad expressing IL-15-containing fusions in mice hearing B16F10 tumors. G1 represents treatment with an Ad vector expressing no transgene (Ad empty), G2 represents treatment with an Ad vector expressing the mature murine IL-15 cytokine equipped at its N-terminus with the IL-2 signal peptide (Ad-mIL-15), G6 represents treatment with an Ad vector expressing the fusion between the mature murine IL-15 cytokine equipped at its N-terminus with the IL-2 signal peptide and the murine IL-7 (Ad-mIL-15/mL-7). G7 represents treatment with an Ad vector expressing the fusion between the murine IL-21 cytokine and the mature murine IL-15 (Ad-mIL-21/mL-15). G10 represents treatment with an Ad vector expressing the fusion between the mature murine IL-15 cytokine equipped at its N-terminus with the IL-2 signal peptide and the murine proIL-18 variant K89A (Ad-mIL-15/proIL-18*).

Figure 10:
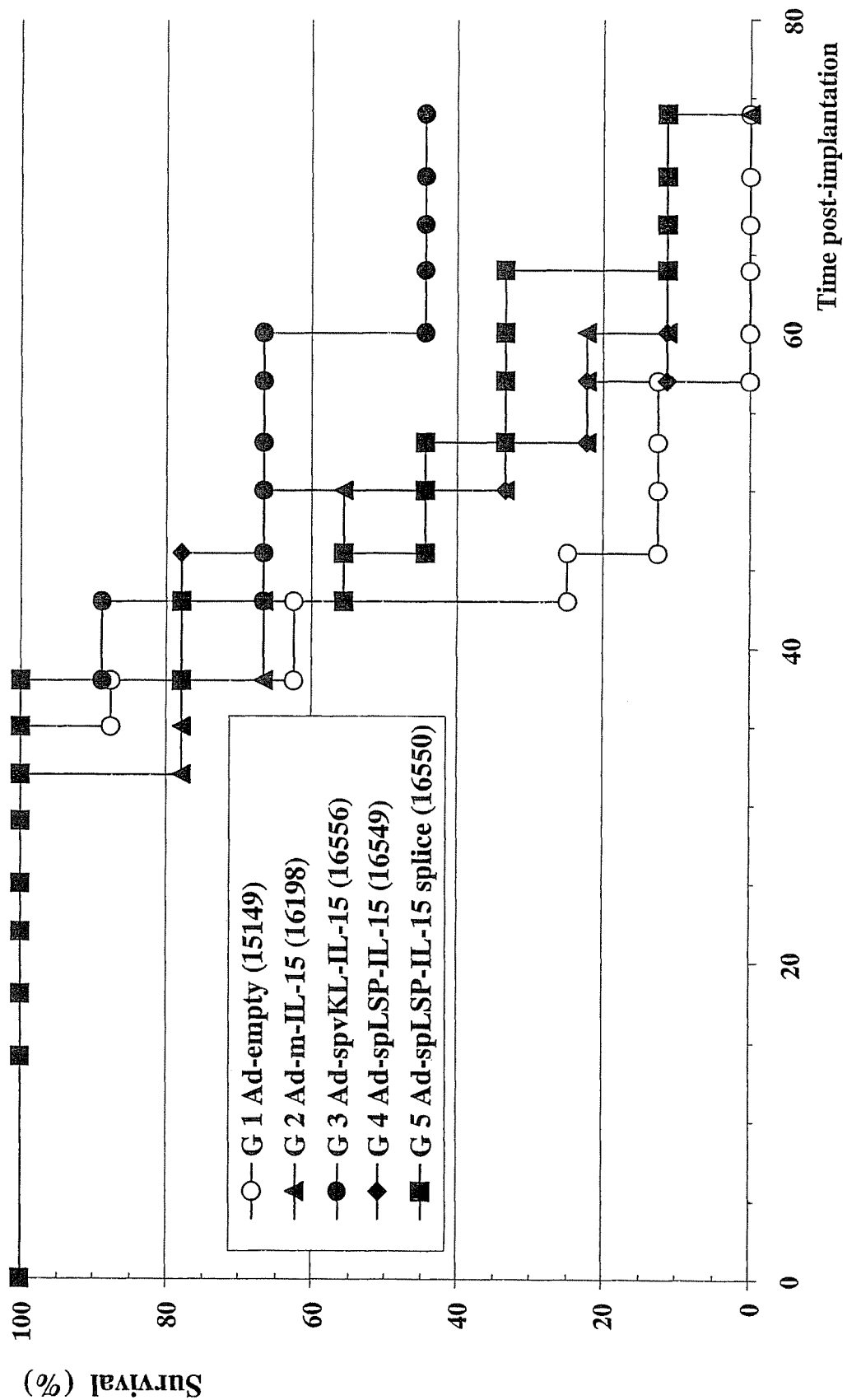

FIG. 10 represents the intratumoral injection of adenovirus encoding new improved IL-15-versions in mice bearing B16F10 tumors. G1 represents treatment with an Ad vector expressing no transgene (Ad vide), G2 represents treatment with an Ad vector expressing the mature murine IL-15 cytokine equipped at its N-terminus with the IL-2 signal peptide (Ad-mIL-15 or Ad-spi12-IL-15). G3 represents treatment with an Ad vector expressing the mature murine IL-15 cytokine equipped at its N-terminus with the IgG kappa light chain signal peptide (Ad-spvKL-IL-15). G4 represents treatment with an Ad vector expressing the mature murine IL-15 cytokine equipped with the endogenous long form signal peptide (Ad-spLSP-IL-15). G5 represents treatment with an Ad vector expressing the mature murine IL-15 cytokine equipped with the endogenous short fowl signal peptide and splice (Ad-spLSP-IL-15 splice).

The following examples serve to illustrate the present invention.

EXAMPLES

The constructs described below are prepared according to the general techniques of genetic engineering and of molecular cloning, as detailed in Sambrook et al. (2001, Molecular Cloning; A Laboratory Manual, Cold Spring Harbor Laboratory Press, Cold Spring Harbor N.Y.) or according to the manufacturer's recommendations when a commercial kit is used. The cloning steps using bacterial plasmids are preferably carried out in the *E. coli* strain 5K (Hubacek and Glover, 1970, J. Mol. Biol. 50, 111-127) or in *E. coli* strain BJ5183 (Hanahan, 1983, J. Mol. Biol. 166, 557-580). The latter strain is preferably used for homologous recombination steps. The NM522 strain (Stratagene) is suitable for propagating the M13 phage vectors. The PCR amplification techniques are known to those skilled in the art (see for example PCR. Protocols—A guide to methods and applications, 1990; Ed Innis, Gelfand, Sninsky and White, Academic Press Inc). With respect to the repair of restriction sites, the technique used consists in filling the overhanging 5' ends using the large fragment of *E. coli* DNA polymerase I (Klenow). The Ad5 nucleotide sequences are those disclosed in the Genebank database, under the reference M73260 or AY339865.

Materials and Methods

Cloning and Construction of Multifunctional Cytokine cDNAs.

Splenocytes from C57B16 mice were harvested and stimulated during 3 days with a mixture of concanavalin A (10 µg/ml, SIGMA) and murine IL-2 (10 IU/ml, R&D Systems) or LPS (10 µg/ml, SIGMA) and murine GM-CSF (50 IU/ml, R&D Systems). mRNA from activated splenocytes were then extracted using RNA Now (Ozyme). Murine IFN-g, IL-2, IL-7, IL-15, IL-18 and IL-21 cDNAs were amplified by RT-PCR (Platinum Quantitative RT-PCR, Thermoscript™ one step system, Invitrogen) using specific oligonucleotides based on the sequence data available in specialized data banks. The mutated fowls of murine IL-2 (D20I, N88R, N88G and Q126M) and the mutated form of murine IL-18 (K89A) were made using QuikChange® Site-Directed Mutagenesis Kit (Stratagene, La Jolla, Calif., USA). Two forms of murine IL-18 cDNA have been used for the fusion molecules, one encoding the precursor pro-IL-18 and one encoding the mature murine IL-18 (devoid of the prosequence). The murine secretable IL-15 is described in Fehniger et al. (2001, J. Exp. Med. 193, 219-231) and Suzuki et al. (2001, J. Leuk. Biol. 69, 531-537) The following oligonucleotides were used to clone and mutate the cytokine sequences:

```
Murine IL-2
                                       (SEQ ID NO: 20)
5': otg14157
cggaattccacagtgacctcaagtcc (SEQ ID NO: 21)
3': otg14158
ggggtacccttatgtgttgtaag Murine IL-2 (N88G)
                                       (SEQ ID NO: 22)
5': otg15485
gagaatttcatcagcggtatcagagtaactgttg (SEQ ID NO: 23)
3': otg15486
caacagttactctgataccgctgatgaaattctc Murine IL-2 (N88R)
                                       (SEQ ID NO: 24)
5': otg15487
gagaatttcatcagccgtatcagagtaactgttg (SEQ ID NO: 25)
3': otg15488
caacagttactctgatacggctgatgaaattctc Murine IL-2 (Q126M)
                                       (SEQ ID NO: 26)
5': otg15489
ggagatggatagccttctgtatgagcatcatctcaacaagccc (SEQ ID NO: 27)
3': otg 15490
gggcttgttgagatgatgctcatacagaaggctatccatctcc Murine IL-2 (D20I)
                                       (SEQ ID NO: 28)
5': otg15536
gagcagctgttgatgatcctacaggag (SEQ ID NO: 29)
3': otg15537
ctcctgtaggatcatcaacagctgctc Murine IL-7
                                       (SEQ ID NO: 30)
5': otg14438
ccgctcgagcggatgttccatgtttcttttagata (SEQ ID NO: 31)
3': otg14439
cggggtacccgttatatactgcccttcaaaat Murine IL-18
                                       (SEQ ID NO: 32)
5': otg14440
ccgctcgagcggatggctgccatgtcagaaga
```

-continued

3': otg14441 (SEQ ID NO: 33)
cggggtaccccgctaactttgatgtaagttagtgagagtgaac

Murine IL-18 (K89A)

5': otg14457 (SEQ ID NO: 34)
ccagactgataatatacatgtacgcagacagtgaagtaagagg

3': otg14458 (SEQ ID NO: 35)
cctcttacttcactgtctgcgtacatgtatattatcagtctgg

Murine mature IL-18 (without pro-sequence)

5': otg14657 (SEQ ID NO: 36)
ggtggaggcggttcaggcggaggtggctctaactttggccgacttcactg

3': otg14656 (SEQ ID NO: 37)
ctaactttgatgtaagttagtgagagtgaac

Murine IL-21

5': otg14436 (SEQ ID NO: 38)
ccgctcgagcggatggagaggaccccttgtctg

3': otg14437 (SEQ ID NO: 39)
cggggtaccccgctaggagagatgctgatgaatcatc

Murine IL-15

5': otg15138 (SEQ ID NO: 40)
ccgctcgagcggatgtacagcatgcagctcgc

3': otg15139 (SEQ ID NO: 41)
cggggtaccccgctacttgtcatcgtcgtcc

Figure 1:
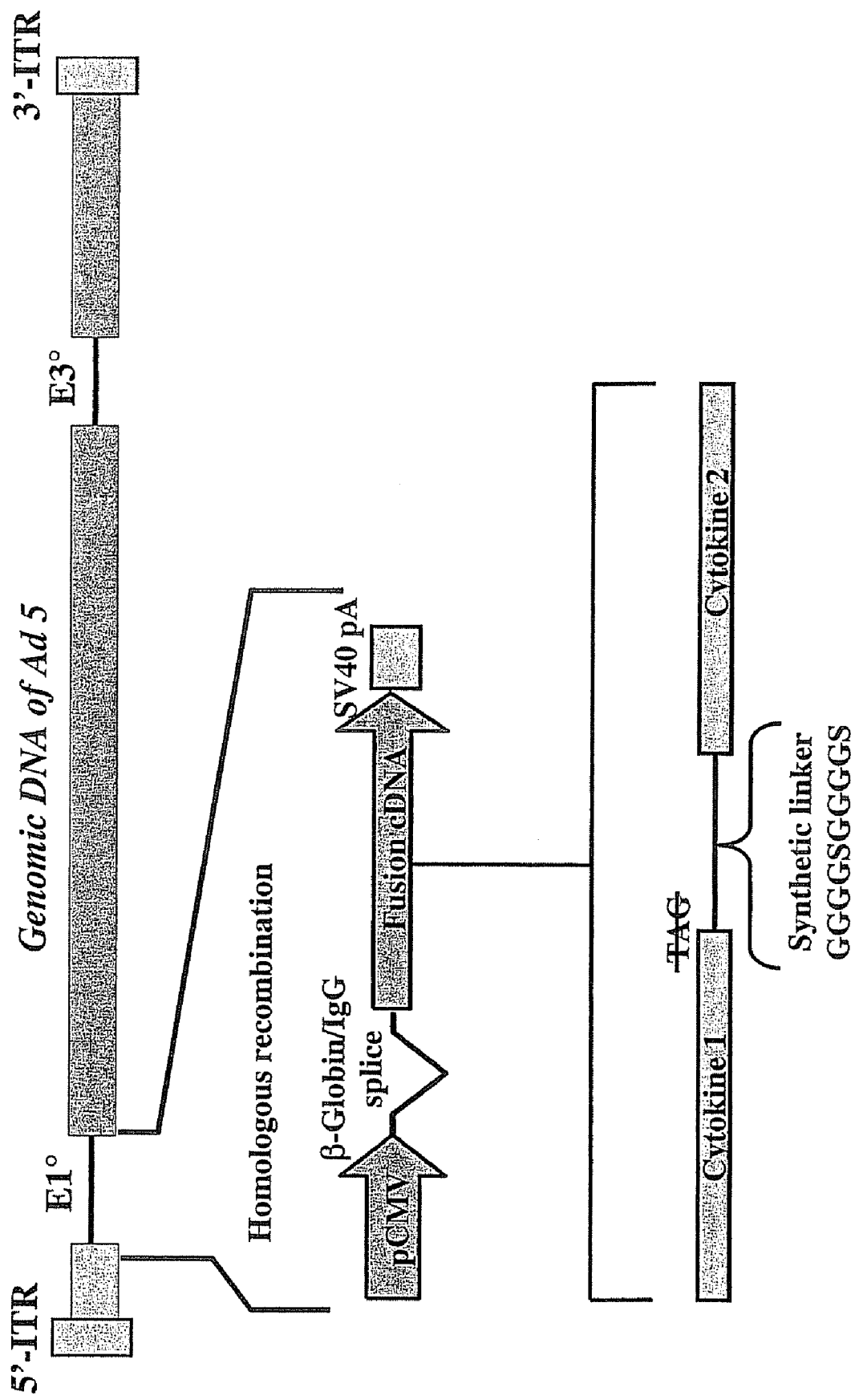

As described in FIG. 1, once amplified by RT-PCR, the sequences encoding the two cytokine moieties (X and Y) were cloned in frame by PCR techniques with a flexible linker $(G_4S)^2$ or $(G_4S)^3$ present between them (Gillies et al., 2002, Cancer Immunol. Immunother. 51, 449-460), using the following oligonucleotides:

*Murine IL-2/L/IL-18

5': otg14442 (SEQ ID NO: 42)
ccgctcgagcggatgtacagcatgcagctcga

5'L: otg14444 (SEQ ID NO: 43)
ggtggaggcggttcaggcggaggtggctctatggctgccatgtcagaaga 3'L: otg14443 (SEQ ID NO: 44)
agagccacctccgcctgaaccgcctccaccttgagggcttgttgagatga 3': otg14441 (SEQ ID NO: 33)
cggggtaccccgctaactttgatgtaagttagtgagagtgaac Murine IL-18/L/IL-2

5': otg14440 (SEQ ID NO: 32)
ccgctcgagcggatggctgccatgtcagaaga

5'L: otg14446 (SEQ ID NO: 45)
ggtggaggcggttcaggcggaggtggctctatgtacagcatgcagctcg

3'L: otg14445 (SEQ ID NO: 46)
agagccacctccgcctgaaccgcctccaccactttgatgtaagttagtgagtgaacat 3': otg14447 (SEQ ID NO: 47)
cggggtaccccgttattgagggcttgttgag Murine IL-2/L/mature IL-18 (native or K89A)

5': otg15657 (SEQ ID NO: 48)
ggtggaggcggttcaggcggaggtggctctaactttggccgacttcactg

3': otg15656 (SEQ ID NO: 49)
ctaactttgatgtaagttagtgagagtgaac

*Murine IL-2/L/IL-7

5': otg14442 (SEQ ID NO: 42)
ccgctcgagcggatgtacagcatgcagctcga

5'L: otg14449 (SEQ ID NO: 50)
ggtggaggcggttcaggcggaggtggctctatgttccatgtttcttttag 3'L: otg14443 (SEQ ID NO: 44)
agagccacctccgcctgaaccgcctccaccttgagggcttgttgagatga 3': otg14439 (SEQ ID NO: 31)
cggggtaccccgttatatactgcccttcaaaat Murine IL-7/L/IL-2

5': otg14438 (SEQ ID NO: 30)
ccgctcgagcggatgttccatgtttcttttagata

5'L: otg14446 (SEQ ID NO: 45)
ggtggaggcggttcaggcggaggtggctctatgtacagcatgcagctcg

3'L: otg14450 (SEQ ID NO: 51)
agagccacctccgcctgaaccgcctccacctatactgcccttcaaaatt

3': otg14447 (SEQ ID NO: 47)
cggggtaccccgttattgagggcttgttgag

*Murine IL-2/L/IL-21

5': otg14442 (SEQ ID NO: 42)
ccgctcgagcggatgtacagcatgcagctcga

5'L: otg14448 (SEQ ID NO: 52)
ggtggaggcggttcaggcggaggtggctctatggagaggaccccttgtctg 3'L: otg14443 (SEQ ID NO: 44)
agagccacctccgcctgaaccgcctccaccttgagggcttgttgagatga 3': otg14437 (SEQ ID NO: 39)
cggggtaccccgctaggagagatgctgatgaatcatc Murine IL-21/L/IL-2

5': otg14436 (SEQ ID NO: 38)
ccgctcgagcggatggagaggaccccttgtctg

5'L: otg14446 (SEQ ID NO: 45)
ggtggaggcggttcaggcggaggtggctctatgtacagcatgcagctcg

3'L: otg14451 (SEQ ID NO: 53)
agagccacctccgcctgaaccgcctccaccggagagatgctgatgaatcatc -continued

*Murine IL-2/L/IFN-g (SEQ ID NO: 42)
5': otg14442
ccgctcgagcggatgtacagcatgcagctcga (SEQ ID NO: 54)
5'L: otg14636
ggtggaggcggttcaggcggaggtggctctatgaacgctacacactgcatcttgg (SEQ ID NO: 44)
3'L: otg14443
agagccacctccgcctgaaccgcctccaccttgagggcttgttgagatga (SEQ ID NO: 55)
3': otg14637
cggggtaccccgtcagcagcgactccttttccg Murine IFN-g/L/IL-2

(SEQ ID NO: 56)
5': otg14639
ccgctcgagcggatgaacgctacacactgcatcttgg (SEQ ID NO: 45)
5'L: otg14446
ggtggaggcggttcaggcggaggtggctctatgtacagcatgcagctcg (SEQ ID NO: 57)
3'L: otg14641
agagccacctccgcctgaaccgcctccaccgcagcgactccttttccgc (SEQ ID NO: 47)
3': otg14447
cggggtaccccgttattgagggcttgttgag

*Murine IL-2/L/IL-15

(SEQ ID NO: 42)
5': otg14442
ccgctcgagcggatgtacagcatgcagctcga (SEQ ID NO: 58)
5'L: otg15140
ggtggaggcggttcaggcggaggtggctctatgtacagcatgcagctcgc (SEQ ID NO: 44)
3'L: otg14443
agagccacctccgcctgaaccgcctccaccttgagggcttgttgagatga (SEQ ID NO: 41)
3': otg15139
cggggtaccccgctacttgtcatcgtcgtcc Murine IL-15/L/IL-2

(SEQ ID NO: 40)
5': otg15138
ccgctcgagcggatgtacagcatgcagctcgc (SEQ ID NO: 45)
5'L: otg14446
ggtggaggcggttcaggcggaggtggctctatgtacagcatgcagctcg (SEQ ID NO: 59)
3'L: otg15141
agagccacctccgcctgaaccgcctccacccttgtcatcgtcgtccttg (SEQ ID NO: 47)
3': otg14447
cggggtaccccgttattgagggcttgttgag

*Murine IL-7/L/IL-15

(SEQ ID NO: 30)
5': otg14438
ccgctcgagcggatgttccatgtttcttttagata (SEQ ID NO: 58)
5'L: otg15140
ggtggaggcggttcaggcggaggtggctctatgtacagcatgcagctcgc (SEQ ID NO: 51)
3'L: otg14450
agagccacctccgcctgaaccgcctccacctatactgcccttcaaaatt (SEQ ID NO: 41)
3': otg15139
cggggtaccccgctacttgtcatcgtcgtcc Murine IL-15/IL-7

(SEQ ID NO: 40)
5': otg15138
ccgctcgagcggatgtacagcatgcagctcgc (SEQ ID NO: 50)
5'L: otg14449
ggtggaggcggttcaggcggaggtggctctatgttccatgtttcttttag (SEQ ID NO: 59)
3'L: otg15141
agagccacctccgcctgaaccgcctccacccttgtcatcgtcgtccttg (SEQ ID NO: 31)
3': otg14439
cggggtaccccgttatatactgcccttcaaaaat

*Murine IL-21/L/IL-15

(SEQ ID NO: 38)
5': otg14436
ccgctcgagcggatggagaggacccttgtctg (SEQ ID NO: 58)
5'L: otg15140
ggtggaggcggttcaggcggaggtggctctatgtacagcatgcagctcgc (SEQ ID NO: 53)
3'L: otg14451
agagccacctccgcctgaaccgcctccaccggagagatgctgatgaatcatc (SEQ ID NO: 41)
3': otg15139
cggggtaccccgctacttgtcatcgtcgtcc Murine IL-15/L/IL-21

(SEQ ID NO: 40)
5': otg15138
ccgctcgagcggatgtacagcatgcagctcgc (SEQ ID NO: 52)
5'L: otg14448
ggtggaggcggttcaggcggaggtggctctatggagaggacccttgtctg (SEQ ID NO: 59)
3'L: otg15141
agagccacctccgcctgaaccgcctccacccttgtcatcgtcgtccttg (SEQ ID NO: 39)
3': otg14437
cggggtaccccgctaggagagatgctgatgaatcatc

*Murine IL-15/L/IL-18 (native or K89A)

(SEQ ID NO: 40)
5': otg15138
ccgctcgagcggatgtacagcatgcagctcgc (SEQ ID NO: 43)
5'L: otg14444
ggtggaggcggttcaggcggaggtggctctatggctgccatgtcagaaga (SEQ ID NO: 59)
3'L: otg15141
agagccacctccgcctgaaccgcctccacccttgtcatcgtcgtccttg -continued (SEQ ID NO: 33)
3': otg14441
cggggtaccccgctaactttgatgtaagttagtgagagtgaac Murine IL-18 (native or K89A)/L/IL-15
(SEQ ID NO: 32)
5': otg14440
ccgctcgagcggatggctgccatgtcagaaga (SEQ ID NO: 58)
5'L: otg15140
ggtggaggcggttcaggcggaggtggctctatgtacagcatgcagctcgc (SEQ ID NO: 46)
3'L: otg14445
agagccacctccgcctgaaccgcctccaccactttgatgtaagttagtga gagtgaacat (SEQ ID NO: 41)
3': otg15139
cggggtaccccgctacttgtcatcgtcgtcc In each case, both types of fusion proteins (X-Y and Y-X) were constructed and assayed for biological and therapeutic activities. Each cytokine was also cloned individually in the same adenoviral backbone to serve as control.

Adenovirus Production and Titration

The sequence encoding each fusion protein was inserted in an adenoviral shuttle plasmid containing a CMV-driven expression cassette surrounded by adenoviral sequences (adenoviral nucleotides 1-458 and nucleotides 3328-5788, respectively) to allow generation of the vector genome by homologous recombination (Chartier et al., 1996, J. Virol. 70, 4805-4810). In the resulting adenoviral vectors, E3 (nucleotides 28592-30470) and Eli (nucleotides 459-3327) are deleted, and the E1 region is replaced by the expression cassette containing, from 5' to 3', the CMV immediate-early enhancer/promoter, a chimeric human beta-globin/IgG intron, the sequence encoding the fusion protein and the SV40 late polyadenylation signal. The recombinant adenoviruses were generated by transfecting the PacI linearized viral genomes into the PER C6 complementation cell line (Fallaux et al., 1998, Human Gene Therapy 9, 1909-1917). Virus propagation, purification and titration were made as described previously (Erbs et al., 2000, Cancer Res 60, 3813-3822).

Cell Culture

In the examples which follow, use is made of the human pulmonary carcinoma cell line A549 (ATCC; CCL-185), the 2E8 murine lymphoblast (ATCC; TIB-239) and the murine 2B4.11 T cell hybridoma (Delgado et al., 2001, J. Immunol. 166, 1028-1040). The culturing conditions are conventional in the art. For illustrative purposes, the cells are grown at 37° C. in DMEM (Gibco) supplemented with 10% Fetal Calf Serum and antibiotics. Cells are transfected according to standard techniques known to those skilled in the art.

P815 murine mastocytoma (DBA/2; FcR+, H2D$^d$, MHCI+, ICAM1+, CD48+), and B16F10 (C57B1/6; H2D$^b$, MHCI−, MHCII−, ICAM1−, CD48−) are murine melanoma cancer cell lines obtained from the American Type Culture Collection (ATCC, TIB-64 and ATCC, CRL-6475 respectively). RenCa murine renal carcinoma (BALB-C; H2D$^d$, MHCI+, MHCII+, Fas+) and TC1 murine tumor cell line are described in Dybal et al. (1992, J. Urol. 148, 1331-1337) and Lin et al. (1996, Cancer Res. 56, 21-26), respectively. All cell lines were tested negative for mycoplasma using Hoechst dye, cell culture and PCR.

Antibodies and Cytokines

Biotin-labelled anti-murine IL-2 and anti-murine IFN-g were purchased from R&D Systems (UK). Biotin-labelled anti-murine IL-18 and anti-murine IL-7 were purchased from Peprotech Inc. (USA). Purified rabbit polyclonal anti-mouse IL-15 was purchased from eBioscience (USA). Purified goat anti-murine IL-21 was purchased from R&D Systems (UK). Biotin labelled anti-goat IgG or anti-rabbit IgG were purchased from Amersham Life Sciences (USA).

PerCP-CY5.5, FITC or Phycoerythrine-labeled rat anti-mouse CD4, CD8, CD3, CD25, CD31, CD69, MAC1, CD11c, H-2K$^b$/D$^b$, Ia$^b$, NK-1.1, NK-T/NK cell antigen or unconjugated rat anti-mouse CD4 and CD8 were used as defined by the manufacturer (Pharmingen; San Diego, Calif.; USA). Unconjugated rabbit anti-human CD3 (which cross reacts with mouse CD3) or rabbit anti-rat IgG and peroxidase-labeled goat anti-rabbit were used at concentrations suggested by DAKO (Germany).

Measurement of T cell apoptosis (AICD) was made using the Annexin V-FITC apoptosis detection kit (Pharmingen, San Diego, Calif., USA).

Recombinant murine IFN-g, IL-2, IL-7, IL-21 were purchased from R&D Systems (UK). Recombinant murine IL-15 and IL-18 were purchased from Peprotech Inc. (USA). Concanavalin A was used at 1 µg/ml and purchased from SIGMA.

Analysis of Multifunctional Cytokine Expression

RenCa or A549 cells were infected in suspension with adenoviral vectors as previously described at MOI (multiplicity of infection) of 50 (30 min incubation of cells with virus dilutions in 100 µl of PBS supplemented with 2% FCS, 1% cations) (Erbs et al., 2000, Cancer Res. 60, 3813-3822). Cells were then cultured in complete medium containing 5% FCS for 48 h. RNAs from infected A549 cells were analyzed by Northern Blot using $^{32}$P-labelled mouse cytokine DNA specific probes.

Expression of individual cytokines constituting each of the fusion protein was analyzed by Western blot according to the ECL™ Western blotting protocol provided by Amersham Life Sciences (UK). A549 cells were infected at an MOI of 50. Seventy-two hours after infection, supernatants were collected and the cells were washed once with PBS and disrupted in sample buffer (Novex, Invitrogen, France) by sonication. Supernatants and cell extracts were collected and then analyzed by Western Blot on 4-12% Nupage gel (Novex, Invitrogen, France) using specific anti-mouse cytokines and the ECL detection system (Amersham Life Sciences).

In Vitro Biological Activity of Multifunctional Cytokines

T or B cell proliferation assay. Mouse spleen cell or 2E8 lymphoblast cell proliferation was assessed by the uptake of [$^3$H]thymidine as previously described (Gillis et al., 1978, J. Immunol. 120, 2027-2032; Ishihara et al., 1991, Dev. Immunol. 1, 149-161). For T cell proliferation, splenocytes were pre-activated by low doses (20 ng/ml) of murine CD3 specific antibody (145-2C11, Pharmingen, San Diego, USA) as previously described (Ting et al., 1988, J. 1 mmol. 141, 741-748). CD3-activated splenocytes were mixed with the fusion cytokines to be tested as contained in infected A549 supernatants. As positive control, spleen or 2E8 cells (5×10$^4$ cells/well) were stimulated in complete medium with either ConA (10 µg/ml), 100 ng/ml recombinant murine IL-2 or various concentrations of murine IL-7 (R&D Systems, UK). After 96 hours, the cells were pulsed with 1 µCi/well [$^3$H]thymidine. Incorporation of [$^3$H]thymidine into the DNA of proliferating T cells was measured by harvesting cellular DNA onto glass filter paper (PHD harvester, Cambridge Technology, USA) after 4 hours and by counting the radioactivity in a liquid scintillation counter (Beckman, Germany). All measurements were made in triplicate.

IFN-g secretion assay. The relative bioactivity of murine IL-18 was determined by the ability of Ad-fusion supernatants (obtained from infected cells) to augment IFN-g production in vitro (Okamura et al., 1995, Nature, 378, 88-91; Oshikawa et al., 1999, Proc. Natl. Acad. Sci. USA, 96, 13351-13356). In brief, mouse splenocytes were cocultured with Con A (1.25 µg/ml) in 24-well plated for 48 hr. Ad-fusion supernatants were added to cell suspensions of Con A-primed splenocytes in 96-well plates for 24 hr. The supernatants were collected and assayed by ELISA to detect IFN-g production (Quantikine-R&D Systems, Minneapolis, Minn.)

CTL and NK/NKT cell cytotoxicity assays. Activities of fusion cytokines were also assayed for CTL and NK cytotoxicity as previously described (Paul et al., 2000, Cancer Gene Ther. 7, 615-623). Mouse splenocytes were cocultured with Ad-fusion supernatants obtained from A549 infected cells during 7 days. The cytotoxic activities of primed splenocytes were measured on P815-CTL target or YAC-NK target as previously described (Shortman et al., 1986, J. Immunol., 137, 798-804) using EuDTPA cytotoxicity assay (Wallac Lab., Turku, Finland) (Blomberg et al., 1993, J. Immunol. Methods, 160, 27-34).

Immunostimulation in vitro. In order to analyse the in vitro effect of multifunctional fusion cytokines, bone marrow derived dendritic cells or splenocytes were incubated with Ad-fusion supernatants for 3 to 7 days. Phenotypic markers of maturation and/or activation of dendritic cell, others APCS, B, T (CD4 and CD8), NK, and NKT cells were analyzed using mouse-specific antibodies by flow cytometry analysis (FACScan, Becton Dickinson, USA).

ELISA Assay

Fusion cytokine concentrations were estimated by ELISA immunoassay. Briefly, dilution of the fusion containing supernatants were coated on a maxisorp 96 well plate (NUNC) overnight at 4° C. Fusion cytokines were then revealed with purified polyclonal rabbit anti-mouse IL-2 or IL-18 (Biovision CA). Rabbit IgG were then revealed with a specific monoclonal anti-rabbit IgG conjugated with HRPO (Jackson Laboratories). Wells coated with serial dilutions of recombinant murine IL-2 or murine IL-18, in tissue culture medium, were used as positive control (R&D Systems, Minneapolis, Minn.) to generate standard curves for the estimations of fusokine concentrations.

AICD (Activation Induced Cell Death) Assay

AICD, in which signals normally associated with lymphocyte stimulation instead result in the demise of the cell, has been proposed as a mechanism of the deletion of antigen-specific lymphocytes. T cells can be sensitive or resistant to AICD, and IL-2 can regulate the susceptibility of T cells to AICD (Brunner et al., 1996, Int. Immunol., 8, 1017-1026; Nguyen et al., 2001, Immunology, 103, 426-434). Murine T cell hybridomas are well documented model systems for the study of AICD. Most T cell hybridomas die within hours after activation by presentation of anti-TCR or anti-CD3 antibodies follows by IL-2 treatment. AICD could be characterized by the de novo synthesis of Fas (CD95) and its ligand (FasL) (Brunner et al., 1996, Int. Immunol., 8, 1017-1026). To compare the susceptibility of murine T cell hybridoma to AICD, 2B4.11 T hybridoma cells (Delgado et al., 2001, J. Immunol. 166, 1028-1040) were cultured in anti-CD3 coated 96 well plates (145-2C11 antibody; 4 µg/ml) during 18 hours in complete medium. Then, supernatants from A549 infected cells with either Ad encoding multifunctional cytokines or control supernatants (Ad encoding individual mIL-2, mIL-7, mIL-18, mIL-21 or empty adenovirus) were added for a 18 hours additional period. Recombinant murine IL-2 (R&D Systems, UK) was also used as positive control (10-20 ng/ml). AICD has been measured by flow cytometry analysis using a phycoerythrine-labeled mouse anti-mouse FasL specific antibody (Kay-10, Pharmingen, San Diego, USA) and an FITC-labelled Annexin V Apoptosis Detection kit (Pharmingen, San Diego, USA).

AICD was also measured in vivo after subcutaneous injection of adenoviruses encoding multifunctional fusion cytokines. In brief, C57BL/6 mice were injected one time subcutaneously with $2 \cdot 10^8$ iu of Ad-fusion (or as a control Ad encoding individual mIL-2, mIL-7, mIL-21 or empty adenovirus). Draining lymph nodes were then taken at different times post-injection (5, 8 and 18 hours). AICD was measured as described below on lymphocytes contained in the lymph node.

Quantification of VLS (Vascular Leak Syndrome Assay)

Vascular leak was studied by measuring the extravasation of Evans blue which, when given i.v., binds to plasma proteins, particularly albumin, and following extravasation can be detected in various organs as described (Rafi-Janajreh et al., 1999, J. Immunol. 163, 1619-1627). Vascular leak was induced by injecting i.v. $2 \cdot 10^9$ iu of murine IL-2 encoding adenoviral vector once per day for three days. Groups of five C57B1/6 mice were injected i.v. with PBS, empty adenovirus, Ad-mIL-2, Ad-mIL-2+Ad-mproIL-18 or Ad-fusions. On day 4, mice were injected i.v. with 0.1 ml of 1% Evans blue in PBS. After 2 h the mice were bled to death under anesthesia, and the heart was perfused with heparin in PBS. The lungs and liver, where maximum extravasation is known to occur, were harvested and placed in formamide at 37° C. overnight. The Evan's blue in the organs was quantified by measuring the absorbance of the supernatant at 650 nm. The VLS seen in Ad-cytokine treated mice was expressed as the percent increase in extravasation compared with that in PBS-treated controls. For histopathological studies, groups of five separate mice were injected with empty Ad or PBS, Ad-mIL-2, Ad-mIL-2/mL-7, Ad-mIL-2/proIL-18(K89A) and Ad-mIL-2/matureIL-18(K89A) as described earlier, and on day 4 lungs and liver were fixed in 10% formalin solution. The organs were embedded in paraffin, sectioned, and stained with hematoxylin and eosin. Perivascular infiltration was scaled by counting the number of lymphocytes infiltrating the vessel and averaging the minimum and maximum range for each group. Sera from injected mice were also collected for ASAT and ALAT measurement.

In Vivo Experiments

Murine P815, B16F10, RenCa and TC1 tumor cells were trypsinized, washed, and resuspended in PBS at $3 \times 10^6$ cells/ml. One hundred microliter of the cell suspension was then injected subcutaneously into the right flank of 6- to 7-week-old immunocompetent B6D2 mice. At day 7, 8 and 9 after injection, when tumors became palpable, the mice received three intratumoral injections of $5 \times 10^8$ iu of Ad-fusion or Ad controls diluted in 10 mM Tris-HCl pH 7.5, 1 mM $MgCl_2$. Tumors size and survival rate were evaluated for a 120 day time period.

For evaluation of the immunoadjuvant effect of Ad-fusions in combination with MVA-E7 vector, one hundred microliter of the TC1 cell suspension ($3 \times 10^6$ cells/ml) was injected intravenously into the tail vein of 6- to 7-week-old immunocompetent B6D2 mice. 39 days after injection, the mice received three intranasal injections of $5 \times 10^8$ iu of Ad fusion (Ad-mIL-2/proIL-18(K89A)) diluted in 10 mM Tris-HCl pH 7.5, 1 mM $MgCl_2$ at days 39, 46 and 53 and three subcutaneous injections of 5×10⁶ pfu of MVA-E7 at days 42, 49 and 56. Tumors size and survival rate were evaluated for a 120 day time period.

For evaluation of the immunoadjuvant effect of Ad-fusions in combination with MVA-FCU-1, one hundred microliter of the B16F10 cell suspension (3×10⁶ cells/ml) was injected subcutaneously into the right flank of 6- to 7-week-old immunocompetent B6D2 mice. At day 7, 8 and 9 after injection, when tumors became palpable, the mice received three intratumoral injections of 5×10⁸ iu of Ad-fusion (Ad-mIL-2/proIL-18(K89A)) diluted in 10 mM Tris-HCl pH 7.5, 1 mM MgCl₂ and 10⁷ pfu of MVA-FCU1. The prodrug 5-FC was given in the feeding water at a final concentration of 0.5%. Tumors size and survival rate were evaluated for a 80 day time period.

The statistical difference in the in vivo survival experiments between the different groups was assessed using Fischer exact application (Statistica 5.1 software, Statsoft Inc.) of the Kaplan-Meir survival curves. A P5.0.05 was considered statistically significant.

Histology, Immunohistochemistry or Flow Cytometry Analysis of In Vivo Response.

Tumors were established and injected with the various viruses as described above for in vivo experiments. On day 13, tumors were measured and excised. Tumor draining lymph nodes were also taken at the same time. For flow cytometry analysis, tumors were disrupted by collagenase (SIGMA) digestion, cells were stained with the indicated antibodies and population analyzed by cytofluorimetry (Paul et al., 2002, Cancer Immunol. Immunother. 51, 645-654).

Tumor P815 tissues were removed and directly embedded in OCT Compound on isopentane cooled on dried-ice. 5 µm sections were used for Hematoxylin-Eosin staining (structural observations by light microscopy) or for immunohistochemistry. Infiltrating cells and blood vessels detection were performed on methanol-acetone (50:50) fixed cryosections using following antibodies: rat anti-mouse CD4 (n° 553727-Pharmingen) at a dilution of 1/500, rat anti-mouse CD8 (n° 553027-Pharmingen) at a dilution of 1/500, rabbit anti-human CD3 (N1580-1/50 diluted-Dako) non-diluted, hamster anti-mouse CD11c (n° 553799-Pharmingen) at a dilution of 1/100, rat anti-mouse Ia-Ie (n° 556999-Pharmingen) at a dilution of 1/500, rat anti-mouse CD25-FITC (Pharmingen) at a dilution of 1/50, goat anti-mouse IL18-R (AF856—R&D Systems) at a dilution of 1/50, anti-mouse CD31 (n° 01951D-Pharmingen) at a dilution of 1/50 and rabbit anti-human von Willebrand factor (A0082-Dako) at a dilution of 1/100. First antibodies were incubated for 1 h 30 at room temperature, rinsed in TBS-0.1% Tween20. The primary antibodies were revealed by specific secondary antibodies rabbit anti-rat Ig (Z0494-Dako) at a dilution of 1/500, rabbit anti-hamster Ig (n° 6074102-Rockland) at a dilution of 1/500, horse anti-goat biotinylated 0.5% (Vectastain Elite PK6200-Vector) or rabbit anti-FITC HRP (P0404-Dako) coupled at a dilution of 1/100, incubated for 30 minutes and then rinsed in buffer. Horseradish peroxidase (HRP)-labeled polymer conjugated with the second rabbit antibody (EnVision+System n° K4003-Dako) or Streptavidin-HRP (Vector) was applied for 30 minutes, then rinsed and DiAminoBenzidine (DAB) was used as substrate. All slides were counterstained with Hematoxylin.

EXAMPLE 1

Construction of Adenoviruses Expressing Multifunctional Fusion Cytokines

The sequence encoding the multifunctional fusion cytokines were constructed as outlined in FIG. 1 and in Material and Methods. The fusions generated are listed below: mIL-2/mIFN-g, mIFN-g/mL-2, mIL-2/mL-7, mIL-2/mL-21, mIL-21/mL-2, mIL-2/mL-15, mIL-15/mL-2, mIL-7/mIL-15, mIL-15/mIL-7, mIL-15/mL-21, mIL-21/mL-15, mIL-2/mproIL-18, mproIL-18/mL-2, mIL-2/m matureIL-18, m matureIL-18/mIL-2, mIL-2/mproIL-18(K89A), mproIL-18(K89A)/mL-2, mIL-2/matureIL-18(K89A), matureIL-18(K89A)/mL-2. Fusion cytokines containing murine IL-2 mutants (D20I, N88R, N88G and Q126M) were also generated.

The sequence encoding each of these multifunctional cytokines was cloned in an adenovirus shuttle plasmid and used to generate E1 and E3-deleted adenovirus vectors. Single control cytokines were also cloned in an adenovirus shuttle plasmid (Ad-mIL-2, Ad-mIL-2 (D20I), Ad-mIL-2 (N88G), Ad-mIL-2 (N88R), Ad-mIL-2 (Q126M), Ad-mIFN-g, Ad-mIL-7, Ad-mIL-15, Ad-mIL-18, Ad-mIL-18 (K89A) and Ad-mIL-21).

Expression of multifunctional fusion cytokines in A549 cells infected with the different adenovirus vectors was analyzed by Northern and Western Blot. Northern Blot analysis revealed the correct size of specific mRNA of each fusion cytokine and of each control cytokine. Western Blot analysis using cytokine specific antibodies revealed a major band having the expected molecular weight for each individual fusion. In some cases, additional bands were observed, reflecting alternative splicing events or different glycosylation pattern. High expression and secretion levels were detected for almost all fusions (higher levels are detected in supernatants of cells infected with Ad-mIL-2/mproIL-18 and Ad-mIL-2/mproIL-18(K89A)), except for some of the IL-15 containing fusions and Ad-mIL-15 (see Example 6).

Amounts of secreted recombinant fusion cytokines were measured using a specific ELISA assay of culture supernatants after infection of A549 cells with adenoviral vectors encoding the IL-2/IL-18 fusion cytokines and compared to the amount secreted by cells infected with Ad encoding the individual cytokines.

TABLE 1

|  | mIL-2 (ng/ml) | mIL-18 (ng/ml) |
| --- | --- | --- |
| Empty Ad | 0 | 0 |
| Ad-mIL-2 | $7 \cdot 10^4$ | 0 |
| Ad-m mature IL-18 | 0 | $6 \cdot 10^4$ |
| Ad-mproIL-18 | 0 | 250 |
| Ad-mproIL-18(K89A) | 0 | 200 |
| Ad-mIL-2/matureIL-18 | $3 \cdot 10^3$ | $2.5 \cdot 10^3$ |
| Ad-mIL-2/matureIL-18 (K89A) | $4 \cdot 10^3$ | $4 \cdot 10^3$ |
| Ad-mIL-2/m proIL-18 | $3 \cdot 10^4$ | $3 \cdot 10^4$ |
| Ad-mIL-2/m pro IL-18(K89A) | $2.5 \cdot 10^4$ | $2.5 \cdot 10^4$ |

As was observed by Western Blot analysis, mIL-2/mproIL-18 and mIL-2/mproIL-18(K89A) were expressed in Ad-infected cells at highest levels in approximately the same range as mIL-2 alone but 100 times more than Ad-proIL-18 alone. Expression of mIL-2/matureIL-18 and mIL-2/matureIL-18 (K89A) was approximately one tenth that obtained with Ad-mIL-2 indicating that the lack of a prosequence is deleterious to the expression at least in the adenovirus system.

Stability of recombinant fusion cytokines was also assessed in vitro by Western Blot analysis. A549 cells were infected with Ad-mIL-2 or Ad-mproIL-18(K89A) alone, or the combination of Ad-mIL-2+Ad-mproIL-18(K89A) or with an adenovirus expressing the IL-2/IL-18 fusion (Ad-mIL-2/mproIL-18(K89A)). Supernatants were analyzed after 24 h, 48 h and 72 h post infection. Blots were probed with (a) a rabbit anti-mouse IL-2 antibody or (b) a rabbit anti-mouse IL-18 antibody Unexpectedly, a higher stability of IL-2 expression was observed for the mIL-2/mproIL-18 (K89A) fusion protein as compared to the cytokine alone or the combination of the two cytokines. Moreover, a higher IL-18 expression was also observed when the proIL-18 (K89A) entity is expressed as a fusion with mIL-2 (Ad-mIL-2/proIL-18(K89A) construct) rather than when expressed individually (Ad-mproIL-18(K89A) construct). On the basis of this results, it seems that the fusion of IL-2 with IL-18 allows to maintain a fixed ratio of both mIL-2 and mproIL-18(K89A) in contrast to the combination of Ad-mIL-2+Ad-mproIL-18(K89A).

The expression of the fusion cytokine mIL-2/mproIL-18 (K89A) was also evaluated by RT-PCR. Immunocompetent B6D2 mice bearing palpable P815 tumors were injected with $5 \times 10^8$ iu of empty Ad, Ad-mIL-2, Ad-mIL-2+Ad-mproIL-18 (K89A) or Ad-mIL-2/mproIL-18(K89A). Tumors were removed 72 hours after injection and mRNA were extracted. RT-PCR was carried out using oligonucleotide probes specific for mIL-2, mproIL-18 or sequences specific to the mIL-2/mproIL-18(K89A) fusion. As before, the injection of Ad-mIL-2/mproIL-18(K89A) resulted in the maintenance of a fixed ratio of both mIL-2 and mproIL-18(K89A) in contrast to the combination of Ad-mIL-2+Ad-mproIL-18(K89A).

EXAMPLE 2

In Vitro Functionality of the Fusion Cytokines

In Vitro Functionality of IL-2-Containing Fusions

Figure 2:
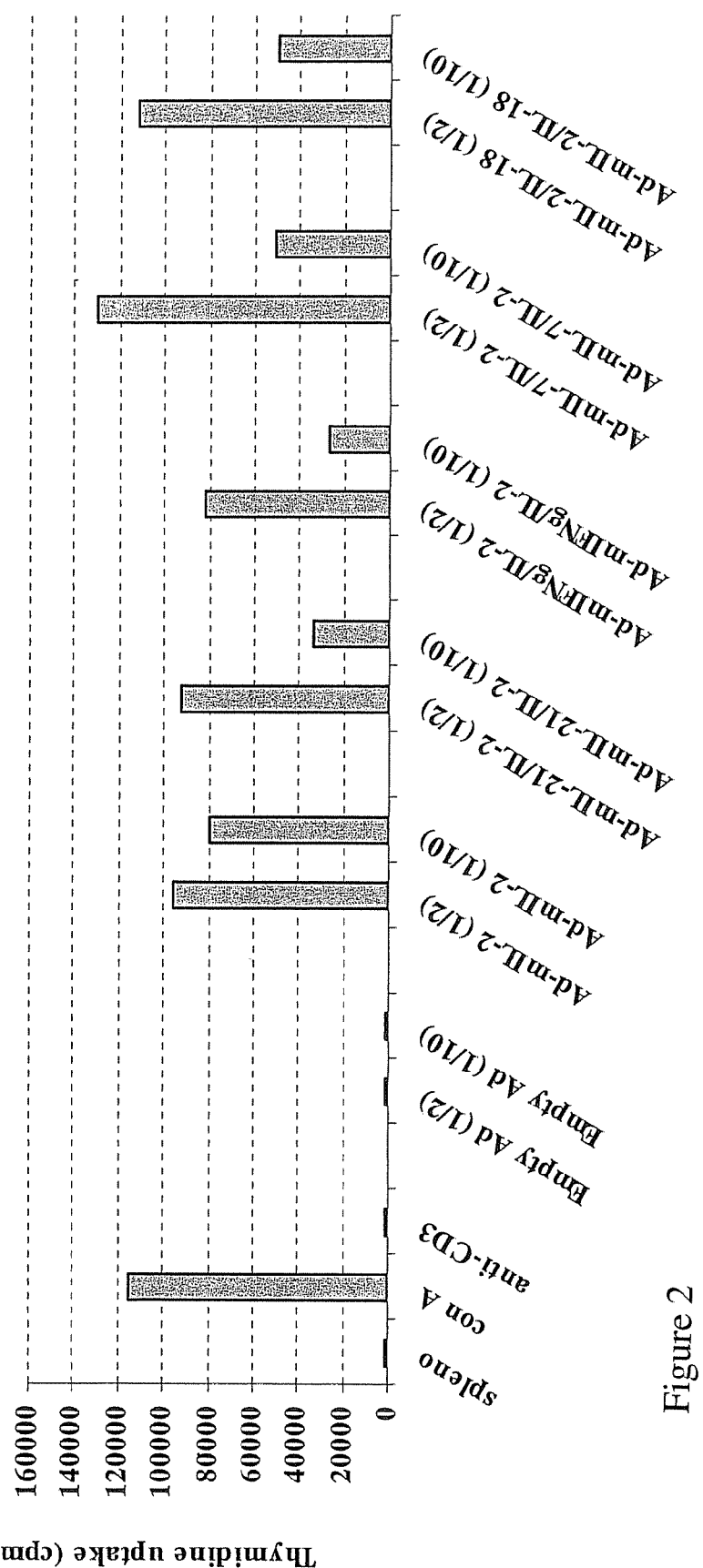

The effect of fusion proteins on T cell stimulation was analyzed by assessing the proliferation of murine splenocytes when incubated with anti-CD3 plus Ad-fusion cytokine supernatants as described in Material and Methods. IL-2 is known to be a strong inducer of CD3-pre-activated splenocyte proliferation. Briefly, the proliferation of murine splenocytes incubated with Ad-fusion supernatants was measured in a T cell proliferation assay. Supernatant concentrations were adjusted to have equivalent (20 μg/ml) content of total cytokine or fusion cytokine As illustrated in FIG. 2, a strong stimulation index was obtained with Ad-mIL-7/IL-2, and Ad-mIL-2/mproIL-18 supernatants (2, and 1.8 respectively), which was higher than that obtained with Ad-mIL-2. The T cell proliferation activity of the Ad-fusions expressing the IL-18 variant (K89A) was also analyzed by comparison to Ad expressing individual cytokines (Ad-mIL-2, Ad-mproIL-18 (K89A)) and the combination of the two (Ad-m-IL-2+Ad-mproIL-18(K89A)). The results confirm a stronger stimulation index provided by Ad-mIL-2/mproIL-18(K89A) than for Ad-mIL-2, Ad-mproIL-18(K89A) or the combination of the two. On the other hand, supernatants containing the fusions IL-21/IL-2, IL-15/IL-7, IL-2/IL-15 and IL-15/IL-21 show stimulation indices comparable with those obtained for IL-2 supernatants. No proliferation was observed with an empty virus supernatant.

In Vitro Functionality of IL-7-Containing Fusions

The in vitro functionality of IL-7-containing fusions was evaluated using an IL-7 dependent cell line—the murine pro-B 2E8 cell line—, which is able to grow only in the presence of IL-7 in the medium. The ability of supernatants of A549 cells infected with Ad-mIL-2/IL-7 and Ad-mIL-7/IL-2 to promote 2E8 proliferation was tested and compared to the Ad-mIL-7 supernatants and recombinant IL-7 as positive controls and an empty Ad as negative control.

Figure 3:
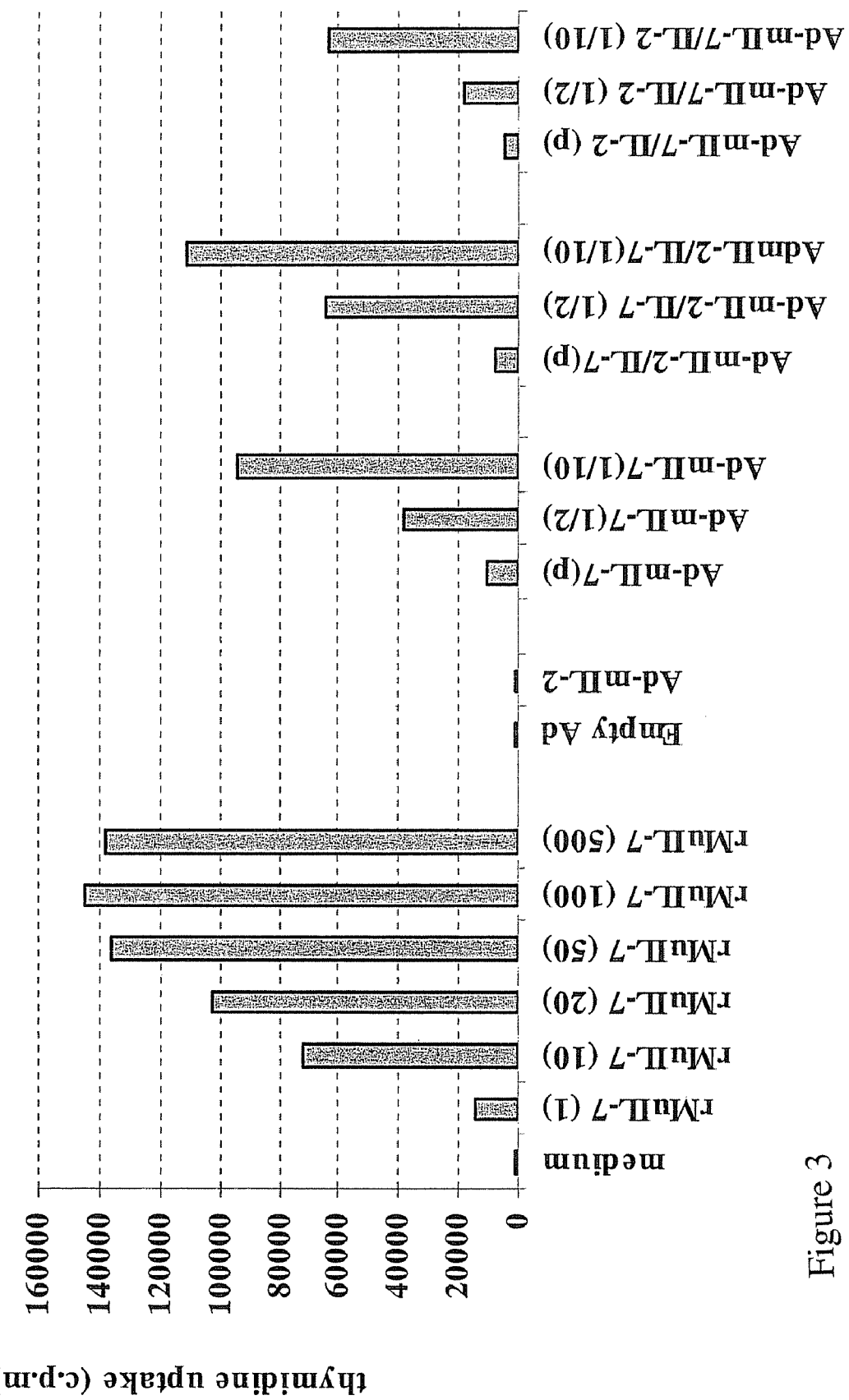

As expected, recombinant murine IL-7 induced the proliferation of 2E8 as Ad-mIL-7 supernatant. As illustrated in FIG. 3, the proliferation rate of 2E8 treated with Ad-IL-2/IL-7 supernatants is higher than that obtained with Ad-mIL-7 supernatant at the same dilutions. As a result, the proliferation rate obtained with ⅟₁₀-diluted Ad-IL-2/IL-7, Ad-IL-7/IL-2 and Ad-IL-7 supernatants is comparable to that obtained with 20, 10 and 15 ng/ml of recombinant murine IL-7 respectively. No proliferation was observed with an empty virus supernatant.

In Vitro Functionality of IL-18-Containing Fusions

Figure 4:
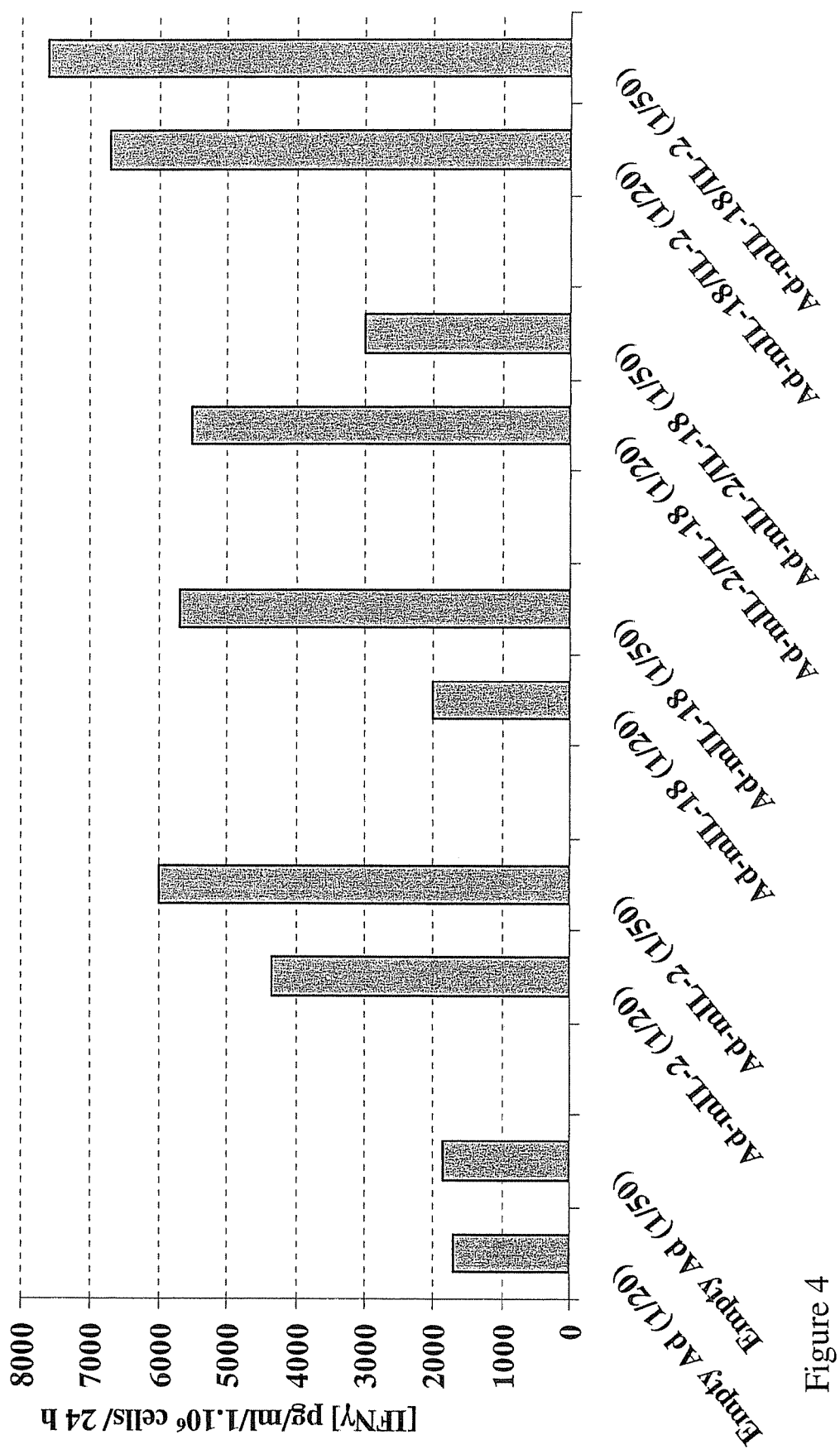
Figure 5:
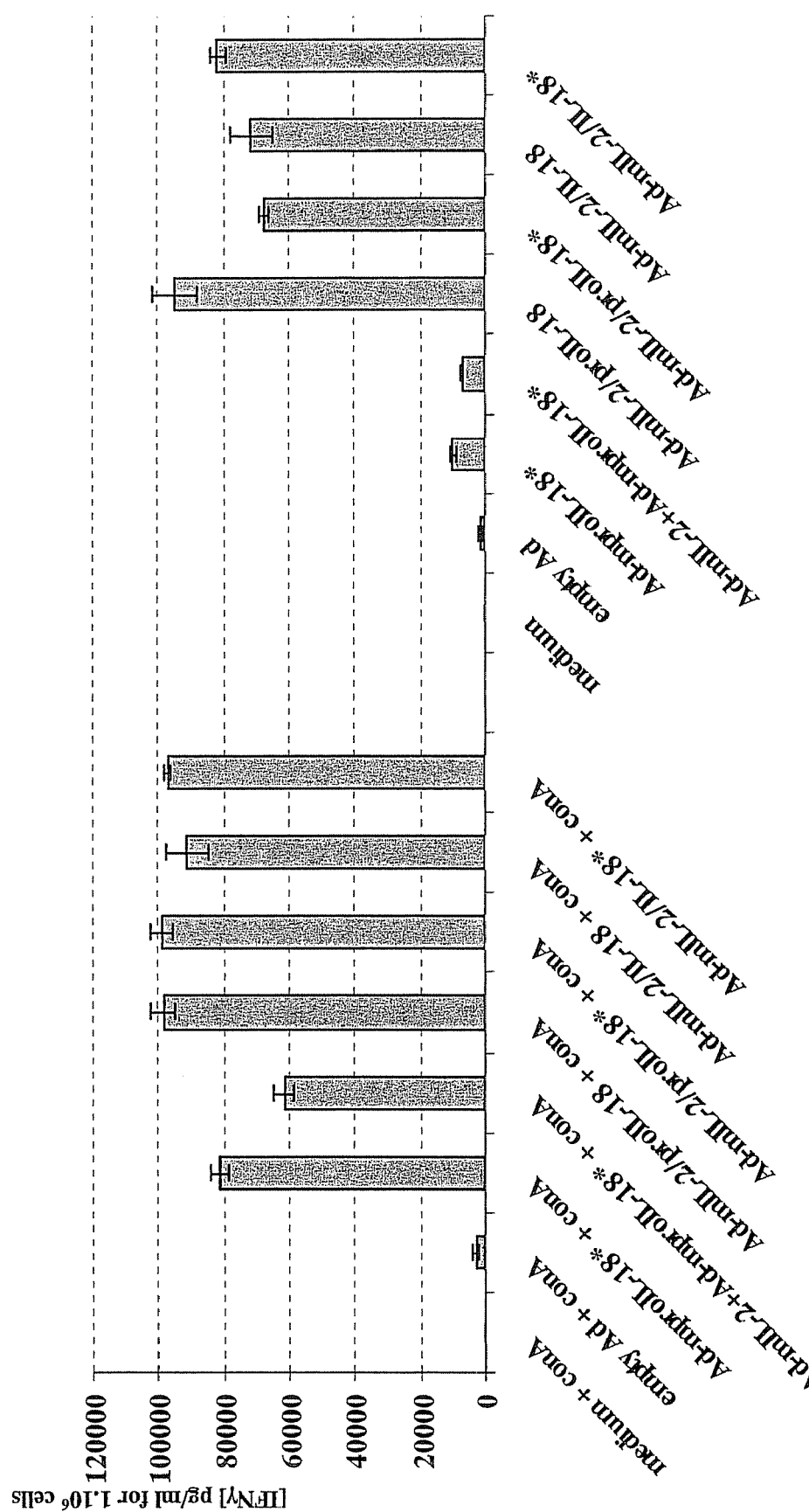

IL-18 is described as a strong inducer of IFN-g secretion both in vitro and in vivo. To evaluate the biological activity of IL-18-containing fusions, secretion of murine IFN-g by conA-primed murine splenocytes was quantified as described in Material and Methods. As a result and as illustrated in FIG. 4, ⅟₂₀-diluted supernatants containing Ad-mproIL-18/IL-2 induced a higher concentration of murine IFN-g in vitro (7 to 8 μg/ml/24 h/$10^6$ cells) in comparison to those induced by Ad-mIL-2 (4 μg/ml/24 h/$10^6$ cells), Ad-mproIL-18 (2 μg/ml/24 h/$10^6$ cells) and M-2/mproIL-18 (5.5 μg/ml/24 h/$10^6$ cells). These differences are statistically significant. The biological activity of IL-18(K89A)-containing fusion cytokines was also assessed by evaluating the secretion of murine IFNγ by conA-primed splenocytes. As illustrated in FIG. 5, supernatants containing IL-2/IL-18 fusions (mIL-2/mproIL-18, mIL2/matureIL-18, mIL-2/mproIL-18(K89A) and mIL-2/matureIL-18(K89A), respectively) induce slightly higher levels of IFNg (approximately 100 ng/ml/$10^6$ cells) than supernatants containing mproIL-18(K89A) alone or the combination of AdmIL-2+Ad-mproIL-18(K89A) (approximately 80 and 60 ng/ml/$10^6$ cells respectively).

In a second series of experiments, the secretion of IFNg was also quantified using unprimed murine splenocytes. Unexpectedly, as illustrated in FIG. 5, un-primed splenocytes were stimulated to secrete high level of IFNγ only after activation with Ad supernatants containing mIL-2/mproIL-18, mIL-2/mproIL-18(K89A), mIL-2/matureIL-18 and mIL-2/matureIL-18(K89A) fusions cytokines. This suggests a novel activity associated with the IL-2/IL-18 fusion cytokines, which is not seen with individual cytokines or a mixture of the two.

In Vitro Functionality of IFN-g-Containing Fusions

The functionality of the IFN-g gene product contained in the fusions of the invention was estimated using the ability of this cytokine to upregulate activation markers on APCs and tumor cells. In a simple experiment, Ad-fusion supernatants were added to murine splenocytes in vitro during 72 hours, then the upregulation of activation markers specific for murine splenocytes, APCs and CD8+ lymphocytes was assessed by flow cytometry analysis for change in T lymphocytes (CD8+), and dendritic cell (CD11b) as well as MHC class I, MHC class II markers using specific antibodies as described in Material and Methods.

TABLE 2

Upregulation of activation markers on murine splenocytes

| Ad fusion | MHCI+ | MHCII+ | CD11b+ | CD8+ |
|---|---|---|---|---|
| IFN-g rec | + | + | − | − |
| Empty Ad | ++ | ++ | + | + |
| Ad-mIL-2 | + | + | − | ++ |
| Ad-mIFN-g | +++ | ++ | + | + |
| Ad-mIL-2/IFN-g | ++++ | ++++ | +++ | +++ |
| Ad-mIFN-g/IL-2 | +++ | +++ | ++ | +++ |

− = no positive cells
+ = between 1 to 5% of positive cells
++ = between 10 to 20% of positive cells
+++ = between 20 to 40% of positive cells
++++ = more than 40% of positive cells As illustrated in Table 2, supernatants of cells infected with AdIL-2/IFN-g fusion are most potent to induce the upregulation of MHC class I and class II molecules in vitro but also unexpectedly to increase dramatically the number of APCs (CD11b$^+$) and CD8$^+$ T lymphocytes. The Ad-IFN-g/IL-2 supernatants induce the same level of response as Ad-IFN-g with respect to these markers. IL-2 induces a low level of activation of these cell populations.

In Vitro Ability of Fusion Proteins to Increase of Effector Cell Cytotoxicity

Activities of multifunctional cytokines were assayed for CTL and NK cytotoxicity as described in Material and Methods. Supernatants from A549 cells infected with Ad-fusion were incubated during 7 days with murine splenocytes. The results are summarized in Table 3.

TABLE 3

Increase of effector cell cytotoxicity

| Ad-fusion | CTL activity | NK activity |
|---|---|---|
| Empty Ad | − | − |
| Ad-mIL-2 | ++ | +++ |
| Ad-mIFN-g | − | + |
| Ad-mIL-7 | − | − |
| Ad-mproIL-18 | ++ | ++ |
| Ad-mIL-21 | − | ++ |
| Ad-mIL-2/IFN-g | + | ++ |
| Ad-mIFN-g/IL-2 | + | +++ |
| Ad-mIL-2/IL-7 | + | + |
| Ad-mIL-7/IL-2 | +++ | ++++ |
| Ad-mIL-2/proIL-18 | +++ | +++ |
| Ad-mproIL-18/IL-2 | + | ++ |
| Ad-mIL-2/IL-21 | ++ | + |
| Ad-mIL-21/IL-2 | − | ++ |

− = no specific lysis
+ = between 20 to 40% lysis to an E/T ratio of 50/1
++ = between 40 to 60% lysis to an E/T ratio of 50/1
+++ = between 60 to 80% lysis to an E/T ratio of 50/1
++++ = between 80 to 100% lysis to an E/T ratio of 50/1

As shown in Table 3, supernatants from A549 infected cells with Ad-mIL-7/IL-2 and Ad-mproIL-18/IL-2 induced a high cytotoxic activity both on CTL and NK activity in vitro. These activities are highly superior to those obtained with Ad-mIL-2, Ad-mIL-7 and Ad-mproIL-18 supernatants. Moreover, the Ad-mIFN-g/IL-2 supernatants induced a high response on NK cytotoxicity but not on CTL response.

In addition, the effect of the mIL-2/mproIL-18(K89A) fusion was assessed for CTL and NK cytotoxic activities and compared to that of each cytokine alone (mIL-2 or mproIL-18(K89A) respectively), or the combination of mIL-2+ mproIL-18(K89A). Murine splenocytes were cultured for 7 days with supernatants from A549 cells infected with the corresponding Ad (Ad-mIL-2, Ad-mproIL-18(K89A), Ad-mIL-2+Ad-mproIL-18(K89A) and Ad-mIL-2/mproIL-18(K89A)). Supernatant concentrations were adjusted to have equivalent (20 µg/ml) content of total cytokine or fusokine. The results show that supernatants from A549 infected cells with Ad-mIL-2/proIL-18(K89A) fusion induced cytotoxic activity on both P815 and YAC target cells. Unexpectedly, the lytic activity by splenocytes cultured with mIL2/proIL18(K89A) fusion was greater than that observed by splenocytes cultured with supernatants containing individual cytokines or the mixture mIL-2+mproIL-18(K89A).

Induction of CD8, NK and NKT Cells

The capacity of the fusion cytokines to induce proliferation of both innate and adaptative immune effector cells was evaluated. For this purpose, the percentage of CD8 T lymphocytes, NK and NK/NKT effector cells was quantified by flow cytometry using murine splenocytes cultured for one week with Ad-fusion supernatants. The results of this assay are presented in Table 4

TABLE 4

Induction of CD8, NK and NKT proliferation

| Ad-fusion | CD8 (%) | NK (%) | NK-T/NK (%) |
|---|---|---|---|
| mIL-21 rec | 27 | 5 | 25 |
| Empty Ad | 14 | 3 | 7 |
| Ad-mIL-2 | 58 | 5 | 11 |
| Ad-mproIL-18 | 41 | 16 | 45 |
| Ad-mIL-21 | 49 | 13 | 38 |
| Ad-mIL-2/mproIL-18 | 51 | 15 | 60 |
| Ad-mproIL-18/IL-2 | 55 | 14 | 7 |
| Ad-mIL-2/IL-21 | 43 | 15 | 53 |
| Ad-mIL-21/IL-2 | 45 | 11 | 54 | mIL-21 rec = recombinant murine IL-21 (20 ng/ml)

As illustrated in Table 4, all the Ad-fusion supernatants tested induce the same proportion (approximately 50%) of CD8$^+$ T lymphocytes (specific effector cells) as Ad-mIL-2 supernatant. Moreover and in contrast to Ad-mIL-2 or Ad-mIL-21, the Ad-fusion (Ad-mIL-2/mproIL-18, Ad-mIL-2/IL-21 and Ad-mIL-21/IL-2) supernatants induce a very impressive proportion (>50%) of NK/NKT$^+$ cells. NK1.1$^+$ cells were also significantly induced in the presence of Ad supernatants encoding these fusion proteins.

Moreover, it has been observed that incubation of murine splenocytes with mIL-2/proIL-18(K89A) induces a dramatic increase in the percentage of both CD8$^+$ (50%), NK$^+$ (18%) and NK/NKT$^+$ (51%) cells in comparison with splenocytes cultured with empty Ad, Ad-mIL-2 and Ad-mproIL-18 (K89A)-generated supernatants.

Effect of the Fusion Cytokines on the Maturation of Murine Dendritic Cells

Bone marrow derived dendritic cells were obtained from C57B16 mice as previously described (Fields et al., 1998, J. Immunother. 21, 323-339). Immature dendritic cells were incubated with Ad-fusion supernatants for 48 hours before phenotyping analysis by flow cytometry analysis. Upregulation of maturation factor of murine dendritic cells was determined by measuring the percentage of CD80, CD86 and MHC II-Iab markers using specific monoclonal antibody (Pharmingen). Supernatants obtained from cells infected with Ad-mIL-7/IL-2 and Ad-mIL-2/mproIL-18(K89A) were shown to upregulate the CD80, CD86 and MHCII markers, reflecting maturation of murine DCs, although at a slightly lower level than a positive control (LPS, 1 µg/ml, DIFCO) or supernatant from Ad-mIL-7.

In conclusion, adenovirus vectors expressing multifunctional cytokines are fully functional, exhibit in some cases a higher biologically activity than simply the additive activity of the individual cytokines forming the fusion. Unexpected activities were also detected for some of these fusions, such as the ability of the IL2/IL-18 fusion (especially mIL-2/mproIL-18(K89A)) to activate murine NKT cells and the ability of IL-7/IL-2 and IL2/IL-18 (especially mIL-2/mproIL18 and mIL-2/mproIL-18(K89A)) fusions to induce murine DC maturation.

EXAMPLE 3

Toxicity of Fusion Cytokines

In addition to its role in the initial activation of T and NK cells, IL-2 has a critical role in the maintenance of peripheral tolerance (Lenardo, 1996, J. Exp. Med. 183, 721-724). In this respect, IL-2 has a central importance in Fas-mediated activation-induced cell death (AICD), a process that leads to the elimination of self-reactive T cells (Lenardo, 1996, J. Exp. Med. 183, 721-724; Van Parijs et al., 1999, Immunity 11, 281-288). As a result of this pivotal role in AICD, the T cells generated in response to tumor vaccines containing IL-2 may interpret the tumor cells as self and the tumor-reactive T cells may be killed by AICD-induced apoptosis.

It has been described recently that AICD limits effector function of CD4 tumor-specific T cells and decrease T cell effector activity (Saff et al., 2004, J. Immunol. 172, 6598-6606). IL-2 is also known to be critically required for the activation of CD4+ CD25+ T cell suppressor function (Thornton et al., 2004, J. Immunol. 172, 6519-6523; Shimizu et al., 1999, J. Immunol. 163, 5211-5218). Although IL-2 therapy has yielded encouraging results in the treatment of certain types of cancer, its use is limited by dose-dependent toxicity characterized by weight gain, dyspnea, ascites, and pulmonary edema. These signs of toxicity result from increased capillary leak, also known as vascular leak syndrome (VLS) (Rosenstein et al., 1986, J. Immunol. 137, 1735-1742; Baluna and Vitetta, 1997, Immunopharmacology 37, 117-132; Baluna et al., 1999, Proc. Natl. Acad. Sci. USA 96, 3957-3962). For this reason, the toxicity of the fusion cytokines of the invention was compared to that provided by IL-2 in AICD and VLS assays.

AICD Assays

The percentage of two apoptotic markers (Annexin and Fas ligand (FasL)) was evaluated in AICD assays both in vitro and in vivo, as described in Material and Methods. The results are presented in Table 5.

TABLE 5

In vitro toxicity of fusion cytokines. Measurement of AICD
(results are presented as percentage of total gated cells)

| Ad-fusion | Annexin V+ | FasL+ |
|---|---|---|
| Medium | 40 | 7 |
| mIL-2 rec (10 ng/ml) | 65 | 24 |
| Empty Ad | 42 | 8 |
| Ad-mIL-2 | 67 | 25 |
| Ad-mIL-7 | 50 | 22 |
| AdmIL-18 | 55 | 23 |
| Ad-mIL-2/IL-18 | 48 | 18 |
| Ad-mIL7/IL-2 | 36 | 9 |

In vitro, Ad-mIL-7/IL-2 and Ad-mIL-2/IL-18 supernatants protect 2B4.11 cells from AICD as reflected by the low level of the two apoptotic markers Annexin V and FasL (36 and 48% of Annexin V+ cells and 9 and 18% FasL+ cells, respectively). In marked contrast, treatment with recombinant murine IL-2 and Ad-mIL-2 induced high apoptosis (65 and 67% of Annexin V+ cells and 24 and 25% FasL+ cells, respectively).

AICD was evaluated in vivo in the draining lymph nodes, 8 hours after subcutaneous injection of Ad-fusions or Ad-IL-2. Table 6 summarizes the results obtained. The results are representative of two experiments, each with three mice.

TABLE 6

In vivo toxicity of fusion cytokines. Measurement of AICD
(results are presented as percentage of total gated cells)

| Ad-fusion | Annexin V+ | FasL+ |
|---|---|---|
| Empty Ad | 2 | nt |
| Ad-mIL-2 | 48 | 29 |
| Ad-mIL-2/mproIL-18 | 19 | 18 |
| Ad-mIL-2/mproIL-18(K89A) | 9 | 15 |
| Ad-mIL7/IL-2 | 6 | 12 |

As illustrated in Table 6, flow cytometry analysis of the cells contained in the lymph nodes revealed that injection of Ad-mIL-2 induces a strong AICD in vivo (48% Annexin $V^+$ and 29% $FasL^+$ cells). In marked contrast, IL-2/mproIL-18 (19% Annexin $V^+$ and 18% $FasL^+$ cells), mIL-2/mproIL-18 (K89A) (9% Annexin $V^+$ and 15% FasL+ cells) and even better IL-7/IL-2 (6% Annexin $V^+$ and 12% $FasL^+$ cells) protect T cells from IL-2 induced AICD.

In conclusion, both in vitro and in vivo AICD assays demonstrate the low apoptosis status conferred by the fusion proteins of the invention.

VLS Assays

Figure 6:
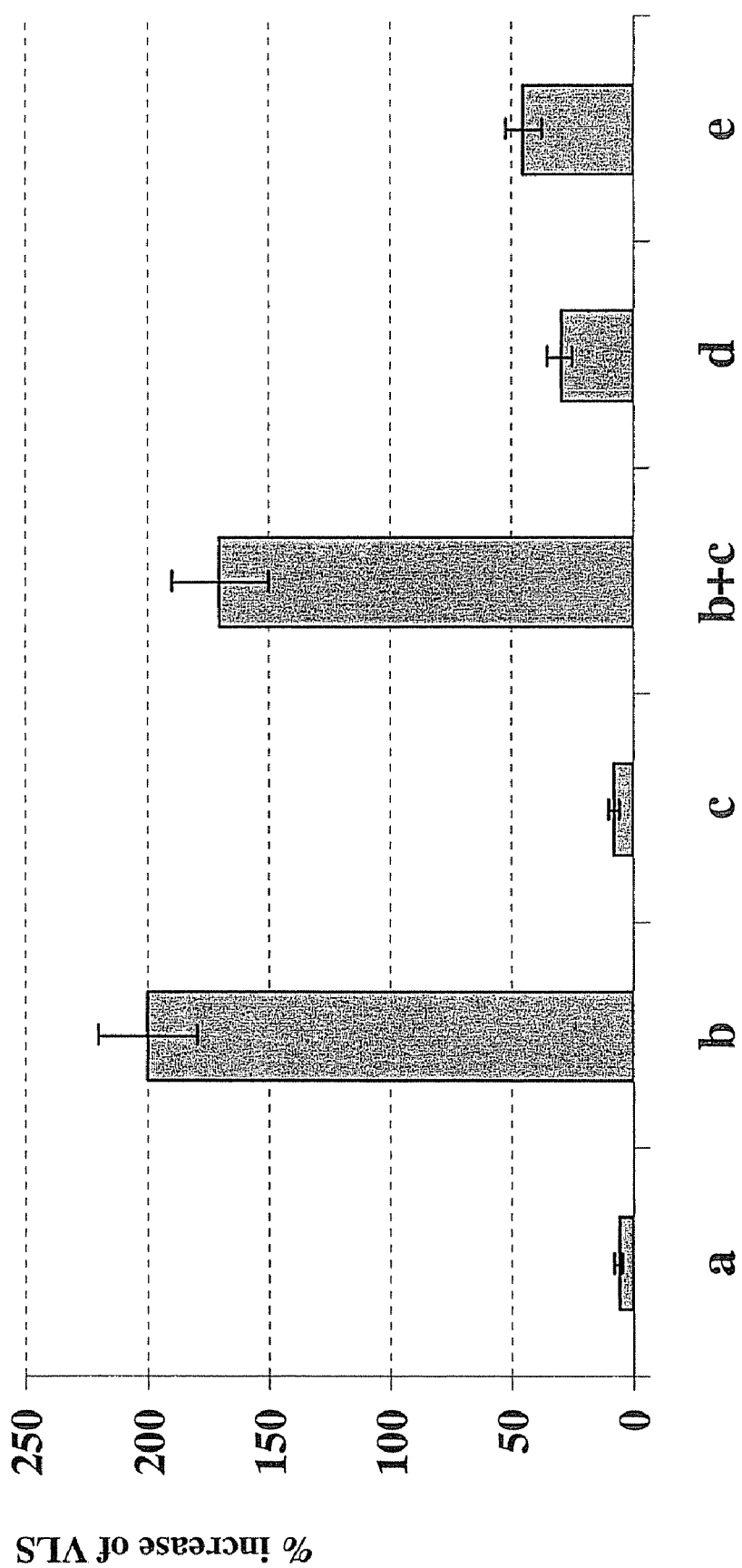
FIG. 6 illustrates the in vivo analysis of fusion cytokine systemic and cell toxicity. Assessment of VLS syndrome induced by i.v. treatment of mice with $2 \cdot 10^9$ iu of an empty Ad (a), Ad-mIL-2 (b), Ad-mproIL-18(K89A) (c), the combination of Ad-mIL-2+Ad-mproIL-18(K89A) (b+c), Ad-mIL-2/matureIL-18(K89A) (d) and Ad-mIL-2/proIL-18(K89A) (e).

To assess the toxicity of candidate fusion cytokines, groups of healthy C57B1/6 mice were administered intravenously with high doses of empty Ad or adenoviral vectors encoding mIL-2, mproIL-18(K89A), the combination of mIL-2+ mproIL-18(K89A) and the fusion cytokines mIL-2/mIL7, mIL-2/mproIL-18(K89A) and mIL-2/matureIL-18(K89A). As illustrated in FIG. 6, the two fusion versions mIL-2/ mproIL-18(K89A) and mIL-2/matureIL-18(K89A) induce much less vascular leak than does mIL-2 and the combination of mIL-2+mproIL-18(K89A). A reduced vascular leak was also observed in mice injected with Ad-mIL-2/mIL-7. These data demonstrate that the genetic fusions of IL-2 and proIL-18(K89A) as well as IL-2 and IL-7 dramatically reduce cytokine toxicity associated with vasopermeability.

Moreover, the reduced toxicity provided by the fusion cytokine was confirmed by quantification of hepatic enzymes ASAT and ALAT in injected mice sera. The results demonstrate the absence of hepatic toxicity after treatment with Ad-mIL-2 or Ad-Fusion cytokines.

EXAMPLE 4

In Vivo Functionality of Fusion Cytokines

The anti-tumoral activity of the fusion cytokines of the invention was investigated in four tumor models (P815, RenCa, B16F10 and TC1). Tumors were established in B6D2 mice and tumor growth and mouse survival were evaluated following three intratumoral injections of Ad-fusions ($5 \times 10^8$ iu) for a 120 day time period. Table 7 summarizes the results obtained in the four tumor models.

TABLE 7

Anti-tumor activity in murine tumor models (results are expressed
in percentage of tumor-free mice over a period of 120 days)

| Ad-fusion | P815 | B16F10 | RenCa | TC1 |
|---|---|---|---|---|
| Ad-mIL-2 | 0 | 60 | 80 | 30 |
| Ad-mIL-7 | 0 | 0 | 10 | 0 |
| Ad-mproIL-18 | 0 | 0 | 20 | 10 |
| Ad-mproIL-18(K89A) | 0 | 0 | 10 | 10 |
| Ad-mIL-21 | 10 | 0 | 30 | nt |
| Ad-mIFN-g | 5 | 0 | 15 | nt |

TABLE 7-continued

Anti-tumor activity in murine tumor models (results are expressed in percentage of tumor-free mice over a period of 120 days)

| Ad-fusion | P815 | B16F10 | RenCa | TC1 |
|---|---|---|---|---|
| Ad-mIL-2 + Ad-mproIL-18 | 10 | 40 | 80 | nt |
| Ad-mIL-2/mproIL-18 | 40 | 30 | 70 | 40 |
| Ad-mIL-2/mproIL-18(K89A) | 70 | 50 | 90 | 60 |
| Ad-mIL-7/IL-2 | 20 | 20 | 70 | 30 |
| Ad-mIL-21/IL-2 | nt | 10 | 50 | nt |
| Ad-mIFN-g/IL-2 | nt | 10 | 60 | nt | nt = not tested

As illustrated in Table 7, Ad-mIL-2/mproIL-18 is the most effective fusion for curing tumors from various origins (especially murine mastocytomas (P815), renal carcinomas (RenCa) and HPV-transformed tumors (TC1). More importantly, the antitumoral protection observed for this fusion cytokine is significantly higher than that conferred by administration of a vector encoding the individual cytokines (see Ad-mIL-2 or Ad-mproIL-18) as well as the co-administration of vectors encoding separately these cytokines (Ad-mIL-2+ Ad-mproIL-18), at least in the RenCa, P815 and TC1 tumor models. Moreover, the use of a mutated form of IL-18 (K89A) dramatically increases the anti-tumor efficacy in all tumor model (see Ad-mIL-2/mproIL-18(K89A) providing 70% of tumor free mice in P815 model, 50% in B16F10 model, 90% in the RenCa model and 60% in the TC1 model). Significant anti-tumor activity was also observed in several animal models treated with Ad-mIL-7/IL-2. Ad-mIL-21/IL-2 and Ad-mIFN-g/IL-2 also provide anti-tumor protection to the same extent as Ad-mIL-2.

The in vivo depletion of CD8, NK and CD4 cells was performed as described by Slos et al., 2001, Cancer Gene Ther. 8, 321-332). The survival data show that the anti-tumor activity of Ad-mIL-2/mproIL-18(K89A) was strictly dependent on CD8 and NK cell activity. Interestingly, CD4 depletion increased the in vivo activity of intra-tumor administration of the fusion cytokine.

Importantly, it should be noted that no immune response against the fusion cytokine was observed in vivo in the serum of treated mice (data not shown).

The in vivo anti-tumoral efficacy of the fusion cytokines was also correlated with the analysis of intratumoral infiltrates and of proximal activation of both innate and adaptative immune effector cells (in the draining lymph nodes) by histology, immunohistochemistry or flow cytometry in the P815 model as described in Material and Methods. The results are presented in Table 8.

TABLE 8

Analysis of tumor infiltrates after intratumoral injection of Ad-fusions.

| | NI | Ad-empty | Ad-mIL-2 | Ad-mIL-7/IL-2 | Ad-mIL-2/IL-18 | Ad-mIL-2/IL-18* |
|---|---|---|---|---|---|---|
| CD3 | + | + | ++ | ++ | ++++ | ++++ |
| CD4 | + | + | +++ | +++ | + | ++ |
| CD8 | − | − | − | + | +++ | +++ |
| CD25 | + | + | + | ++ | +++ | ++ |
| Ia-Ie | − | + | + | + | ++ | +++ |
| IL-18R | + | + | + | + | ++++ | +++ |
| CD-31 | +++ | +++ | +++ | +++ | +++ | ++ |

TABLE 8-continued

Analysis of tumor infiltrates after intratumoral injection of Ad-fusions.

| | NI | Ad-empty | Ad-mIL-2 | Ad-mIL-7/IL-2 | Ad-mIL-2/IL-18 | Ad-mIL-2/IL-18* |
|---|---|---|---|---|---|---|
| vonW necrosis | +<br><5% | +<br><10% | +<br><10% | ++<br><5% | +++<br>30-40% | ++++<br>70-80% |

− = no positive cells
+ = between 1 to 5% of positive cells
++ = between 10 to 20% of positive cells
+++ = between 20 to 40% of positive cells
++++ = more than 40% of positive cells As illustrated in Table 8, following Ad-fusion injections, immunohistochemistry analysis reveals that tumors injected with Ad-mIL-2/mproIL-18 and Ad-mIL-2/mproIL-18 (K89A) are highly necrotic. Moreover, immuno-histology demonstrates pronounced changes in infiltrate patterns differing from initial tumor histology, with an increase in the numbers of $CD8^+/CD25^+$-activated T cells, $CD4^+$ T cells and APCs. In addition, injected tumors clearly show upregulation of the IL-18 receptor. Such changes are also observed in P815 tumors injected with Ad-mIL-2 and Ad-mIL-7/IL-2 although at a lower level than with Ad-mIL-2/mproIL-18 or Ad-mIL-2/mproIL-18 (K89A). Surprisingly, tumors injected with Ad-mIL-2/mproIL-18(K89A) are highly positive for the von Willebrand factor suggesting the formation of new blood vessels.

Similar results were observed in the P815 tumor draining lymph nodes. Further, intratumoral injections of Ad-mIL-2/mproIL-18 and Ad-mIL-2/mproIL-18(K89A) do not induce any AICD in the tumor draining lymph nodes. This is in contrast with P815 tumors treated with Ad-mIL-2. Moreover, in mice treated with Ad-mIL-2/mproIL-18(K89A) and Ad-mIL-7/IL-2, an increase of immune cells (×30 to ×40) was observed in the lymph nodes, whereas a lower number of immune cells was detected in the lymph nodes of mice treated with Ad-MIL-2. This augmentation correlates with a dramatic decrease of the number of tumor cells. This shows clearly the inverse correlation between the total number of cells in the tumor and the total number of cells in the draining lymph node. The immune effector cells present in the lymph nodes following intratumoral injection of Ad-mIL-2/mproIL-18 (K89A) and Ad-mIL-7/IL-2 are mainly activated CD8+ T lymphocytes ($CD3^+/CD69^+$; $CD8^+/CD25^+$) and also activated APCs such as mature dendritic cells ($CD11c^+/MHCII^+$). The proportion and the number of these effector cells is higher following injection with Ad-mIL-2/mproIL-18 (K89A) and Ad-mIL-7/IL-2 than with Ad-mIL-2, Ad-mproIL-18(K89A), Ad-mIL-7 alone or the combination of AdmIL-2+Ad-mproIL-18(K89A).

EXAMPLE 5

Evaluation of the Immunoadjuvant Effect of Ad-Fusions for Specific Immunotherapy The immunoadjuvant effect of Ad-fusion was evaluated in the TC1 metastatic model. TC1 cells were injected by the intravenous route in order to establish metastasis in the lung of C57B16 mice. Several Ad-fusion were administered 10 days later by the intranasal or intratracheal routes to allow the expression of fusion protein in the metastasis environment in the lungs and also to induce a mucosal immunity. Administration of Ad-mIL-2/IL-18 by the intranasal or the intratracheal routes induced total IgA in the vaginal washes of the treated mice 15 days after adenovirus administration. The level of total IgA was similar following intranasal or intratracheal administration. Moreover, the rate of anti-adenovirus neutralizing antibody is significantly lower after Ad-mIL-2/IL-18 administration than after empty adenovirus or Ad-mIL-2 administration. These results could be of importance, in that they indicate that potentially re-administration of the fusion-encoding adenoviral vectors could be facilitated due to the lower humoral immune response against these vectors.

Moreover, RT-PCR analysis showed that these two "mucosal" routes allow a very good expression of the fusion cytokine IL-2/IL-18 in the lung and more precisely in the TC1 metastasis present in the lung. Importantly, the expression of the fusion correlated a strong in vivo effect since the growth of TC1 metastasis was stopped in treated mice.

All together, these results indicate the potential utility of the fusion cytokines as adjuvant for cancer or viral vaccine.

Figure 7:
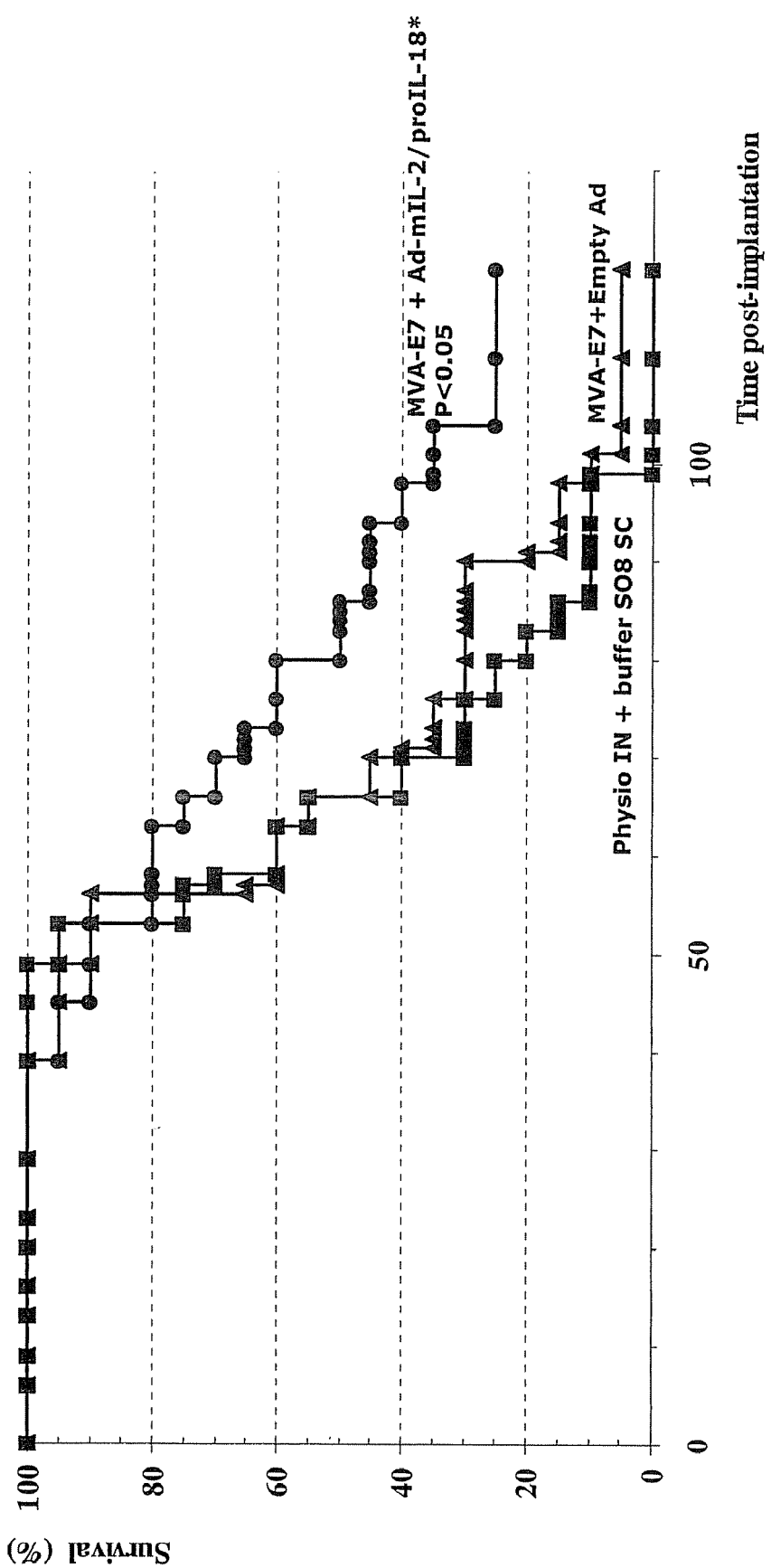
FIG. 7 illustrates the immunoadjuvant effect of Ad-mIL-2/proIL-18(K89A) in combination with MVA-E7. As before, * represents the mutation (K89A).

The use of the fusion cytokine mIL-2/proIL-18(K89A) as a genetic adjuvant for a cancer-specific vaccine was also assessed. First, evaluation of the immunoadjuvant effect of Ad-fusions was performed in the TC1 metastatic model in combination with a MVA vector expressing a non oncogenic and membrane anchored E7 antigen of HPV-16 strain driven by the 7.5K promoter (see WO99/03885). The mice received three intranasal injections of $5 \times 10^8$ iu of Ad-mIL-2/proIL-18 (K89A) at days 39, 46 and 53 and three subcutaneous injections of MVA-E7 at days 42, 49 and 56. Tumors size and survival rate were evaluated for a 120 day time period. As illustrated in FIG. 7, the combination of a tumor specific antigen expressing vector as MVA-E7 with an adenovirus expressing a IL-2/IL-18 fusion strongly enhanced the tumor-specific immune response in the highly late metastatic TC1 model. This combination could increase the survival of treated animals and decrease the number of residual metastasis.

Figure 8:
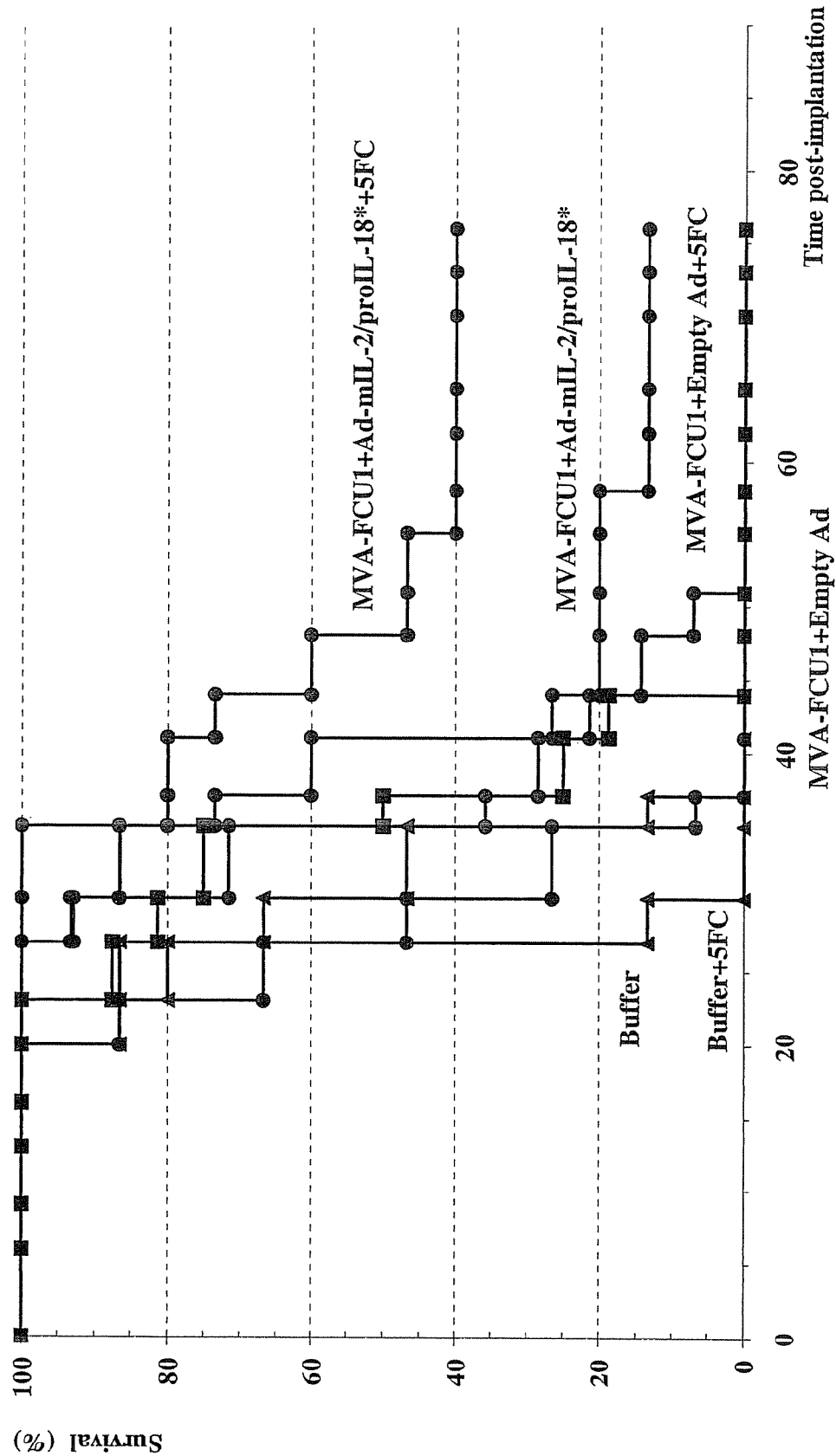
FIG. 8 illustrates the immunoadjuvant effect of Ad-mIL-2/proIL-18(K89A) in combination with MVA-FCU1. As before, * represents the mutation (K89A).

The immunoadjuvant effect of Ad-mIL-2/proIL-18 (K89A) was also evaluated in in the B16F10 model in combination with a MVA vector expressing the FCU-1 suicide gene placed under control of the chimeric 11k/7.5K promoter (WO99/54481). One hundred microliter of the B16F10 cell suspension ($3 \times 10^6$ cells/ml) was injected subcutaneously into the right flank of 6- to 7-week-old immunocompetent B6D2 mice. At day 7, 8 and 9 after injection, when tumors became palpable, the mice received three intratumoral injections of $5 \times 10^8$ iu of Ad-mIL-2/proIL-18(K89A) diluted in 10 mM Tris-HCl pH 7.5, 1 mM $MgCl_2$ and $10^7$ pfu of MVA-FCU1. The prodrug 5-FC was given in the feeding water at a final concentration of 0.5%. Tumors size and survival rate were evaluated for a 80 day time period. As illustrated in FIG. 8, the combination of Ad-mIL-2/proIL-18(K89A) with MVA-FCU1 clearly improved the antitumoral efficacy of a suicide gene therapy approach. This is an indication of the potent adjuvant effect of the fusion cytokine mIL-2/proIL-18 (K89A) with a chemotherapy-based strategy These results clearly demonstrate the potential of the Ad-fusion mIL-2/proIL-18(K89A) of the present invention as a genetic adjuvant for vaccination in combination with immunogen (e.g. tumor-specific antigens such as HPV-16 E7) and for cancer-specific vaccination in combination with a suicide gene therapy and appropriate chemotherapy.

EXAMPLE 6

IL-15 Containing Fusion Cytokines

The IL-15 containing Ad constructs are described in Example 1 (mIL-2/mL-15, mIL-15/mL-2, mIL-7/mL-15, mIL-15/mL-7, mIL-15/mL-21, mIL-21/mL-15). In addition, the fusion of mIL-15 to mproIL-18(K89A) was also performed using the same construction schema described in Material and Methods and in Example 1. It should be noted that in the constructs where IL-15 is located at the NH2 terminus of the fusion (mIL-15/mIL-2, mIL-15/mIL-7, mIL-15/mproIL-18(K89A) and mIL-15/mIL-21), the IL-15 entity is designed so as to comprise the IL-2 peptide signal that is fused in frame to the mature murine IL-15 (as depicted in SEQ ID NO: 5). The control Ad-mIL-15 also comprises the mature IL-15 preceded by the peptide signal of IL-2.

Expression of the IL-15 containing fusions was determined by Western blot in A549 cells infected with the different Ad-vectors as described in Material and Methods. Low expression and secretion levels were detected for most of the IL-15 containing fusions as well as Ad-mIL-15, except for mIL-15/mIL-7, mIL-21/mIL-15 and mIL-15/mproIL-18 (K89A) fusions which were secreted at high levels into the culture medium of infected A549 cells.

The anti-tumoral activity of adenovirus encoding IL-15-based fusion cytokines was investigated in mice bearing B16F10 tumors that were treated by three intratumoral injections. Tumor growth was evaluated for 43 days post implantation. As illustrated in FIG. 9, intratumoral injection of Ad-mIL-15/mL-7, Ad-mIL-21/mL-15 and Ad-mIL-15/mproIL-18(K89A) allows a statistical control of tumor growth in the treated animals as compared to intratumoral injection of an Ad without transgene (Ad-empty) or the control Ad-mIL-15 expressing mIL-15 alone.

In order to improve secretion of IL-15 in the fusion, additional constructs were designed to evaluate other signal peptides. In the Ad-mIL-15 construct, the IL-2 signal peptide was replaced by either the endogenous IL-15 peptide signal in its long version without (spLSP) or short natural form (spLSP splice) (Kurys et al., 2000, J. Biol. Chem. 275, 30653) or by a heterologous signal peptide obtained from Kappa light chain of a mouse immunoglobin G (spVKL) (Meazza et al., 2000, Int. J. Cancer 87, 574). The expression and secretion of IL-15 driven by the respective signal peptides was evaluated by Western blot and compared to the original construct equipped with the IL-2 signal peptide. The results show that the use of the IL-15 endogenous peptide signal (short version) and especially the IgG signal peptide could improve importantly the level of IL-15 secretion by a factor 3 to ten. Moreover, the anti-tumor activity of the adenovirus encoding IL-15 cytokine controlled by the various signal peptides was investigated in mice bearing B16F10 tumors. As illustrated in FIG. 10, intratumoral injection the highly secretable Ad-IL-15 construct using the IgG signal peptide vKL provides a much higher survival rate than the other forms of IL-15. Construction of fusion cytokines incorporating the signal peptide vKL-IL-15 version is being performed in order to improve the activity and immunoadjuvant effect of IL-15/IL-7, IL-21/IL-15, and IL-15/proIL-18(K89A) fusions.

General Discussion

The availability of recombinant cytokines has enabled research into cytokine biology as well as their application in a clinical setting. One aspect which is becoming clear is that the systemic injection of large doses of cytokines is associated with considerable toxicity, usually due to or accompanied by, vascular leak syndrome. In addition to its systemic toxicity, the therapeutic value of IL-2 is also limited by its short half life. One approach reported in the literature to overcome the toxicity and short life problems is to fuse IL-2 to an antibody (IL-2 immunocytokine) or a protein with a long half life, to target the fusion to a unique antigen/receptor within the body. In a different approach, the present invention provides a series of cytokine fusion proteins in an effort to combine cytokines which stimulate the innate immune system with cytokines which promote an adaptive immune response. A variety of cytokines, including IFNg, IL-7, IL-12, IL-15, IL-18 and IL-21 were genetically fused to IL-2 and produced using E1 and E3-deleted adenovirus expression system in order to explore their in vitro and in vivo biological properties and anti tumor activity following intratumoral injection. Of these, several fusion cytokines have shown interesting properties, which include the maintenance of biological activity of the two cytokines engaged in the fusion and, importantly, a reduced toxicity (e.g. mIL2/proIL18 and mIL7/IL2). Moreover, the present invention illustrates that a number of the described Ad-fusion cytokines are effective for treating tumors of various origins (e.g. Ad-m IL-7/IL-2, Ad-mIL-21/mL-2, Ad-mIFNg/mL-2 and Ad-mIL-2/mproIL-18).

More particularly, the results illustrated in the present examples show that the location of each cytokine with respect to each other may influence expression and biological activity at least in adenoviral system. In this consideration, secretion and activity of the IL-2 and IL-18 entities was found much more efficient when IL-2 is located at the N-terminus of the fusion, (IL-2/IL-18 fusion) than when IL-2 is placed at the C-terminus of IL-18. In contrast, more efficient fusion cytokines between IL-2 and IL-7 were obtained when IL-2 is located at the C-terminus of the IL-7 entity (see Examples 1 and 2).

Moreover, it is known that IL-18 is produced in a precursor form (proIL-18) initially. The IL-18 precursor should be cleaved by the enzyme Caspase-3/ICE to be secreted (Dinarello et al., 1999, Interleukin-18 Methods 19, 121-132). Examples 1 and 2 illustrate that fusion cytokines incorporating pro-IL-18 are more effectively expressed than those containing the mature IL-18. On this basis, one may assume that upon expression of the IL-2/proIL-18 fusion cytokine, pro-IL18 is correctly folded and secreted, presumably as a result of the IL-2-associated signal sequence.

A mutation of IL-18 (K89A) was recently reported to augment the biological activity of IL-18. IL18(K89A)-containing fusion cytokines also exhibit an improvement of functionality in all biological assays tested. More importantly, Example 3 shows that the IL18(K89A)-containing fusion cytokines display in addition a markedly reduced cytokine related toxicity as assessed by Annexin V, Fas induction (AICD) or Vascular leak (VLS). Interestingly, biological activity of the mIL2/mpro-IL18(K89A) fusion cytokine appears to be maintained at a much lower and thus less or non toxic protein concentration than required for biological activity of the individual cytokines. The reduced toxicity pattern obtained with the mIL-2/proIL-18(K89A) fusion may be an effect of the structural modification of the cytokines engaged in the fusion protein. It is also possible that the murine fusion cytokine activates a specific population of IL-2 receptor expressing effector cells, thus reducing the apparent toxicity of recombinant IL-2 (Bensinger et al., 2004, J. Immunol. 172, 5287-5296).

It is well known that T cell stimulation of individual IL-2 or IL-18 cytokine to produce IFNg requires the pre-activation of splenic T cells by Con-A (Osaki et al., 1998, J. Immunol. 160, 1742-1749; Osaki et al., 1999, Gene Ther. 6, 808-815; Hwang et al., 2004, Cancer Gene Ther. 11, 397.407) Interestingly, as shown in example 2, the mIL-2/mproIL-18 fusion cytokine does not require pre-stimulation of T cells for this activity. Thus, not only are IL-2 and IL-18 biological activities maintained and cytokine related toxicity reduced, but the mIL-2/proIL-18 fusion protein appears to have a novel activity which either individual cytokine is unable to exert.

As illustrated in Example 4, a very effective anti-tumor protection has been obtained following intratumoral injection of Ad-mIL-2/mproIL-18(K89A) in all tumor models tested, including the very aggressive B16F10 model. Antitumor activity provided by Ad-mIL-2/mproIL-18(K89A) was much higher than that obtained following intratumoral injection of either Ad-IL-2 or Ad-proIL-18 alone or the combination of the two individual constructs. Depletion experiments demonstrate clearly that both the innate (NK, cells) immune system as well as the adaptive (CD8) immune response are involved in this therapeutic effect. Immuno-histological analysis of the injected tumors indicate that the anti-tumor activity provided by Ad-mIL2/pro-IL18(K89A) is associated with infiltration of activated T cells and antigen presenting cells. Surprisingly, tumors injected with Ad(mIL-2/proIL-18(K89A) are highly positive for von Willebrand factor, suggesting increased vascularization. While vascularization of tumors is normally associated with poor prognosis, in this case it may be associated with an increased infiltration by immune effector cells. Moreover, mIL-2/proIL-18(K89A) fusion cytokine displays a reduced AICD activity which seems to be crucial in the induction of tumor specific T cells (Saff et al., 2004, J. Immunol. 172, 6598-6606).

In conclusion, on the basis of the above-discussed results, the fusion cytokines of the present invention have a great potential for both increasing the therapeutic activity of cytokines, and reducing the toxic side effects.

The invention claimed is:

1. An isolated infectious viral particle comprising a polynucleotide encoding a fusion protein, wherein said fusion protein comprises the amino acid sequence of SEQ ID NO:1.

2. The isolated infectious viral particle of claim 1, wherein:
said isolated infectious viral particle comprises a viral vector;
said viral vector comprises a polynucleotide encoding a fusion protein; and
said fusion protein comprises the amino acid sequence of SEQ ID NO:1.

3. The infectious viral particle of claim 2, wherein said viral vector is selected from the group consisting of baculoviral vectors, papoviral vectors, herpes viral vectors, adenoviral vectors, adenovirus-associated viral vectors, poxviral vectors, foamy viral vectors, and retroviral vectors.

4. The isolated infectious viral particle of claim 3, wherein said viral vector is an adenoviral vector.

5. The isolated infectious viral particle of claim 4, wherein:
said adenoviral vector is an E1- and E3-deleted replication-defective adenoviral vector comprising a polynucleotide encoding a fusion protein inserted in replacement of the E1 region;
said fusion protein comprises the amino acid sequence of SEQ ID NO:1; and
said polynucleotide encoding a fusion protein is placed under the control of a CMV promoter.

6. The isolated infectious viral particle of claim 2, wherein said viral vector further comprises one or more transgenes encoding (i) a tumor proliferation inhibitor and/or (ii) at least one antigen.

7. The isolated infectious viral particle of claim 6, wherein said tumor proliferation inhibitor is a fusion protein encoding a two domain enzyme possessing both CDase and UPRTase activities.

8. The isolated infectious viral particle of claim 6, wherein said antigen is a HPV antigen selected from the group consisting of E5, E6, E7, L1, L2, and combinations thereof.

9. The isolated infectious viral particle of claim 8, wherein said HPV antigen is a membrane-anchored form of a non-oncogenic variant of the early HPV-16 E6 and/or E7 antigen.

10. An isolated host cell comprising the infectious viral particle of claim 1.

11. An isolated host cell comprising the infectious viral particle of claim 2.

12. A composition comprising the infectious viral particle of claim 1 and a pharmaceutically acceptable vehicle.

13. A composition comprising the infectious viral particle of claim 2 and a pharmaceutically acceptable vehicle.

14. A composition comprising the isolated host cell of claim 10 and a pharmaceutically acceptable vehicle.

15. A composition comprising the isolated host cell of claim 11 and a pharmaceutically acceptable vehicle.

16. A process for producing the infectious viral particle of claim 1, comprising the steps of:
(a) introducing a viral vector into a suitable cell line, wherein said viral vector comprises a polynucleotide encoding a fusion protein, and said fusion protein comprises the amino acid sequence of SEQ ID NO:1;
(b) culturing said cell line under suitable conditions so as to allow the production of said infectious viral particle;
(c) recovering the produced infectious viral particle from the culture of said cell line; and
(d) optionally purifying said recovered infectious viral particle.

* * * * *